(12) United States Patent
Zhu et al.

(10) Patent No.: US 12,030,884 B2
(45) Date of Patent: Jul. 9, 2024

(54) PYRAZOLOQUINOLINE KRAS INHIBITORS

(71) Applicant: INCYTE CORPORATION, Wilmington, DE (US)

(72) Inventors: Wenyu Zhu, Wilmington, DE (US); Xiaozhao Wang, Mt. Laurel, NJ (US); Wenqing Yao, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/937,106

(22) Filed: Sep. 30, 2022

(65) Prior Publication Data

US 2023/0143938 A1    May 11, 2023

Related U.S. Application Data

(60) Provisional application No. 63/261,982, filed on Oct. 1, 2021.

(51) Int. Cl.
  *C07D 471/04* (2006.01)
(52) U.S. Cl.
  CPC .................. *C07D 471/04* (2013.01)
(58) Field of Classification Search
  None
  See application file for complete search history.

(56) References Cited

U.S. PATENT DOCUMENTS

| | | | |
|---|---|---|---|
| 7,592,453 B2 | 9/2009 | Kajino et al. |
| 7,897,609 B2 | 3/2011 | Niwas et al. |
| 7,943,770 B2 | 5/2011 | Kajino et al. |
| 7,973,163 B2 | 7/2011 | Kajino et al. |
| 8,034,802 B2 | 10/2011 | Averett |
| 8,143,270 B2 | 3/2012 | Kshirsagar et al. |
| 8,158,794 B2 | 4/2012 | Kshirsagar et al. |
| 8,207,187 B2 | 6/2012 | Beek et al. |
| 8,513,250 B2 | 8/2013 | Escaich et al. |
| 8,557,984 B2 | 10/2013 | Bouillot et al. |
| 8,563,565 B2 | 10/2013 | Norimine et al. |
| 8,637,670 B2 | 1/2014 | Kumar et al. |
| 8,658,666 B2 | 2/2014 | Rice et al. |
| 8,846,710 B2 | 9/2014 | Kshirsagar et al. |
| 8,895,581 B2 | 11/2014 | McConnell et al. |
| 9,062,046 B2 | 6/2015 | Kumar et al. |
| 9,169,246 B2 | 10/2015 | Benazet et al. |
| 9,550,776 B2 | 1/2017 | Norimine et al. |
| 9,573,947 B2 | 2/2017 | Ozaki |
| 9,694,006 B2 | 7/2017 | Beck et al. |
| 9,771,327 B2 | 9/2017 | Zawistoski et al. |
| 9,873,694 B2 | 1/2018 | Lipford et al. |
| 9,960,359 B2 | 5/2018 | Hwang et al. |
| 10,039,753 B2 | 8/2018 | Coffman et al. |
| 10,493,071 B2 | 12/2019 | Beck et al. |
| 10,544,138 B2 | 1/2020 | Gray et al. |
| 11,053,240 B2 | 7/2021 | Li et al. |
| 2005/0054590 A1 | 3/2005 | Averett |
| 2011/0230476 A1 | 9/2011 | Niu et al. |
| 2012/0065187 A1 | 3/2012 | Borchardt et al. |
| 2012/0108627 A1 | 5/2012 | Kumar et al. |
| 2012/0232074 A1 | 9/2012 | Bouillot et al. |
| 2014/0243286 A1 | 8/2014 | Arnold et al. |
| 2016/0264570 A1 | 9/2016 | McKew et al. |
| 2017/0197945 A1 | 7/2017 | Li et al. |
| 2017/0217960 A1 | 8/2017 | Ferguson |
| 2017/0294489 A1 | 10/2017 | Lim et al. |
| 2019/0177338 A1 | 6/2019 | Kettle et al. |
| 2021/0230162 A1 | 7/2021 | Zhao et al. |
| 2021/0269434 A1 | 9/2021 | Wang et al. |
| 2021/0308123 A1 | 10/2021 | Zhang et al. |
| 2021/0317118 A1 | 10/2021 | Zhang et al. |
| 2021/0355121 A1* | 11/2021 | Zhu .................. A61P 29/00 |
| 2021/0355141 A1 | 11/2021 | Hoang et al. |
| 2022/0064188 A1 | 3/2022 | Carlsen et al. |
| 2022/0106309 A1 | 4/2022 | Huang et al. |
| 2022/0306633 A1 | 9/2022 | Qi et al. |
| 2022/0389033 A1 | 12/2022 | Sokolsky et al. |

FOREIGN PATENT DOCUMENTS

| | | |
|---|---|---|
| CN | 102399218 A | 4/2012 |
| CN | 103012397 B | 3/2017 |
| CN | 108003153 A | 5/2018 |
| EP | 1 740 584 B1 | 3/2008 |
| EP | 2 573 073 B1 | 10/2014 |
| EP | 1 945 211 B1 | 10/2015 |
| EP | 2 769 980 A1 | 3/2016 |
| EP | EP 2 760 841 B1 | 8/2016 |
| EP | 2 982 674 B1 | 10/2017 |
| IN | 2012MUM02281 A | 6/2014 |

(Continued)

OTHER PUBLICATIONS

Patani et al. "Bioisosterism: A Rational Approach in Drug Design" Chemical Reviews, 1996, vol. 96, pp. 3147-3176.*
Bauer, R.A., "Covalent inhibitors in drug discovery: from accidental discoveries to avoided liabilities and designed therapies", *Drug Discovery Today* 20(9):1061-1073 (2015).
International Search Report and Written Opinion for International Application No. PCT/US2022/077350, dated Nov. 24, 2022, 13 pages.
Korzeniecki et al., "Targeting KRAS mutant cancers by preventing signaling transduction in the MAPK pathway", *European Journal of Medicinal Chemistry* 211 (2021) 113006.
Ostrem et al., "K-Ras (G12C) inhibitors allosterically control GTP affinity and effector interactions", *Nature* 503(7477):548-551 (2013).
Written Opinion of the International Searching Authority for PCT/US2021/027513, dated Oct. 21, 2021, 6 pages.

(Continued)

*Primary Examiner* — Joseph R Kosack
(74) *Attorney, Agent, or Firm* — Lathrop GPM LLP; Brian C. Trinque; Nicole Sassu

(57) ABSTRACT

Disclosed are compounds of Formula I, methods of using the compounds for inhibiting KRAS activity and pharmaceutical compositions comprising such compounds. The compounds are useful in treating, preventing or ameliorating diseases or disorders associated with KRAS activity such as cancer.

26 Claims, No Drawings

(56) References Cited

FOREIGN PATENT DOCUMENTS

| WO | WO 1994/014777 A1 | 7/1994 |
|----|----|----|
| WO | WO 2001/042247 A1 | 6/2001 |
| WO | WO 2005/105802 A1 | 11/2005 |
| WO | WO 2007/054693 A1 | 5/2007 |
| WO | WO 2008/056151 A1 | 5/2008 |
| WO | WO 2009/123967 A1 | 10/2009 |
| WO | WO 2010/030785 A2 | 3/2010 |
| WO | WO 2010/049366 A1 | 5/2010 |
| WO | WO 2010/135571 A1 | 11/2010 |
| WO | WO 2011/031896 A2 | 3/2011 |
| WO | WO 2012/011642 A1 | 1/2012 |
| WO | WO 2012/116623 A1 | 9/2012 |
| WO | WO 2012/154731 A1 | 11/2012 |
| WO | WO 2013/045400 A1 | 4/2013 |
| WO | WO 2013/051639 A1 | 4/2013 |
| WO | WO 2013/059559 A2 | 4/2013 |
| WO | WO 2014/163146 A1 | 10/2014 |
| WO | WO 2016/161361 A1 | 10/2016 |
| WO | WO 2016/168540 A1 | 10/2016 |
| WO | WO 2016/199943 A1 | 12/2016 |
| WO | WO 2017/058805 A1 | 4/2017 |
| WO | WO 2017/092413 A1 | 6/2017 |
| WO | WO 2018/119183 A2 | 6/2018 |
| WO | WO 2018/217651 A1 | 11/2018 |
| WO | WO 2019/150305 A1 | 8/2019 |
| WO | WO 2019/177971 A1 | 9/2019 |
| WO | WO 2019/201283 A1 | 10/2019 |
| WO | WO 2019/209896 A1 | 10/2019 |
| WO | WO 2019/213516 A1 | 11/2019 |
| WO | WO 2020/037091 A1 | 2/2020 |
| WO | WO 2020/037092 A1 | 2/2020 |
| WO | WO 2020/051207 A2 | 3/2020 |
| WO | WO 2021/063346 A1 | 4/2021 |
| WO | WO 2021/211864 A1 | 10/2021 |
| WO | WO 2022/037631 A1 | 2/2022 |
| WO | WO 2022/047093 A1 | 3/2022 |

OTHER PUBLICATIONS

Zhu et al., "Structure-based discovery of selective BRPF1 bromodomain inhibitors", *European Journal of Medicinal Chemistry* 155:337-352 (2018).

Chen et al., "Small-Molecule Inhibitors Directly Targeting KRAS as Anticancer Therapeutics", *Journal of Medicinal Chemistry* 63(3):14404-14424 (2020).

Cox et al., "Drugging the undruggable Ras: mission impossible?", *Nature Reviews Drug Discovery* 13(11):828-851 (2014).

Fernandez-Medarde et al., "Ras in Cancer and Developmental Diseases", *Genes & Cancer* 2(3):344-358 (2011).

\* cited by examiner

PYRAZOLOQUINOLINE KRAS INHIBITORS

RELATED APPLICATIONS

This application claims priority to U.S. Provisional Application No. 63/261,982, filed Oct. 1, 2021, the entire content of which is hereby incorporated by reference in its entirety.

FIELD OF THE INVENTION

The disclosure provides compounds as well as their compositions and methods of use. The compounds modulate KRAS activity and are useful in the treatment of various diseases including cancer.

BACKGROUND OF THE INVENTION

Ras proteins are part of the family of small GTPases that are activated by growth factors and various extracellular stimuli. The Ras family regulates intracellular signaling pathways responsible for growth, migration, survival and differentiation of cells. Activation of RAS proteins at the cell membrane results in the binding of key effectors and initiation of a cascade of intracellular signaling pathways within the cell, including the RAF and PI3K kinase pathways. Somatic mutations in RAS may result in uncontrolled cell growth and malignant transformation while the activation of RAS proteins is tightly regulated in normal cells (Simanshu, D. et al. Cell 170.1 (2017):17-33).

The Ras family is comprised of three members: KRAS, NRAS and HRAS. RAS mutant cancers account for about 25% of human cancers. KRAS is the most frequently mutated isoform accounting for 85% of all RAS mutations whereas NRAS and HRAS are found mutated in 12% and 3% of all Ras mutant cancers respectively (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residue 12, 13, and 61. The frequency of specific mutations varies between RAS gene isoforms and while G12 and Q61 mutations are predominant in KRAS and NRAS respectively, G12, G13 and Q61 mutations are most frequent in HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) while KRAS G12V mutations are associated with pancreatic cancers (30%), followed by colorectal adenocarcinomas (27%) and lung adenocarcinomas (23%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas, and 2-5% of pancreatic and colorectal adenocarcinomas (Cox, A. D. et al. Nat. Rev. Drug Discov. (2014) 13:828-51). Genomic studies across hundreds of cancer cell lines have demonstrated that cancer cells harboring KRAS mutations are highly dependent on KRAS function for cell growth and survival (McDonald, R. et al. Cell 170 (2017): 577-592). The role of mutant KRAS as an oncogenic driver is further supported by extensive in vivo experimental evidence showing mutant KRAS is required for early tumour onset and maintenance in animal models (Cox, A. D. et al. Nat Rev Drug Discov (2014) 13:828-51).

Taken together, these findings suggest that KRAS mutations play a critical role in human cancers; development of inhibitors targeting mutant KRAS may therefore be useful in the clinical treatment of diseases that are characterized by a KRAS mutation.

SUMMARY

The present disclosure provides, inter alia, a compound of Formula I:

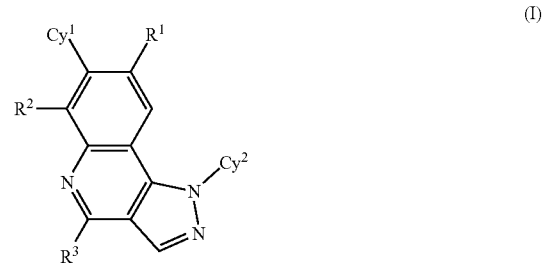

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting KRAS activity, which comprises administering to an individual a compound of the disclosure, or a pharmaceutically acceptable salt thereof. The present disclosure also provides uses of the compounds described herein in the manufacture of a medicament for use in therapy. The present disclosure also provides the compounds described herein for use in therapy.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

In an aspect, provided herein is a compound having Formula I:

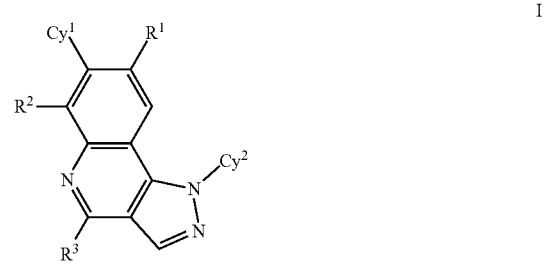

or a pharmaceutically acceptable salt thereof, wherein:
R¹ is selected from Cl, CH₃, CH₂F, CHF₂, and CF₃;
Cy¹ is selected from

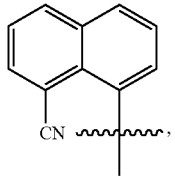
Cy¹-a

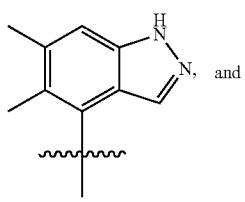
Cy¹-b

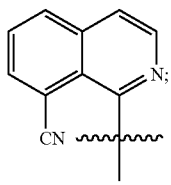
Cy¹-c

R² is selected from F and Cl;
R³ is selected from

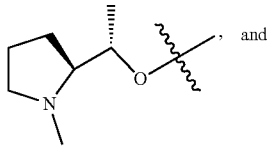
R³-a

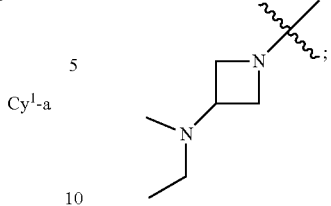
R³-b and,
Cy² is selected from

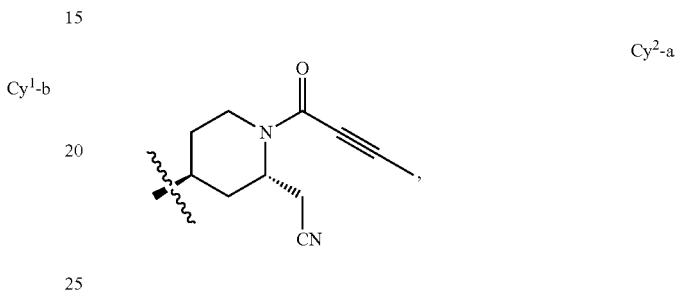
Cy²-a

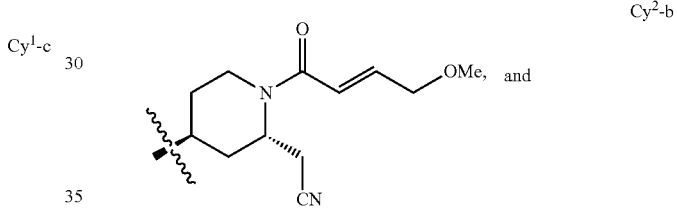
Cy²-b

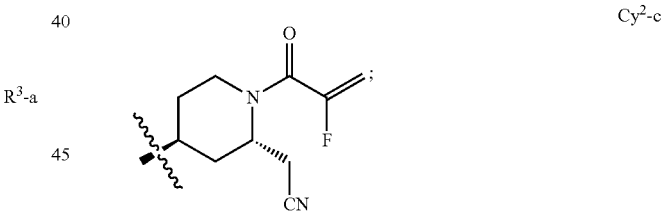
Cy²-c provided ta the compound of Formula I is other than, 8-(1-((2S,4S)-2-(cyanomethyl)-1-(2-fluoroacryloyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile;
8-(1-((2S,4S)-2-(cyanomethyl)-1-((E)-4-methoxybut-2-enoyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile;
2-((2S,4S)-4-(7-(5,6-dimethyl-1H-indazol-4-yl)-6-fluoro-8-methyl-4-((S)-1-((S)-1-methylpyrrolidin-2-yl)ethoxy)-1H-pyrazolo[4,3-c]quinolin-1-yl)-1-(2-fluoroacryloyl)piperidin-2-yl)acetonitrile;
2-((2S,4S)-1-(but-2-ynoyl)-4-(7-(5,6-dimethyl-1H-indazol-4-yl)-6-fluoro-8-methyl-4-((S)-1-((S)-1-methylpyrrolidin-2-yl)ethoxy)-1H-pyrazolo[4,3-c]quinolin-1-yl)piperidin-2-yl)acetonitrile; and
2-((2S,4S)-4-(7-(5,6-dimethyl-1H-indazol-4-yl)-6-fluoro-8-methyl-4-((S)-1-((S)-1-methylpyrrolidin-2-yl) ethoxy)-1H-pyrazolo[4,3-c]quinolin-1-yl)-1-((E)-4-methoxybut-2-enoyl)piperidin-2-yl)acetonitrile.

In an embodiment or Formula I, or a pharmaceutically acceptable salt thereof, $R^1$ is selected from Cl, $CH_2F$, $CHF_2$, and $CF_3$;

$Cy^1$ is selected from

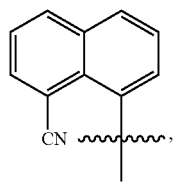
Cy¹-a

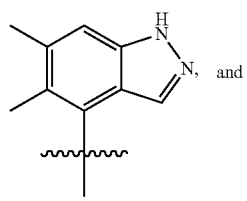
Cy¹-b

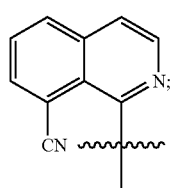
Cy¹-c $R^2$ is selected from F and Cl;

$R^3$ is selected from

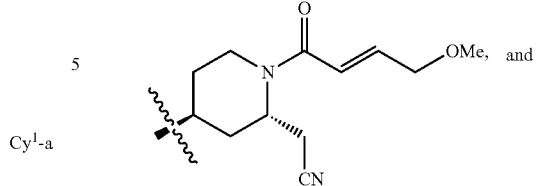
R³-a

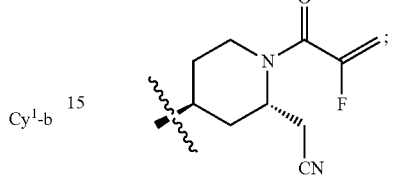
R³-b and, $Cy^2$ is selected from

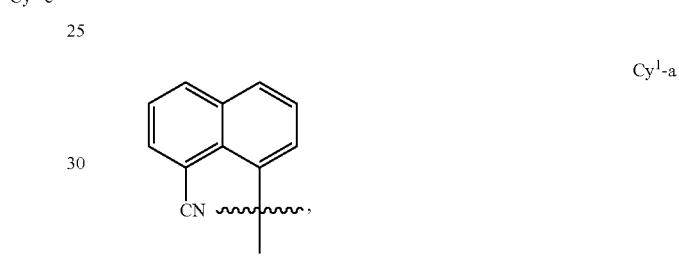
Cy²-a

Cy²-b

Cy²-c

In another embodiment or Formula I, or a pharmaceutically acceptable salt thereof, $R^1$ is Cl;

$Cy^1$ is selected from

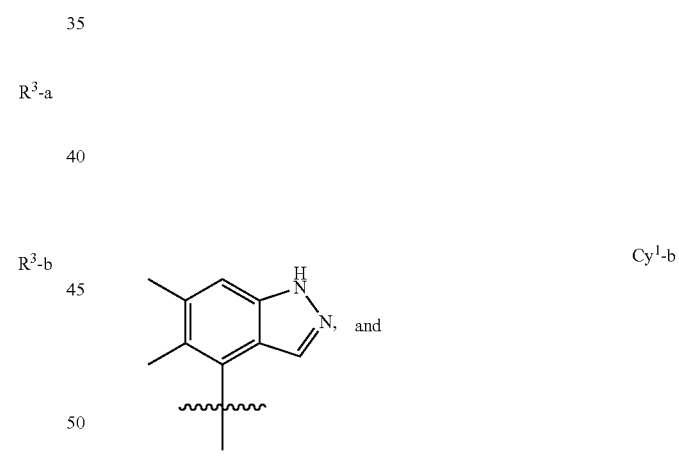
Cy¹-a

Cy¹-b

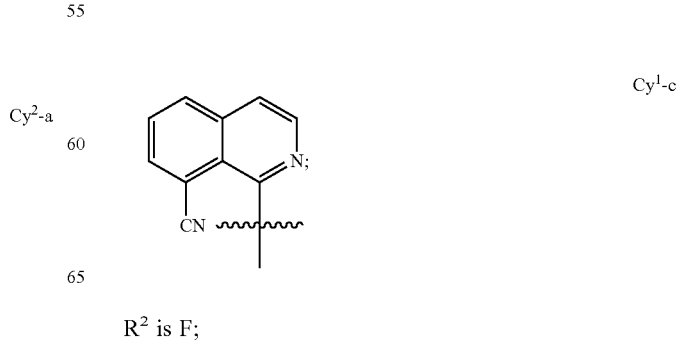
Cy¹-c $R^2$ is F;

R³ is

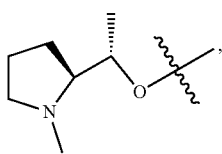

and,
Cy² is selected from

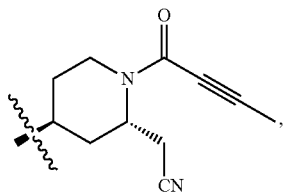

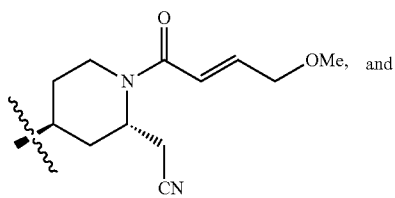, and

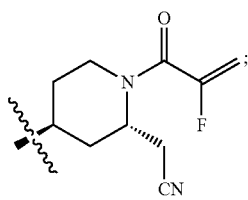;

R³-a

Cy²-a

Cy²-b

Cy²-c

In an embodiment of Formula I, or a pharmaceutically acceptable salt thereof, $R^1$ is selected from Cl, $CH_2F$, $CHF_2$, and $CF_3$. In yet another embodiment, $R^1$ is selected from $CH_3$, $CH_2F$, $CHF_2$, and $CF_3$. In still another embodiment, $R^1$ is selected from Cl, $CH_3$, and $CF_3$.

In an embodiment of Formula I, or a pharmaceutically acceptable salt thereof, $R^1$ is selected from $CH_2F$, $CHF_2$, and $CF_3$. In another embodiment, $R^1$ is selected from Cl and $CH_3$. In yet another embodiment, $R^1$ is selected from Cl and $CF_3$. In still another embodiment, $R^1$ is selected from $CH_3$ and $CF_3$.

In an embodiment of Formula I, or a pharmaceutically acceptable salt thereof, $R^1$ is Cl. In another embodiment, $R^1$ is $CH_3$. In yet another embodiment, $R^1$ is $CH_2F$. In still another embodiment, $R^1$ is $CHF_2$. In an embodiment, $R^1$ is $CF_3$.

In an embodiment of Formula I, or a pharmaceutically acceptable salt thereof, $Cy^1$ is selected from $Cy^1$-a and $Cy^1$-b. In another embodiment, $Cy^1$ is selected from $Cy^1$-a and $Cy^1$-c. In yet another embodiment, $Cy^1$ is selected from $Cy^1$-b and $Cy^1$-c.

In an embodiment of Formula I, or a pharmaceutically acceptable salt thereof, $Cy^1$ is $Cy^1$-a. In another embodiment, $Cy^1$ is $Cy^1$-b. In another embodiment, $Cy^1$ is $Cy^1$-c.

In an embodiment of Formula I, or a pharmaceutically acceptable salt thereof, $R^2$ is F. In another embodiment, $R^2$ is Cl.

In an embodiment of Formula I, or a pharmaceutically acceptable salt thereof, $R^3$ is $R^3$-a. In another embodiment, $R^3$ is $R^3$-b.

In an embodiment of Formula I, or a pharmaceutically acceptable salt thereof, $Cy^2$ is selected from $Cy^2$-a and $Cy^2$-b. In another embodiment, $Cy^2$ is selected from $Cy^2$-a and $Cy^2$-c. In another embodiment, $Cy^2$ is selected from $Cy^2$-b and $Cy^2$-c. In another embodiment, $Cy^2$ is $Cy^2$-a. In yet another embodiment, $Cy^2$ is $Cy^2$-b. In still another embodiment, $Cy^2$ is $Cy^2$-c.

In an embodiment of Formula I, or a pharmaceutically acceptable salt thereof, $Cy^1$ is $Cy^1$-a and $Cy^2$ is $Cy^2$-a.

In an embodiment of Formula I, or a pharmaceutically acceptable salt thereof, the compound of Formula I is other than 8-(1-((2S,4S)-2-(cyanomethyl)-1-(2-fluoroacryloyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile;

8-(1-((2S,4S)-2-(cyanomethyl)-1-((E)-4-methoxybut-2-enoyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile;

2-((2S,4S)-4-(7-(5,6-dimethyl-1H-indazol-4-yl)-6-fluoro-8-methyl-4-((S)-1-((S)-1-methylpyrrolidin-2-yl)ethoxy)-1H-pyrazolo[4,3-c]quinolin-1-yl)-1-(2-fluoroacryloyl)piperidin-2-yl)acetonitrile;

2-((2S,4S)-1-(but-2-ynoyl)-4-(7-(5,6-dimethyl-1H-indazol-4-yl)-6-fluoro-8-methyl-4-((S)-1-((S)-1-methylpyrrolidin-2-yl)ethoxy)-1H-pyrazolo[4,3-c]quinolin-1-yl)piperidin-2-yl)acetonitrile; and 2-((2S,4S)-4-(7-(5,6-dimethyl-1H-indazol-4-yl)-6-fluoro-8-methyl-4-((S)-1-((S)-1-methylpyrrolidin-2-yl)ethoxy)-1H-pyrazolo[4,3-c]quinolin-1-yl)-1-((E)-4-methoxybut-2-enoyl)piperidin-2-yl)acetonitrile.

In an embodiment, the compound of Formula I is selected from 1-(1-((2S,4S)-1-(but-2-ynoyl)-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile;

1-(8-chloro-1-((2S,4S)-2-(cyanomethyl)-1-((E)-4-methoxybut-2-enoyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile;

1-(8-chloro-1-((2S,4S)-2-(cyanomethyl)-1-(2-fluoroacryloyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile;

2-((2S,4S)-4-(8-chloro-7-(5,6-dimethyl-1H-indazol-4-yl)-4-(3-(ethyl(methyl)amino)azetidin-1-yl)-6-fluoro-1H-pyrazolo[4,3-c]quinolin-1-yl)-1-(2-fluoroacryloyl)piperidin-2-yl)acetonitrile;

8-(8-chloro-1-((2S,4S)-2-(cyanomethyl)-1-(2-fluoroacryloyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile;

8-(8-chloro-1-((2S,4S)-2-(cyanomethyl)-1-((E)-4-methoxybut-2-enoyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile; and 8-(1-((2S,4S)-1-(but-2-ynoyl)-2-(cyanomethyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile;

or a pharmaceutically acceptable salt thereof.

In another embodiment, the compound of Formula I is selected from 1-(1-((2S,4S)-1-(but-2-ynoyl)-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile;

1-(8-chloro-1-((2S,4S)-2-(cyanomethyl)-1-((E)-4-methoxybut-2-enoyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile;

1-(8-chloro-1-((2S,4S)-2-(cyanomethyl)-1-(2-fluoroacryloyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile;

2-((2S,4S)-4-(8-chloro-7-(5,6-dimethyl-1H-indazol-4-yl)-4-(3-(ethyl(methyl)amino)azetidin-1-yl)-6-fluoro-1H-pyrazolo[4,3-c]quinolin-1-yl)-1-(2-fluoroacryloyl)piperidin-2-yl)acetonitrile;

8-(8-chloro-1-((2S,4S)-2-(cyanomethyl)-1-(2-fluoroacryloyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile; and 8-(8-chloro-1-((2S,4S)-2-(cyanomethyl)-1-((E)-4-methoxybut-2-enoyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile;

or a pharmaceutically acceptable salt thereof.

In yet another embodiment, the compound of Formula I is 8-(1-((2S,4S)-1-(but-2-ynoyl)-2-(cyanomethyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile, or a pharmaceutically acceptable salt thereof.

In still another embodiment, the compound of Formula I is 1-(8-chloro-1-((2S,4S)-2-(cyanomethyl)-1-(2-fluoroacryloyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile, or a pharmaceutically acceptable salt thereof.

In another embodiment, compounds of the formulae herein are compounds of the formulae or pharmaceutically acceptable salts thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound" as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups.

The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J.* Chem. Educ., 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high-performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

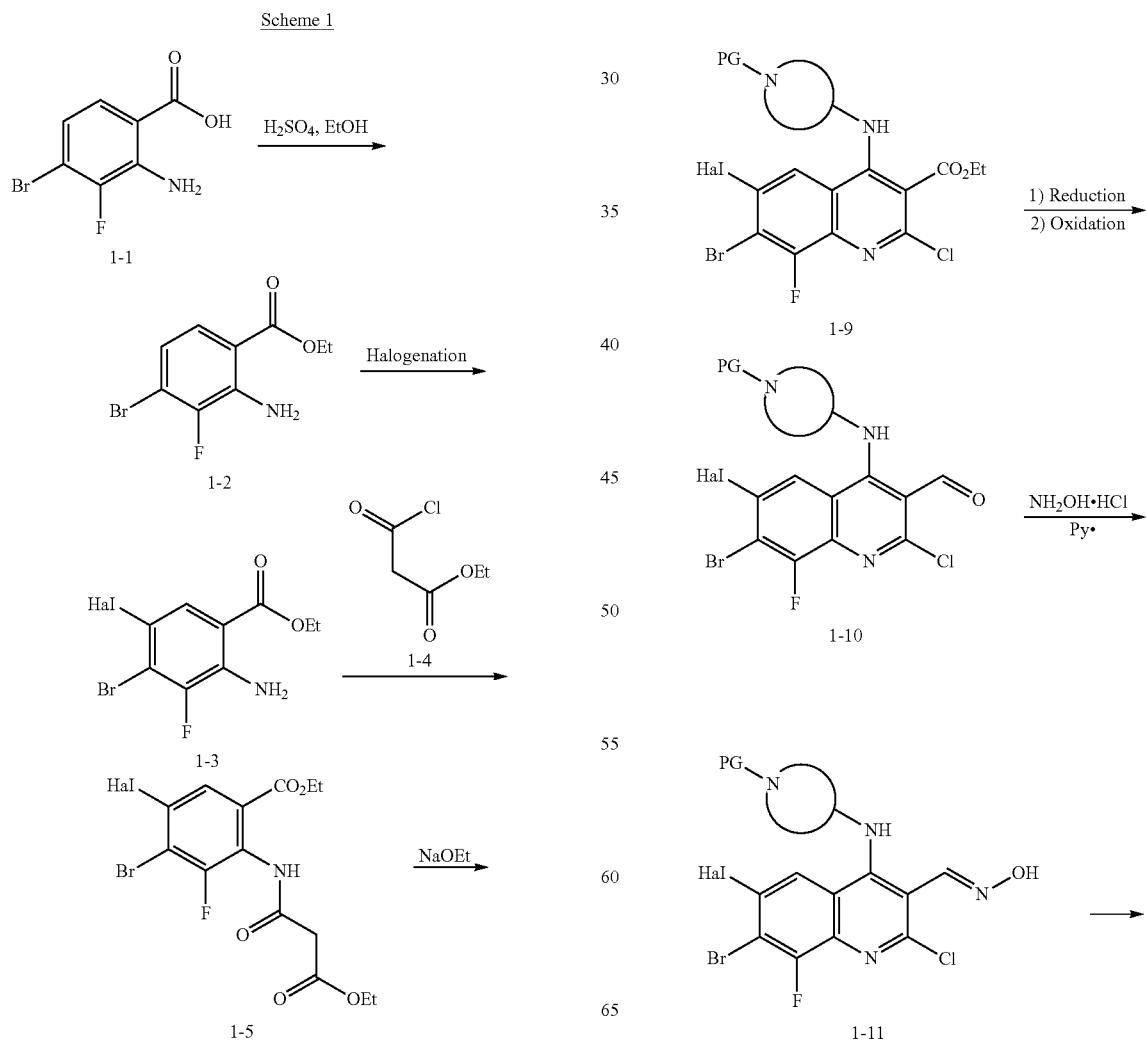

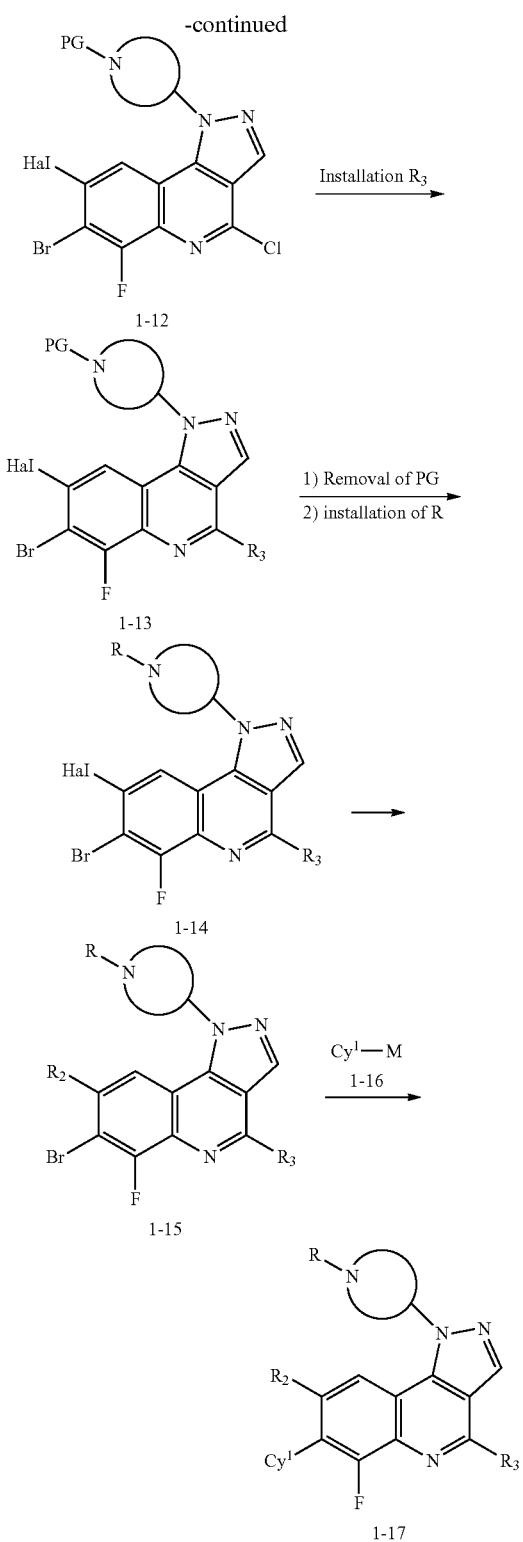

such as ethyl malonyl chloride (1-4). Intermediate 1-5 can undergo a cyclization reaction (such as sodium ethoxide in ethanol) to deliver the compound 1-6, which can be treated with an appropriate reagent (e.g. $POCl_3$) to afford compound 1-7. Condensation of intermediate 1-7 with amine 1-8 (PG is an appropriate protecting group, such as Boc) can be carried out to generate compound 1-9. Reduction of ester with reducing reagent (such as DIBAL), followed by oxidation of intermediate with oxidation reagent (such as Dess-Martin periodinane) to yield aldehyde 1-10. Treatment of intermediate 1-10 with hydroxylamine hydrochloride and pyridine get compound 1-11. Intermediate 1-11 can undergo a cyclization reaction (such as methanesulfonyl chloride, aminopyridine in DCM) to deliver the compound 1-12. The $R^3$ group in 1-13 can then be installed via a suitable transformation, such as a $S_NAr$ reaction or a coupling reaction. Intermediate 1-13 can first undergo a deprotection of protecting group PG, followed by functionalization of the resulting amine (such as coupling with acid chloride, e.g. acryloyl chloride) then afford compound 1-14. The halogen of 1-14 (Hal) can optionally be converted to $R^2$ via transition metal mediated coupling or other suitable method to obtain 1-15. The desired product 1-17 can be prepared by a cross coupling reaction between 1-15 and an adduct of formula 1-16, in which M is a boronic acid, boronic ester or an appropriately substituted metal (e.g., M is $B(OR)_2$, $Sn(Alkyl)_3$, or Zn-Hal), under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). The order of the above described chemical reactions can be rearranged as appropriate to suite the preparation of different analogues.

KRAS Protein

The Ras family is comprised of three members: KRAS, NRAS and HRAS. RAS mutant cancers account for about 25% of human cancers. KRAS is the most frequently mutated isoform in human cancers: 85% of all RAS mutations are in KRAS, 12% in NRAS, and 3% in HRAS (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residues/codons 12, 13, and 61; Codon 12 mutations are most frequent in KRAS. The frequency of specific mutations varied between RAS genes and G12D mutations are most predominant in KRAS whereas Q61R and G12R mutations are most frequent in NRAS and HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas (nearly half of mutant KRAS is G12C), as well as 2-5% of pancreatic and colorectal adenocarcinomas, respectively (Cox, A. D. et al. Nat. Rev. Drug Discov. (2014) 13:828-51). Using shRNA knockdown thousands of genes across hundreds of cancer cell lines, genomic studies have demonstrated that cancer cells exhibiting KRAS mutations are highly dependent on KRAS function for cell growth (McDonald, R. et al. Cell 170 (2017): 577-592). Taken together, these findings suggested that KRAS mutations play a critical role in human cancers, therefore development of Compounds of formula 1-17 can be prepared via the synthetic route outlined in Scheme 1. Esterification of commercially available starting material 1-1 with $H_2SO_4$ in ethanol. Halogenation of compound 1-2 with an appropriate reagent, such as N-chlorosuccinimide (NCS), affords intermediate 1-3 (Hal is a halide, such as F, Cl, Br, or I). Compound 1-5 can be prepared by treating 1-3 with reagents the inhibitors targeting mutant KRAS may be useful in the clinical treatment of diseases that have characterized by a KRAS mutation.

Methods of Use

The cancer types in which KRAS harboring G12C, G12V and G12D mutations are implicated include, but are not limited to: carcinomas (e.g., pancreatic, colorectal, lung, bladder, gastric, esophageal, breast, head and neck, cervical skin, thyroid); hematopoietic malignancies (e.g., myeloproliferative neoplasms (MPN), myelodysplastic syndrome (MDS), chronic and juvenile myelomonocytic leukemia (CMML and JMML), acute myeloid leukemia (AML), acute lymphocytic leukemia (ALL) and multiple myeloma (MM)); and other neoplasms (e.g., glioblastoma and sarcomas). In addition, KRAS mutations were found in acquired resistance to anti-EGFR therapy (Knickelbein, K. et al. Genes & Cancer, (2015): 4-12). KRAS mutations were found in immunological and inflammatory disorders (Fernandez-Medarde, A. et al. Genes & Cancer, (2011): 344-358) such as Ras-associated lymphoproliferative disorder (RALD) or juvenile myelomonocytic leukemia (JMML) caused by somatic mutations of KRAS or NRAS.

Compounds of the present disclosure can inhibit the activity of the KRAS protein. For example, compounds of the present disclosure can be used to inhibit activity of KRAS in a cell or in an individual or patient in need of inhibition of the enzyme by administering an inhibiting amount of one or more compounds of the present disclosure to the cell, individual, or patient.

As KRAS inhibitors, the compounds of the present disclosure are useful in the treatment of various diseases associated with abnormal expression or activity of KRAS. Compounds which inhibit KRAS will be useful in providing a means of preventing the growth or inducing apoptosis in tumors, or by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In an aspect, provided herein is a method of inhibiting KRAS activity, said method comprising contacting a compound of the instant disclosure with KRAS. In an embodiment, the contacting comprises administering the compound to a patient.

In an aspect, provided herein is a method of inhibiting a KRAS protein harboring a G12C mutation, said method comprising contacting a compound of the instant disclosure with KRAS.

In an aspect, provided herein is a method of inhibiting a KRAS protein harboring a G12D mutation, said method comprising contacting a compound of the instant disclosure with KRAS.

In an aspect, provided herein is a method of inhibiting a KRAS protein harboring a G12V mutation, said method comprising contacting a compound of the instant disclosure with KRAS.

In another aspect, provided herein a is method of treating a disease or disorder associated with inhibition of KRAS interaction, said method comprising administering to a patient in need thereof a therapeutically effective amount of a compound of any of the formulae disclosed herein, or pharmaceutically acceptable salt thereof.

In yet another aspect, provided herein is a method of treating a disease or disorder associated with inhibiting a KRAS protein harboring a G12C mutation, said method comprising administering to a patient in need thereof a therapeutically effective amount of a compound of any of the formulae disclosed herein, or pharmaceutically acceptable salt thereof.

In still another aspect, provided herein is also a method of treating cancer in a patient in need thereof comprising administering to the patient a therapeutically effective amount of the compounds disclosed herein wherein the cancer is characterized by an interaction with a KRAS protein harboring a G12C mutation.

In yet another aspect, provided herein is a method of treating a disease or disorder associated with inhibiting a KRAS protein harboring a G12D mutation, said method comprising administering to a patient in need thereof a therapeutically effective amount of a compound of any of the formulae disclosed herein, or pharmaceutically acceptable salt thereof.

In still another aspect, provided herein is also a method of treating cancer in a patient in need thereof comprising administering to the patient a therapeutically effective amount of the compounds disclosed herein wherein the cancer is characterized by an interaction with a KRAS protein harboring a G12D mutation.

In yet another aspect, provided herein is a method of treating a disease or disorder associated with inhibiting a KRAS protein harboring a G12V mutation, said method comprising administering to a patient in need thereof a therapeutically effective amount of a compound of any of the formulae disclosed herein, or pharmaceutically acceptable salt thereof.

In still another aspect, provided herein is also a method of treating cancer in a patient in need thereof comprising administering to the patient a therapeutically effective amount of the compounds disclosed herein wherein the cancer is characterized by an interaction with a KRAS protein harboring a G12V mutation.

In yet another aspect, provided herein is a method for treating a cancer in a patient, said method comprising administering to the patient a therapeutically effective amount of any one of the compounds disclosed herein, or pharmaceutically acceptable salt thereof.

In an aspect, provided herein is a method for treating a disease or disorder associated with inhibition of KRAS interaction or a mutant thereof, in a patient in need thereof, comprising the step of administering to the patient a compound disclosed herein, or a pharmaceutically acceptable salt thereof, or a composition comprising a compound disclosed herein or a pharmaceutically acceptable salt thereof, in combination with another therapy or therapeutic agent as described herein.

In an embodiment, the disease or disorder is an immunological or inflammatory disorder. In another embodiment, the immunological or inflammatory disorder is Ras-associated lymphoproliferative disorder and juvenile myelomonocytic leukemia caused by somatic mutations of KRAS.

In an embodiment, the cancer is selected from hematological cancers, sarcomas, lung cancers, gastrointestinal cancers, genitourinary tract cancers, liver cancers, bone cancers, nervous system cancers, gynecological cancers, and skin cancers.

In another embodiment, the cancer is selected from carcinomas, hematological cancers, sarcomas, and glioblastoma.

In yet another embodiment, the hematological cancer is selected from myeloproliferative neoplasms, myelodysplastic syndrome, chronic and juvenile myelomonocytic leukemia, acute myeloid leukemia, acute lymphocytic leukemia, and multiple myeloma.

In still another embodiment, the carcinoma is selected from pancreatic, colorectal, lung, bladder, gastric, esophageal, breast, head and neck, cervical, skin, and thyroid.

In another embodiment, the lung cancer is selected from non-small cell lung cancer (NSCLC), small cell lung cancer, bronchogenic carcinoma, squamous cell bronchogenic carcinoma, undifferentiated small cell bronchogenic carcinoma, undifferentiated large cell bronchogenic carcinoma, adenocarcinoma, bronchogenic carcinoma, alveolar carcinoma, bronchiolar carcinoma, bronchial adenoma, chondromatous hamartoma, mesothelioma, pavicellular and non-pavicellular carcinoma, bronchial adenoma, and pleuropulmonary blastoma.

In yet another embodiment, the lung cancer is non-small cell lung cancer (NSCLC). In still another embodiment, the lung cancer is adenocarcinoma.

In an embodiment, the gastrointestinal cancer is selected from esophagus squamous cell carcinoma, esophagus adenocarcinoma, esophagus leiomyosarcoma, esophagus lymphoma, stomach carcinoma, stomach lymphoma, stomach leiomyosarcoma, exocrine pancreatic carcinoma, pancreatic ductal adenocarcinoma, pancreatic insulinoma, pancreatic glucagonoma, pancreatic gastrinoma, pancreatic carcinoid tumors, pancreatic vipoma, small bowel adenocarcinoma, small bowel lymphoma, small bowel carcinoid tumors, Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma, colorectal cancer, gall bladder cancer, and anal cancer.

In an embodiment, the gastrointestinal cancer is colorectal cancer.

In another embodiment, the cancer is a carcinoma. In yet another embodiment, the carcinoma is selected from pancreatic carcinoma, colorectal carcinoma, lung carcinoma, bladder carcinoma, gastric carcinoma, esophageal carcinoma, breast carcinoma, head and neck carcinoma, cervical skin carcinoma, and thyroid carcinoma.

In still another embodiment, the cancer is a hematopoietic malignancy. In an embodiment, the hematopoietic malignancy is selected from multiple myeloma, acute myelogenous leukemia, and myeloproliferative neoplasms.

In another embodiment, the cancer is a neoplasm. In yet another embodiment, the neoplasm is glioblastoma or sarcomas.

In certain embodiments, the disclosure provides a method for treating a KRAS-mediated disorder in a patient in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), 8p11 myeloproliferative syndrome, myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pretumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" KRAS with a compound described herein includes the administration of a compound described herein to an individual or patient, such as a human, having KRAS, as well as, for example, introducing a compound described herein into a sample containing a cellular or purified preparation containing KRAS.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapies

I. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, and CDK4/6 kinase inhibitors such as, for example, those described in WO 2006/056399 can be used in combination with the compounds of the present disclosure for treatment of CDK2- associated diseases, disorders or conditions. Other agents such as therapeutic antibodies can be used in combination with the compounds of the present disclosure for treatment of CDK2-associated diseases, disorders or conditions. The one or more additional pharmaceutical agents can be administered to a patient simultaneously or sequentially.

In some embodiments, the CDK2 inhibitor is administered or used in combination with a BCL2 inhibitor or a CDK4/6 inhibitor.

The compounds as disclosed herein can be used in combination with one or more other enzyme/protein/receptor inhibitors therapies for the treatment of diseases, such as cancer and other diseases or disorders described herein. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK4/6, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCB54828), INCB62079), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2; e.g., ruxolitinib or baricitinib; or JAK1; e.g., itacitinib (INCB39110), INCB052793, or INCB054707), an IDO inhibitor (e.g., epacadostat, NLG919, or BMS-986205, MK7162), an LSD1 inhibitor (e.g., GSK2979552, INCB59872 and INCB60003), a TDO inhibitor, a PI3K-delta inhibitor (e.g., parsaclisib (INCB50465) or INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer; e.g., INCB081776), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptosar, topotecan, paclitaxel, docetaxel, epothilones, tamoxifen, 5-fluorouracil, methotrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, SmI1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-1 agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteasome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, B1853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a CDK2 inhibitor of the present disclosure with an additional agent.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections. In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

II. Immune-Checkpoint Therapies

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (1B1308), AB122 (GLS-010), AMP-224, AMP-514/MEDI-0680, BMS936559, JTX-4014, BGB-108, SHR-1210, MEDI4736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217, 149, or 10,308,644; U.S. Publ. Nos. 2017/0145025, 2017/0174671, 2017/0174679, 2017/0320875, 2017/0342060, 2017/0362253, 2018/0016260, 2018/0057486, 2018/0177784, 2018/0177870, 2018/0179179, 2018/0179201, 2018/0179202, 2018/0273519, 2019/0040082, 2019/0062345, 2019/0071439, 2019/0127467, 2019/0144439, 2019/0202824, 2019/0225601, 2019/0300524, or 2019/0345170; or PCT Pub. Nos. WO 03042402, WO 2008156712, WO 2010089411, WO 2010036959, WO 2011066342, WO 2011159877, WO 2011082400, or WO 2011161699, which are each incorporated herein by reference in their entirety. In some embodiments, the inhibitor of PD-L1 is INCB086550.

In some embodiments, the PD-L1 inhibitor is selected from the compounds in Table A, or a pharmaceutically acceptable salt thereof.

TABLE A

| Cmpd No. | US Publication Appl. No. | Name and Structure |
|---|---|---|
| 1 | US 2018-0179197, Example #24 | (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid 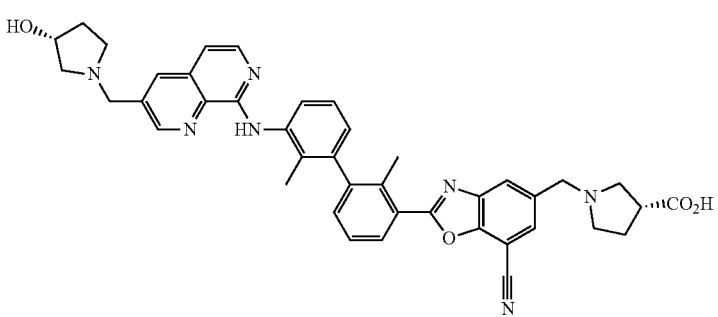 [SMILES: Cc1c(Nc2nccc3cc(CN4CC[C@@H](O)C4)cnc23)cccc1-c1cccc(-c2nc3cc(CN4CC[C@@H](C(=O)O)C4)cc(C#N)c3o2)c1C] |
| 2 | US 2018-0179201, Example #2 | N-(2-chloro-3'-(8-chloro-6-((2-hydroxyethylamino)methyl)-[1,2,4]triazolo[1,5-a]pyridin-2-yl)-2'-methylbiphenyl-3-yl)-5-((2-hydroxyethylamino)methyl)picolinamide 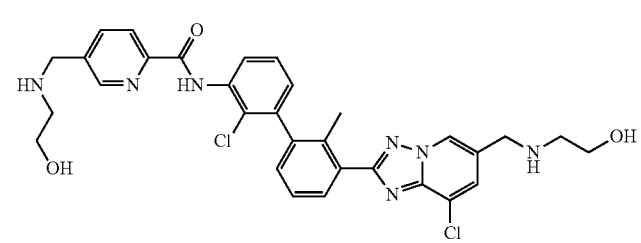 [SMILES: Cc1c(-c2nc3c(Cl)cc(CNCCO)cn3n2)cccc1-c1cccc(NC(=O)c2ccc(CNCCO)cn2)c1Cl] |
| 3 | US 2018-0179197, Example #25 | (S)-1-((7-cyano-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid 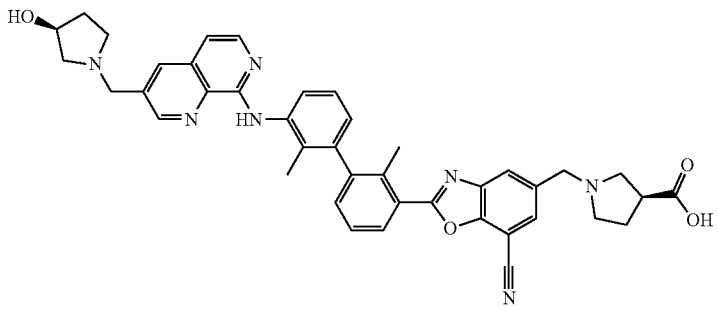 [SMILES: Cc1c(Nc2nccc3cc(CN4CC[C@H](O)C4)cnc23)cccc1-c1cccc(-c2nc3cc(CN4CC[C@H](C(=O)O)C4)cc(C#N)c3o2)c1C] |
| 4 | US 2018-0179197, Example #26 | (R)-1-((7-cyano-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid 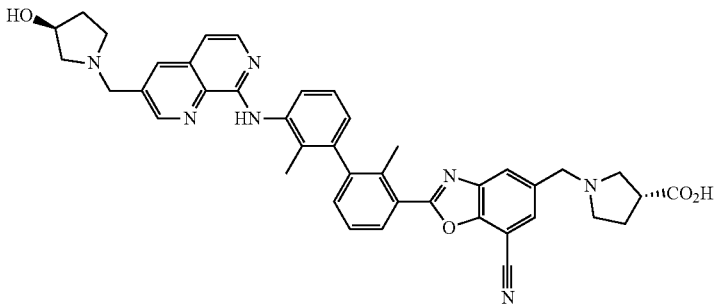 |

TABLE A-continued

| Cmpd No. | US Publication Appl. No. | Name and Structure |
|---|---|---|
| 5 | US 2018-0179197, Example #28 | (S)-1-((7-cyano-2-(3'-(3-(((R)-3-hydroxypyrrcolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid 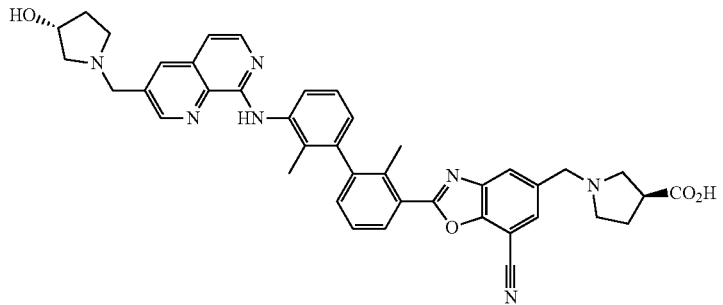 [SMILES: Cc1c(Nc2nccc3cc(CN4CC[C@@H](O)C4)cnc23)cccc1-c1cccc(-c2nc3cc(CN4CC[C@H](C(=O)O)C4)cc(C#N)c3o2)c1C] |
| 6 | US 2018-0179197, Example #236 | 1-((7-cyano-2-(3'-(5-(2-(dimethylamino)acetyl)-5,6-dihydro-4H-pyrrolo[3,4-d]thiazol-2-yl)-2,2'-dimethylbiphenyl-3-yl)benzo[d]oxazol-5-yl)methyl)piperidine-4-carboxylic acid 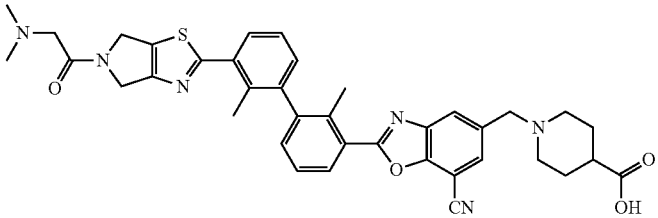 [SMILES: Cc1c(-c2nc3cc(CN4CCC(C(=O)O)CC4)cc(C#N)c3o2)cccc1-c1cccc(-c2nc3c(s2)CN(C(=O)CN(C)C)C3)c1C] |
| 7 | US 2018-0179179, Example #1 | N,N'-(2-chloro-2'-methylbiphenyl-3,3'-diyl)bis(5-((2-hydroxyethylamino) methyl)picolinamide) 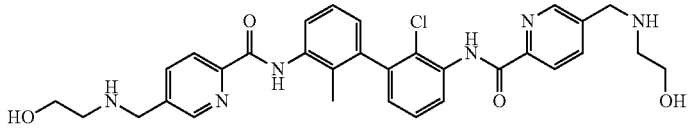 [SMILES: Cc1c(NC(=O)c2ccc(CNCCO)cn2)cccc1-c1cccc(NC(=O)c2ccc(CNCCO)cn2)c1Cl] |
| 8 | US 2018-0179179, Example #9 | (R)-1-((6-(2'-chloro-3'-(5-((3-hydroxypyrrolidin-1-yl)methyl)picolinamido)-2-methylbiphenyl-3-ylcarbamoyl)pyridin-3-yl)methyl)piperidine-4-carboxylic acid 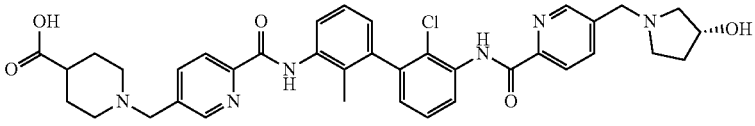 [SMILES: Cc1c(NC(=O)c2ccc(CN3CCC(C(=O)O)CC3)cn2)cccc1-c1cccc(NC(=O)c2ccc(CN3CC[C@@H](O)C3)cn2)c1Cl] |
| 9 | US 2018-0179179, Example #12 | (S)-1-((6-((2'-chloro-2-methyl-3'-(5-(pyrrolidin-1-ylmethyl)picolinamido)-[1,1'-biphenyl]-3-yl)carbamoyl)-4-methylpyridin-3-yl)methyl)piperidine-2-carboxylic acid 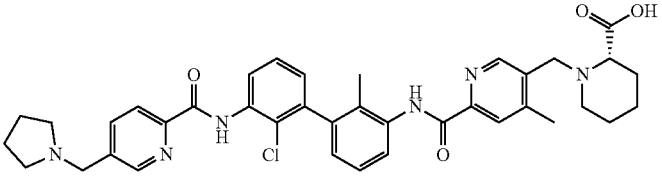 [SMILES: Cc1cc(C(=O)Nc2cccc(-c3cccc(NC(=O)c4ccc(CN5CCCC5)cn4)c3Cl)c2C)ncc1CN1CCCC[C@H]1C(=O)O] |

TABLE A-continued

| Cmpd No. | US Publication Appl. No. | Name and Structure |
|---|---|---|
| 10 | US 2018-0179202, Example #52 | trans 4-(2-(2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl)cyclohexanecarboxylic acid |
| 11 | US 2018-0179202, Example #56 | cis-4-((2-(2-chloro-3'-(3-(((R)-3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid |
| 12 | US 2018-0179202, Example #68 | (R)-4-(2-(2-chloro-3'-(7-((3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridin-5(4H)-yl)-1-methylcyclohexanecarboxylic acid |
| 13 | US 2018-0179202, Example #90 | (R)-1-((8-((2-chloro-3'-(5-(N-ethyl-N-methylglycyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid |

TABLE A-continued

| Cmpd No. | US Publication Appl. No. | Name and Structure |
|---|---|---|
| 14 | US 2018-0177784, Example #35 | (R)-2-(dimethylamino)-1-(2-(3'-(5-(2-(3-hydroxypyrrolidin-1-yl)acetyl)-5,6-dihydro-4H-pyrrolo[3,4-d]thiazol-2-yl)-2,2'-dimethylbiphenyl-3-yl)-4H-pyrrolo[3,4-d]thiazol-5(6H)-yl)ethanone |
| 15 | US 2018-0177870, Example #37 | trans-4-((2-(2'-chloro-3'-(1,5-dimethyl-4,5,6,7-tetrahydro-1H-imidazo[4,5-c]pyridine-2-carboxamido)-2-methylbiphenyl-3-ylcarbamoyl)-1-methyl-6,7-dihydro-1H-imidazo[4,5-c]pyridin-5(4H)-yl)methyl)cyclohexane-1-carboxylic acid |
| 16 | US 2018-0177870, Example #100 | trans-4-(2-(2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid |
| 17 | US 2018-0177870, Example #114 | cis-4-((2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid |

TABLE A-continued

| Cmpd No. | US Publication Appl. No. | Name and Structure |
|---|---|---|
| 18 | US 2018-0177870, Example #135 | cis-4-((2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid |
| 19 | US 2018-0177870, Example #148 | trans-4-(2-(2-((2'-chloro-2-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid |
| 20 | US 2018-0177870, Example #159 | trans-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid |

TABLE A-continued

| Cmpd No. | US Publication Appl. No. | Name and Structure |
|---|---|---|
| 21 | US 2018-0177870, Example #160 | cis-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid 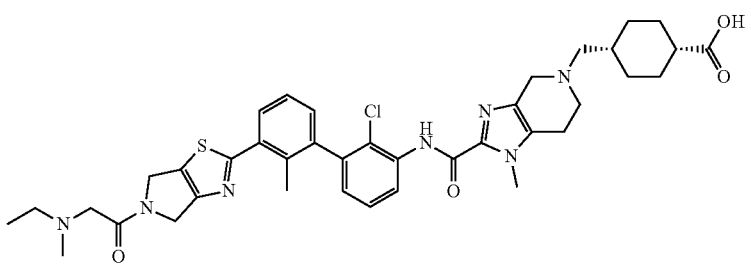 [SMILES: CCN(C)CC(=O)N1Cc2nc(-c3cccc(-c4cccc(NC(=O)c5nc6c(n5C)CCN(C[C@H]5CC[C@@H](C(=O)O)CC5)C6)c4Cl)c3C)sc2C1] |
| 22 | US 2018-0177870, Example #161 | 4-(2-(2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid 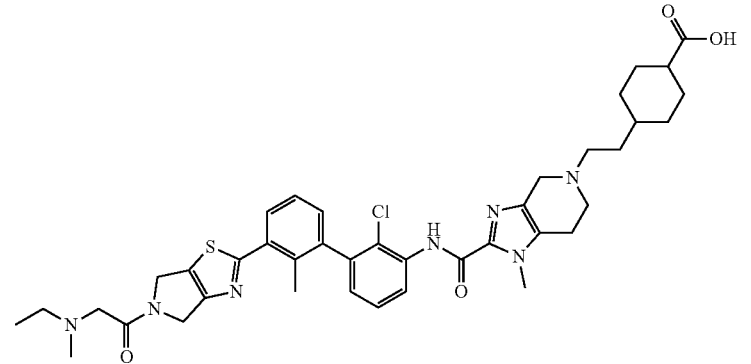 [SMILES: CCN(C)CC(=O)N1Cc2nc(-c3cccc(-c4cccc(NC(=O)c5nc6c(n5C)CCN(CCC5CCC(C(=O)O)CC5)C6)c4Cl)c3C)sc2C1] |
| 23 | US 2018-0177870, Example #162 | 4-(2-(2-(2-chloro-3'-(5-(2-(isopropyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid 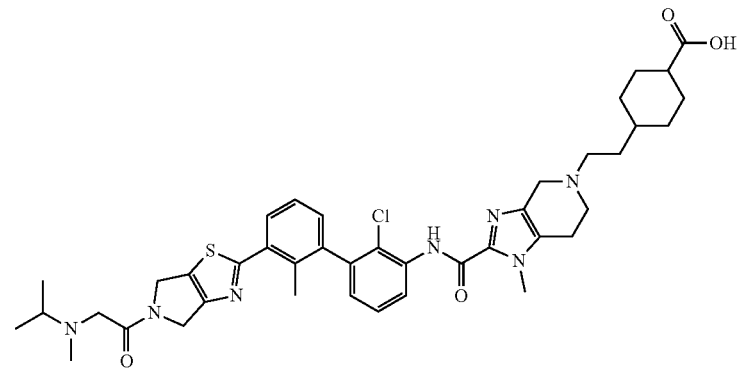 [SMILES: Cc1c(-c2nc3c(s2)CN(C(=O)CN(C)C(C)C)C3)cccc1-c1cccc(NC(=O)c2nc3c(n2C)CCN(CCC2CCC(C(=O)O)CC2)C3)c1Cl] |

TABLE A-continued

| Cmpd No. | US Publication Appl. No. | Name and Structure |
|---|---|---|
| 24 | US 2019-0300524, Example #16 | (R)-1-((7-cyano-2-(3'-(2-(difluoromethyl)-7-((3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylic acid |
| 25 | US 2019-0300524, Example #17 | (R)-1-((7-cyano-2-(3'-(2-(difluoromethyl)-7-(((R)-3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)pyrrolidine-3-carboxylic acid |
| 26 | US 2019-0300524, Example #18 | (R)-1-((7-cyano-2-(3'-(2-(difluoromethyl)-7-(((R)-3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)-3-methylpyrrolidine-3-carboxylic acid |
| 27 | US 2019-0300524, Example #30 | (R)-1-((7-cyano-2-(3'-(2-(difluoromethyl)-7-((3-hydroxy-3-methylpyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylic acid |
| 28 | US 2019-0300524, Example #31 | (S)-1-((7-cyano-2-(3'-(2-(difluoromethyl)-7-((3-hydroxy-3-methylpyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylic acid |

TABLE A-continued

| Cmpd No. | US Publication Appl. No. | Name and Structure |
|---|---|---|
| 29 | US 2019-0345170, Example #13 | (R)-4-(2-(2-((2,2'-dichloro-3'-(5-(2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid 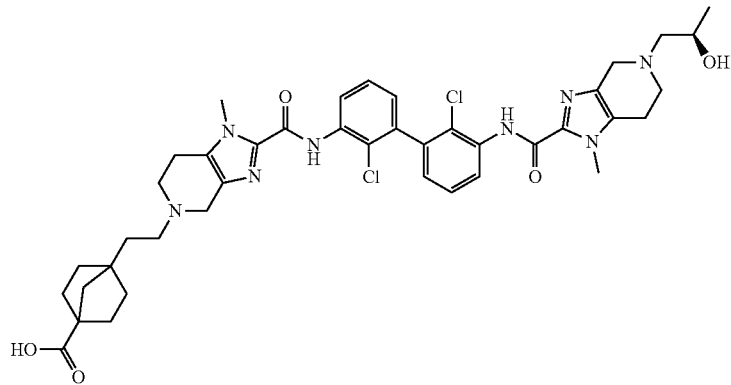 [SMILES: C[C@@H](O)CN1CCc2c(nc(C(=O)Nc3cccc(-c4cccc(NC(=O)c5nc6c(n5C)CCN(CCC57CCC(C(=O)O)(CC5)C7)C6)c4Cl)c3Cl)n2C)C1] |
| 30 | US 2019-0345170, Example #17 | 4,4'-(((((2,2'-dichloro-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) 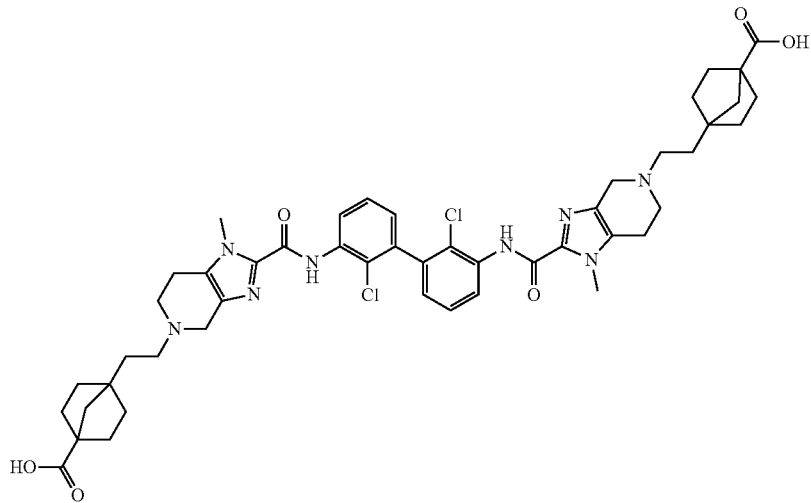 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCC13CCC(C(=O)O)(CC1)C3)C2] |

TABLE A-continued

| Cmpd No. | US Publication Appl. No. | Name and Structure |
|---|---|---|
| 31 | US 2019-0345170, Example #18 | 4-((2-((3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid |

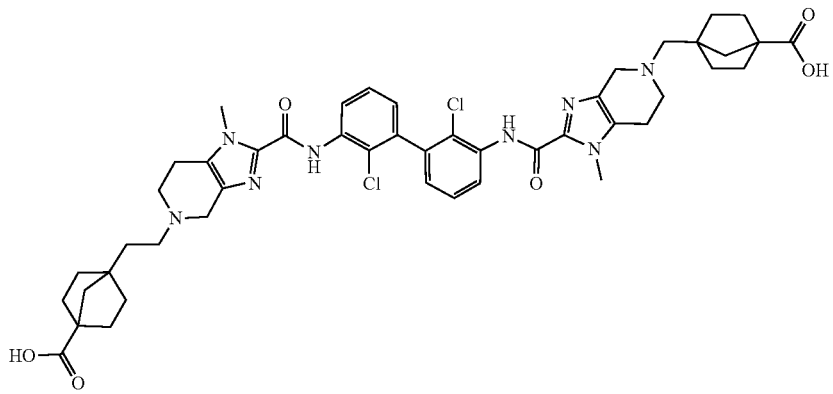 [SMILES: Cn1c(C(=O)Nc2cccc(-c3cccc(NC(=O)c4nc5c(n4C)CCN(CC46CCC(C(=O)O)(CC4)C6)C5)c3Cl)c2Cl)nc2c1CCN(CCC13CCC(C(=O)O)(CC1)C3)C2]

| 32 | US 2019-0345170, Example #34 | 4,4'-(((((2-chloro-2'-methyl-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) |

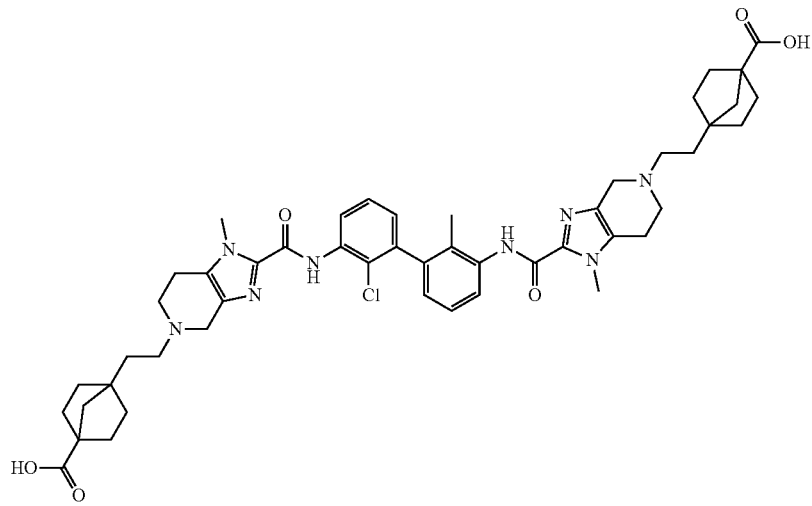 [SMILES: Cc1c(NC(=O)c2nc3c(n2C)CCN(CCC24CCC(C(=O)O)(CC2)C4)C3)cccc1-c1cccc(NC(=O)c2nc3c(n2C)CCN(CCC24CCC(C(=O)O)(CC2)C4)C3)c1Cl]

TABLE A-continued

| Cmpd No. | US Publication Appl. No. | Name and Structure |
|---|---|---|
| 33 | US 2019-0345170, Example #51 | 4,4'-(((((2-chloro-2'-cyano-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) |

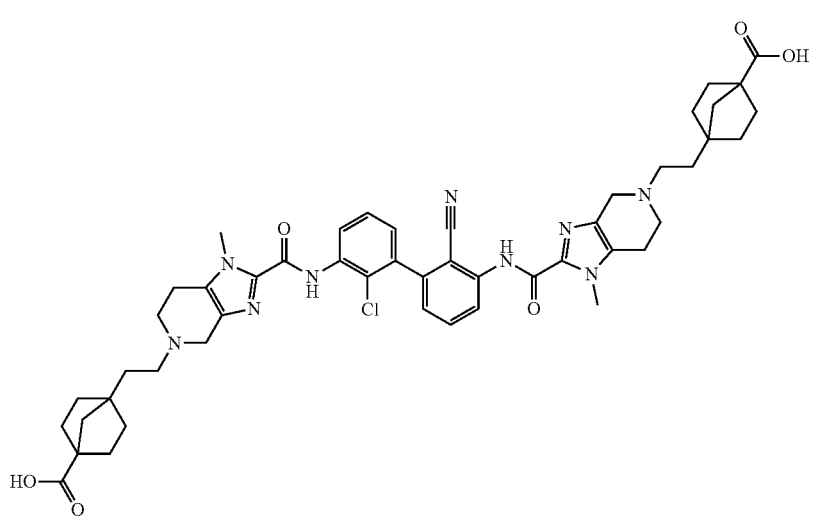 [SMILES: Cn1c(C(=O)Nc2cccc(-c3cccc(NC(=O)c4nc5c(n4C)CCN(CCC46CCC(C(=O)O)(CC4)C6)C5)c3C#N)c2Cl)nc2c1CCN(CCC13CCC(C(=O)O)(CC1)C3)C2]

| 34 | US 2021-0094976, Example #1 | (R)-4-(2-(2-((2-chloro-3'-((2-(difluoromethyl)-7-((3-hydroxypyrrolidin-1-yl)methyl)pyrido[3,2-d]pyrimidin-4-yl)amino)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

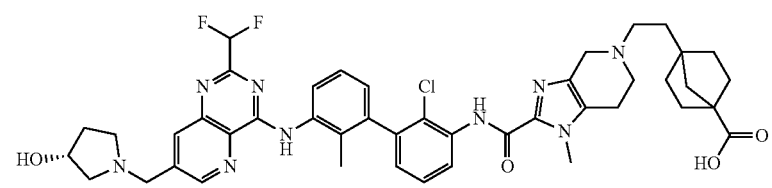 [SMILES: Cc1c(Nc2nc(C(F)F)nc3cc(CN4CC[C@@H](O)C4)cnc23)cccc1-c1cccc(NC(=O)c2nc3c(n2C)CCN(CCC24CCC(C(=O)O)(CC2)C4)C3)c1Cl]

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD-1 monoclonal antibody is MGA012 (IN-CMGA0012; retifanlimab). In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9. In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MED11873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MED10562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, R07009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

Formulation, Dosage Forms and Administration

When employed as pharmaceuticals, the compounds of the present disclosure can be administered in the form of pharmaceutical compositions. Thus, the present disclosure provides a composition comprising a compound of Formula I, II, or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating KRAS protein in tissue samples, including human, and for identifying KRAS ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes KRAS binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a C$_{16}$ alkyl group of Formula I, II, or any formulae provided herein can be optionally substituted with deuterium atoms, such as —CD$_3$ being substituted for —CH$_3$). In some embodiments, alkyl groups in Formula I, II, or any formulae provided herein can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. J. *Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^3$H, $^{14}$C, $^{82}$Br, $^{125}$I, $^{131}$I or $^{31}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from $^3$H, $^{14}$C, $^{121}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a KRAS protein by monitoring its concentration variation when contacting with the KRAS, through tracking of the labeling. For example, a test compound (labeled) can be evaluated for its ability to reduce binding of another compound which is known to bind to a KRAS protein (i.e., standard compound). Accordingly, the ability of a test compound to compete with the standard compound for binding to the KRAS protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of KRAS, such as cancer or infections, which include one or more containers containing a pharmaceutical composition comprising a therapeutically effective amount of a compound of Formula I, II, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of KRAS according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check.

The compounds separated were typically subjected to analytical liquid chromatography mass spectrometry (LCMS) for purity check under the following conditions: Instrument; Agilent 1100 series, LC/MSD, Column: Waters Sunfire™ C18 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ C18 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters XBridge C18 5 μm particle size, 19×100 mm column, eluting with mobile phase A: 0.15% NH₄OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute."

The following abbreviations may be used herein: AcOH (acetic acid); Ac₂O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N, N'diisopropyl azidodicarboxylate); DIEA (N,N-diisopropylethylamine); DIPEA (N, N-diisopropylethylamine); DIBAL (diisobutylaluminium hydride); DMF (N, N-dimethylformamide); Et (ethyl); EtOAc (ethyl acetate); FCC (flash column chromatography); g (gram(s)); h (hour(s)); HATU (N, N, N', N'tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography—mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); NCS (N-chlorosuccinimide); NEt₃ (triethylamine); nM (nanomolar); NMP (N-methylpyrrolidinone); NMR (nuclear magnetic resonance spectroscopy); OTf (trifluoromethanesulfonate); Ph (phenyl); pM (picomolar); PPT(precipitate); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); pg (microgram(s)); μL (microliter(s)); μM (micromolar); wt % (weight percent). Brine is saturated aqueous sodium chloride. In vacuo is under vacuum.

Example 1a and Example 1b. 1-(1-((2S,4S)-1-(but-2-ynoyl)-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile

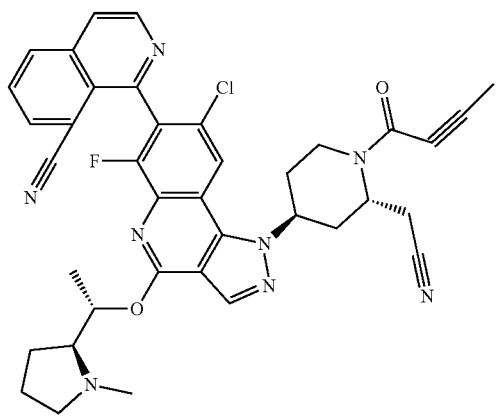 [SMILES: CC#CC(=O)N1CC[C@H](n2ncc3c(O[C@@H](C)[C@@H]4CCCN4C)nc4c(F)c(-c5nccc6cccc(C#N)c56)c(Cl)cc4c32)C[C@H]1CC#N]

Step 1. ethyl 2-amino-4-bromo-3-fluorobenzoate

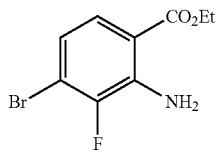

To a solution of 2-amino-4-bromo-3-fluorobenzoic acid (22.7 g, 92 mmol) in ethanol (184 ml) was added sulfuric acid (9.82 ml, 184 mmol) slowly. The resulting mixture was heated to reflux for 2 days. After cooling to rt, the reaction mixture was diluted with water and adjusted pH to 7 with 6 M NaOH (22 mL). The organic solvent was removed in vacuo. The resulting mixture was diluted with ethyl acetate and water. The organic layer was washed with 0.5 N NaOH solution, brine, dried over $Na_2SO_4$, filtered and concentrated under vacuum to give the desired product (23.2 g, 96%). LCMS calculated for $C_9H_{10}BrFNO_2$ $(M+H)^+$ m/z=262.0, 264.0; found 262.0, 264.0.

Step 2. ethyl 2-amino-3-fluoro-4-(4,4,5,5-tetramethyl-1,3,2-dioxaborolan-2-yl)benzoate

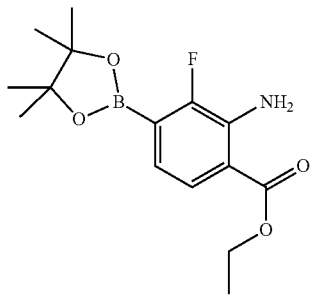 [SMILES: CCOC(=O)c1ccc(B2OC(C)(C)C(C)(C)O2)c(F)c1N]

A mixture of ethyl 2-amino-4-bromo-3-fluorobenzoate (21.8 g, 83 mmol), Bis(pinacolato)diboron (25.3 g, 100 mmol), dichloro[1,1'-bis(diphenylphosphino)ferrocene]palladium (II) dichloromethane adduct (6.79 g, 8.32 mmol) and acetic acid, potassium salt, anhydrous (17.96 g, 183 mmol) and dioxane (416 ml) was stirred at 100° C. under nitrogen atmosphere for 5 h. The crude was filtered through Celite and washed with ethyl acetate. The filtrate was concentrated. The residue was purified with flash chromatography to give the desired product (24 g, 93%). LCMS calculated for $C_{15}H_{22}BFNO_4$ $(M+H)^+$ m/z=310.2; found 310.1.

Step 3. 8-cyanoisoquinoline 2-oxide

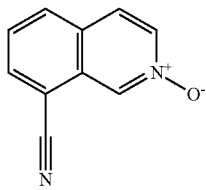 [SMILES: N#Cc1cccc2cc[n+]([O-])cc12]

To a solution of isoquinoline-8-carbonitrile (3.70 g, 24.00 mmol) in $CH_2Cl_2$ (240 ml) was added m-CPBA (7.10 g, 28.8 mmol) at 0° C. The reaction mixture was stirred at 0° C. for 2 h. The reaction mixture was diluted with sat $NaHCO_3$ solution. The aqueous layer was extracted with DCM (3×). The combined organic layers were dried over $Na_2SO_4$, filtered and concentrated. The crude was purified with flash chromatography (eluting with a gradient 0-100% ethyl acetate in hexanes) to give the desired product (3.2 g, 78%). LC-MS calculated for $C_{10}H_7N_2O$ $(M+H)^+$: m/z=171.1; found 171.1.

Step 4. 1-chloroisoquinoline-8-carbonitrile

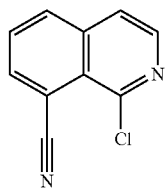 [SMILES: N#Cc1cccc2ccnc(Cl)c12]

To a solution of 8-cyanoisoquinoline 2-oxide (5.30 g, 31.1 mmol), 2,6-lutidine (7.26 ml, 62.3 mmol) in $CH_2Cl_2$ (62.3 ml) was added $POCl_3$ (5.81 ml, 62.3 mmol). The reaction mixture was stirred at room temperature for 2 h. The reaction mixture was quenched with addition of saturated $NaHCO_3$ (80 mL). The organic layer was dried with MgSO4 and concentrated to give a crude product. The crude product was triturated with ethyl acetate in hexanes to give the desired product as white solid (4.0 g, 68%). LC-MS calculated for $C_{10}H_6ClN_2$ $(M+H)^+$: m/z=189.0; found 189.0.

Step 5. ethyl 2-amino-4-(8-cyanoisoquinolin-1-yl)-3-fluorobenzoate

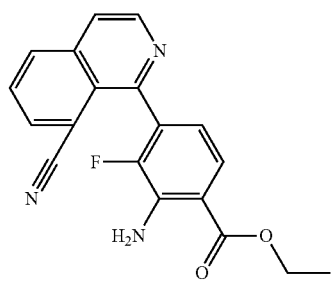 [SMILES: CCOC(=O)c1ccc(-c2nccc3cccc(C#N)c23)c(F)c1N]

A mixture of 1-chloroisoquinoline-8-carbonitrile (6.60 g, 35.0 mmol), ethyl 2-amino-3-fluoro-4-(4,4,5,5-tetramethyl-1,3,2-dioxaborolan-2-yl)benzoate (11.36 g, 36.7 mmol), SPhos Pd G4 (1.390 g, 1.750 mmol) and tripotassium phosphate hydrate (17.73 g, 77 mmol) in 1,4-dioxane (120 mL) and water (24 mL) was stirred at 80° C. for 2 h. The solution was diluted with ethyl acetate and water. The organic layer was concentrated. The crude was used in the next step without purification. LC-MS calculated for $C_{19}H_{15}FN_3O_2$ $(M+H)^+$: m/z=336.1; found 336.1.

Step 6. ethyl 2-amino-5-chloro-4-(8-cyanoisoquinolin-1-yl)-3-fluorobenzoate

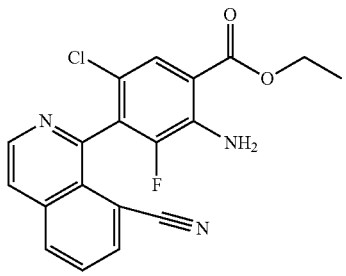 [SMILES: CCOC(=O)c1cc(Cl)c(-c2nccc3cccc(C#N)c23)c(F)c1N]

To a solution of ethyl 2-amino-4-(8-cyanoisoquinolin-1-yl)-3-fluorobenzoate (11.7 g, 34.9 mmol) in DMF (116 ml) was added NCS (5.12 g, 38.4 mmol) at rt. The mixture was heated at 80° C. for 15 h. The reaction mixture was cooled to rt and diluted with water. The precipitate was collected with filtration and washed with water and ethyl acetate/hexane (1:2). The filtrate was extracted with ethyl acetate. The organic layer was concentrated. The solid was collected with filtration and washed ethyl acetate/hexane (1:2) to give the desired product (10.2 g, 79%). LC-MS calculated for $C_{19}H_{14}ClFN_3O_2(M+H)^+$: m/z=370.1; found 370.1.

Step 7. ethyl 5-chloro-4-(8-cyanoisoquinolin-1-yl)-2-(3-ethoxy-3-oxopropanamido)-3-fluorobenzoate

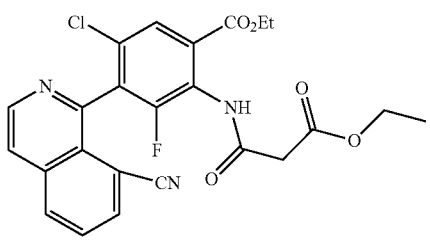 [SMILES: CCOC(=O)CC(=O)Nc1c(C(=O)OCC)cc(Cl)c(-c2nccc3cccc(C#N)c23)c1F]

To a solution of ethyl 2-amino-5-chloro-4-(8-cyanoisoquinolin-1-yl)-3-fluorobenzoate (10.3 g, 27.9 mmol) and TEA (5.05 ml, 36.2 mmol) in DCM (280 mL) was added ethyl 3-chloro-3-oxopropanoate (3.92 ml, 30.6 mmol) dropwise at 0° C. The resulting mixture was stirred at 0° C. and monitored by LC-MS. another equivalent of ethyl 3-chloro-3-oxopropanoate (3.92 ml, 30.6 mmol) was added dropwise and stirred for 1 h. The reaction was diluted with water and DCM. The organic layer was separated and dried over $Na_2SO_4$, filtered and concentrated. The residue was purified with flash chromatography to give the desired product (9.5 g, 70%). LC-MS calculated for $C_{24}H_{20}ClFN_3O_5(M+H)^+$: m/z=484.1; found 484.1.

Step 8. ethyl 6-chloro-7-(8-cyanoisoquinolin-1-yl)-8-fluoro-2,4-dihydroxyquinoline-3-carboxylate

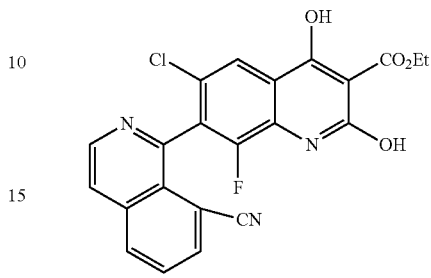

A solution of 21% sodium ethoxide (19.91 ml, 53.3 mmol) in EtOH was added dropwise to a solution of ethyl 5-chloro-4-(8-cyanoisoquinolin-1-yl)-2-(3-ethoxy-3-oxopropanamido)-3-fluorobenzoate (8.6 g, 17.77 mmol) in EtOH (80 ml). The resulting mixture was stirred at rt for 2 h. To the reaction flask was added 1 N HCl to adjust pH to 3. The solvent was removed under vacuum. The resulting precipitate was collected and washed with ethyl acetate to give the desired product as white solid (7.4 g, 95%). LC-MS calculated for $C_{22}H_{14}ClFN_3O_4(M+H)^+$: m/z=438.1; found 438.1.

Step 9. ethyl 6-chloro-7-(8-cyanoisoquinolin-1-yl)-8-fluoro-2,4-dihydroxyquinoline-3-carboxylate

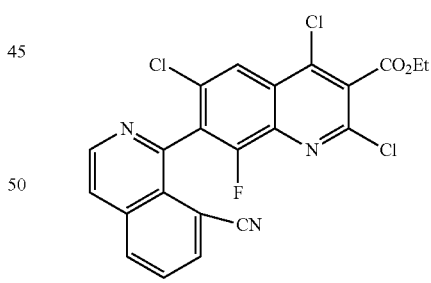

To reaction flask was added ethyl 6-chloro-7-(8-cyanoisoquinolin-1-yl)-8-fluoro-2,4-dihydroxyquinoline-3-carboxylate (7.4 g, 16.90 mmol) and $POCl_3$ (31.5 ml, 338 mmol), The resulting mixture was stirred at 110° C. for 2 h. $POCl_3$ was removed by azeotrope with toluene (3 times), and the residue was diluted with DCM and saturated $NaHCO_3$ solution. The organic layer was separated and dried over Na2SO4, filtered and concentrated. The crude was triturated with ethyl acetate/hexane (1:1) to give the desired product as white solid (7.24 g, 90%). LC-MS calculated for $C_{22}H_{12}Cl_3FN_3O_2(M+H)^+$: m/z=474.0, 476.0; found 474.0, 476.0.

Step 10. ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanoisoquinolin-1-yl)-8-fluoroquinoline-3-carboxylate

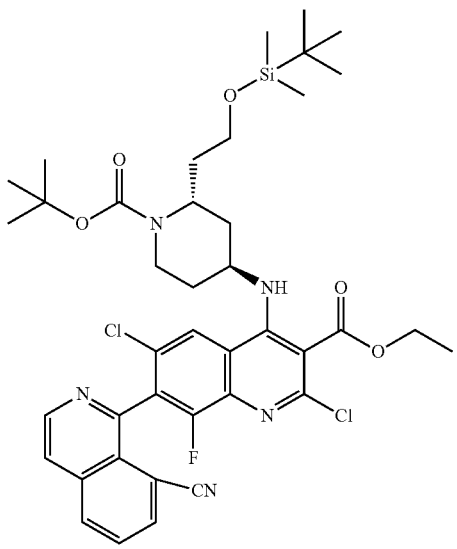

To a solution of ethyl 2,4,6-trichloro-7-(8-cyanoisoquinolin-1-yl)-8-fluoroquinoline-3-carboxylate (7.24 g, 15.25 mmol) in DMF (100 ml) was added tert-butyl (2S,4S)-4-amino-2-(2-((tert-butyldimethylsilyl)oxy)ethyl)piperidine-1-carboxylate (6.56 g, 18.30 mmol) and DIEA (5.3 ml, 30.5 mmol). The resulting mixture was stirred at 65° C. overnight. The reaction mixture was diluted with ethyl acetate and water. The organic layer was washed with water and brine, dried over Na$_2$SO$_4$, filtered and concentrated. The crude was purified with silica gel column (eluted with a gradient 0-30% ethyl acetate in hexanes) to give the desired product as light yellow foam (11.5 g, 95%). LC-MS calculated for C$_{40}$H$_{49}$Cl$_2$FN$_5$O$_5$Si (M+H)$^+$: m/z=796.3, 798.3; found 796.3, 798.3.

Step 11. tert-butyl (2S,4S)-2-(2-((tert-butyldimethylsilyl)oxy)ethyl)-4-((2,6-dichloro-7-(8-cyanoisoquinolin-1-yl)-8-fluoro-3-(hydroxymethyl)quinolin-4-yl)amino)piperidine-1-carboxylate

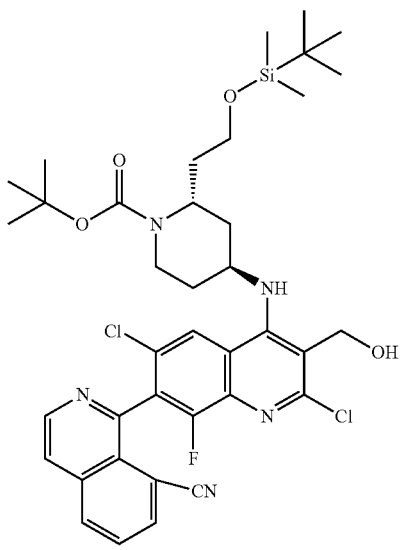

To a solution of ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanoisoquinolin-1-yl)-8-fluoroquinoline-3-carboxylate (2.45 g, 3.07 mmol) in Toluene (30.7 ml) at −78° C. was added 1.0 M DIBAL-H in DCM (9.84 ml, 9.84 mmol). The resulting mixture was allowed to warm to −20° C. over 2 h period, quenched with methanol (1.3 mL). Aqueous Rochelle salt (prepared from 14.7 g (6 wt) of Rochelle salt and 50 mL of water was added to the solution at ≤10° C. The biphasic mixture was stirred vigorously for ≥1 h at 15-25° C. and separated to give organic layer. The organic layer was dried over Na$_2$SO$_4$, filtered and concentrated. and used as is. LC-MS calculated for C$_{38}$H$_{47}$Cl$_2$FN$_5$O$_4$Si (M+H)$^+$: m/z=754.3, 756.3; found 754.3, 756.3.

Step 12. tert-butyl (2S,4S)-2-(2-((tert-butyldimethylsilyl)oxy)ethyl)-4-((2,6-dichloro-7-(8-cyanoisoquinolin-1-yl)-8-fluoro-3-formylquinolin-4-yl)amino)piperidine-1-carboxylate

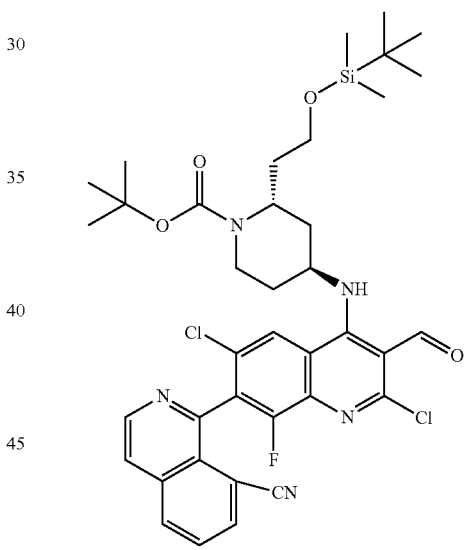

To a solution of tert-butyl (2S,4S)-2-(2-((tert-butyldimethylsilyl)oxy)ethyl)-4-((2,6-dichloro-7-(8-cyanoisoquinolin-1-yl)-8-fluoro-3-(hydroxymethyl)quinolin-4-yl)amino)piperidine-1-carboxylate (2.32 g, 3.07 mmol) in DCM (23 ml) and acetonitrile (7.7 ml) was added acetic acid (0.53 ml, 9.22 mmol) and IBX (2.58 g, 9.22 mmol). The resulting mixture was stirred at 38° C. for 22 h, To the reaction mixture was filtered and washed with DCM. The filtrate was concentrated and purified with silica gel column (eluted with a gradient 0-20% ethyl acetate in hexs) to give the desired products as two peaks.

Diastereomer 1 (1.05 g, 45%). Peak 1. LC-MS calculated for C$_{38}$H$_{45}$Cl$_2$FN$_5$O$_4$Si (M+H)$^+$: m/z=752.3, 754.3; found 752.3, 754.3.

Diastereomer 2 (1.05 g, 45%). Peak 2. LC-MS calculated for C$_{38}$H$_{45}$Cl$_2$FN$_5$O$_4$Si (M+H)$^+$: m/z=752.3, 754.3; found 752.3, 754.3.

Step 13. tert-butyl (2S,4S)-2-(2-((tert-butyldimethylsilyl)oxy)ethyl)-4-((2,6-dichloro-7-(8-cyanoisoquinolin-1-yl)-8-fluoro-3-((E)-(hydroxyimino)methyl)quinolin-4-yl)amino)piperidine-1-carboxylate

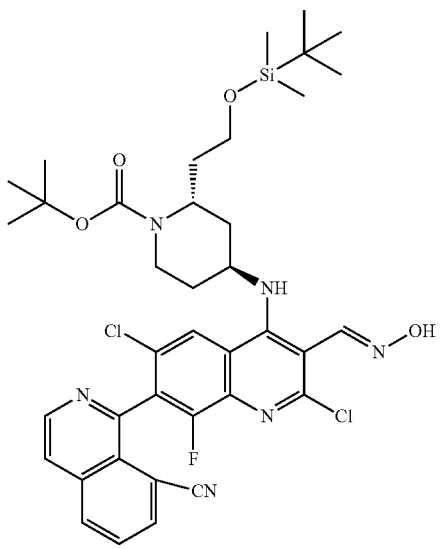

To a mixture of tert-butyl (2S,4S)-2-(2-((tert-butyldimethylsilyl)oxy)ethyl)-4-((2,6-dichloro-7-(8-cyanoisoquinolin-1-yl)-8-fluoro-3-formylquinolin-4-yl)amino)piperidine-1-carboxylate (0.85 g, 1.13 mmol) (peak 1 from last step), DCM (11 ml) and EtOH (11 ml) was added hydroxylamine hydrochloride (0.259 g, 3.73 mmol) and pyridine (0.30 ml, 3.73 mmol). The reaction mixture was stirred at 40° C. for 16 hours. The solvent was evaporated in vacuo. The residue with DCM and water. The aqueous layer was extracted with DCM. The combined organic layers were washed with aqueous $CuSO_4$, brine, dried over $MgSO_4$, filtered and concentrated in vacuo. The residue was purified with column chromatography on silica gel to give the desired product (0.5 g, 57%). LC-MS calculated for $C_{38}H_{46}Cl_2FN_6O_4Si$ (M+H)$^+$: m/z=767.3, 769.3; found 767.3, 769.3.

Diastereomer 2 was prepared in similar way as Diastereomer 1 using peak 2 from last step. LC-MS calculated for $C_{38}H_{46}Cl_2FN_6O_4Si$ (M+H)$^+$: m/z=767.3, 769.3; found 767.3, 769.3.

Step 14. tert-butyl (2S,4S)-2-(2-((tert-butyldimethylsilyl)oxy)ethyl)-4-(4,8-dichloro-7-(8-cyanoisoquinolin-1-yl)-6-fluoro-1H-pyrazolo[4,3-c]quinolin-1-yl)piperidine-1-carboxylate

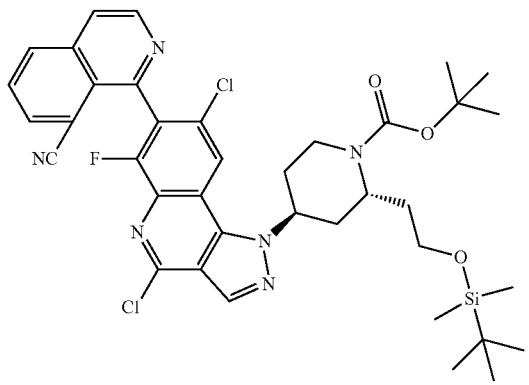 [SMILES: CC(C)(C)OC(=O)N1CC[C@H](n2ncc3c(Cl)nc4c(F)c(-c5nccc6cccc(C#N)c56)c(Cl)cc4c32)C[C@H]1CCO[Si](C)(C)C(C)(C)C]

To a solution of (tert-butyl (2S,4S)-2-(2-((tert-butyldimethylsilyl)oxy)ethyl)-4-((2,6-dichloro-7-(8-cyanoisoquinolin-1-yl)-8-fluoro-3-((E)-(hydroxyimino)methyl)quinolin-4-yl)amino)piperidine-1-carboxylate (486 mg, 0.633 mmol) (Diastereomer 1 from last step) in $CH_2Cl$ (5 mL) was added 2-aminopyridine (113 mg, 1.203 mmol) and Ms-Cl (84 μl, 1.076 mmol) at 0° C. The resulting mixture was stirred at 0° C. for 2 hours, then warmed to room temperature overnight. The reaction mixture was diluted with water. The organic layer was washed with brine, dried over $MgSO_4$, filtered and concentrated. and used as is. LC-MS calculated for $C_{38}H_{44}Cl_2FN_6O_3Si$ (M+H)$^+$: m/z=749.3, 751.3; found 749.3, 751.3.

Diastereomer 2 was prepared in similar way as Diastereomer 1 using peak 2 from last step. LC-MS calculated for $C_{38}H_{44}Cl_2FN_6O_3Si$ (M+H)$^+$: m/z=749.3, 751.3; found 749.3, 751.3.

Step 15 tert-butyl (2S,4S)-2-(2-((tert-butyldimethylsilyl)oxy)ethyl)-4-(8-chloro-7-(8-cyanoisoquinolin-1-yl)-6-fluoro-4-(methylthio)-1H-pyrazolo[4,3-c]quinolin-1-yl)piperidine-1-carboxylate

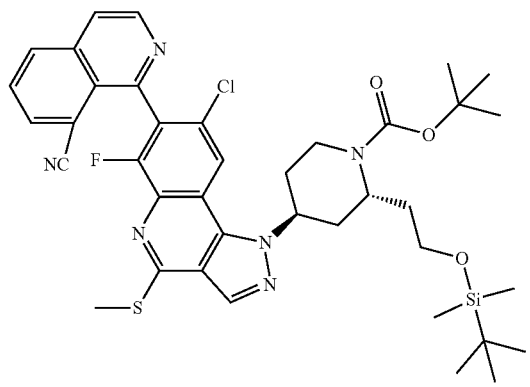 [SMILES: CSc1nc2c(F)c(-c3nccc4cccc(C#N)c34)c(Cl)cc2c2c1cnn2[C@H]1CCN(C(=O)OC(C)(C)C)[C@H](CCO[Si](C)(C)C(C)(C)C)C1]

Sodium thiomethoxide (133 mg, 1.901 mmol) was added to a mixture of tert-butyl (2S,4S)-2-(2-((tert-butyldimethylsilyl)oxy)ethyl)-4-(4,8-dichloro-7-(8-cyanoisoquinolin-1-yl)-6-fluoro-1H-pyrazolo[4,3-c]quinolin-1-yl)piperidine-1-carboxylate (475 mg, 0.634 mmol) (Diastereomer 1 from last step) in MeOH (6.3 ml)/1,4-dioxane (6.3 ml) was stirred at 90° C. for 18 h. The mixture was diluted with sat'd $NH_4Cl$ and extracted with EtOAc. The combined organic layers were dried over $MgSO_4$, filtered, concentrated, and used as is. LC-MS calculated for $C_{39}H_{47}ClFN_6O_3SSi$ (M+H)$^+$: m/z=761.3; found 761.3.

Diastereomer 2 was prepared in similar way as Diastereomer 1 using peak 2 from last step. LC-MS calculated for $C_{39}H_{47}ClFN_6O_3SSi$ (M+H)$^+$: m/z=761.3; found 761.3.

Step 16. tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(2-hydroxyethyl)piperidine-1-carboxylate

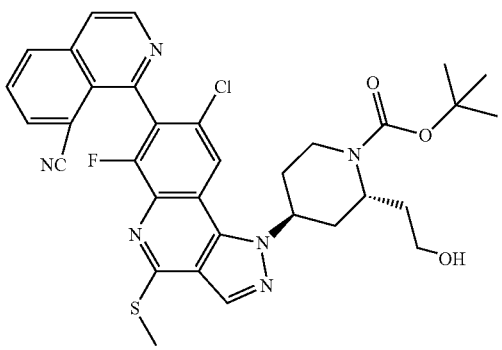 [SMILES: CSc1nc2c(F)c(-c3nccc4cccc(C#N)c34)c(Cl)cc2c2c1cnn2[C@H]1CCN(C(=O)OC(C)(C)C)[C@H](CCO)C1]

To a solution of tert-butyl (2S,4S)-2-(2-((tert-butyldimethylsilyl)oxy)ethyl)-4-(8-chloro-7-(8-cyanoisoquinolin-1-yl)-6-fluoro-4-(methylthio)-1H-pyrazolo[4,3-c]quinolin-1-yl)piperidine-1-carboxylate (482 mg, 0.633 mmol) (Diastereomer 1 from last step) in THF (6.33 ml) was added 1.0 M TBAF in THF (633 µl, 0.633 mmol). The resulting mixture was stirred at 60° C. for 1 h. After cooling to rt, the reaction mixture was diluted with water and ethyl acetate. The organic layer was separated and washed with brine, dried over Na$_2$SO$_4$, filtered and concentrated. The residue was purified with flash chromatography to give the desired product (0.39 g, 95%). LC-MS calculated for C$_{33}$H$_{33}$ClFN$_6$O$_3$S (M+H)$^+$: m/z=647.2; found 647.2.

Diastereomer 2 was prepared in similar way as Diastereomer 1 using peak 2 from last step. LC-MS calculated for C$_{33}$H$_{33}$ClFN$_6$O$_3$S (M+H)$^+$: m/z=647.2; found 647.2.

Step 17. tert-butyl (2S,4S)-4-(8-chloro-7-(8-chloronaphthalen-1-yl)-6-fluoro-4-(methylthio)-1H-pyrazolo[4,3-c]quinolin-1-yl)-2-(cyanomethyl)piperidine-1-carboxylate

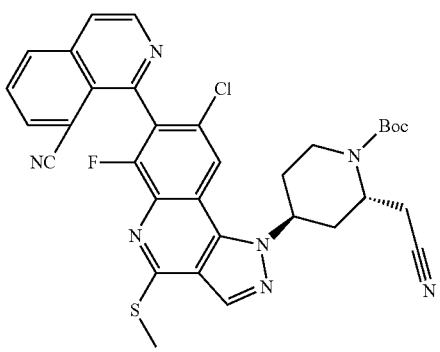 [SMILES: CSc1nc2c(F)c(-c3nccc4cccc(C#N)c34)c(Cl)cc2c2c1cnn2[C@H]1CCN(C(=O)OC(C)(C)C)[C@H](CC#N)C1]

To a solution of tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(2-hydroxyethyl)piperidine-1-carboxylate (392 mg, 0.606 mmol) in DCM (6.0 ml) was added dess-martinperiodinane (283 mg, 0.666 mmol). The resulting mixture was stirred for 1 h, to the reaction flask was added saturated NaHCO$_3$ and stirred for 10 min. The organic layer was separated and dried over Na$_2$SO$_4$, filtered and concentrated. The crude was dissolved in THF (20 mL), ammonium hydroxide (1.37 ml, 9.81 mmol) was added to reaction flask, followed by iodine (157 mg, 0.618 mmol). The resulting mixture was stirred at rt for 2 h, The reaction solution was diluted with ethyl acetate and sat. NaS$_2$O$_3$ solution. The organic layer was separated and washed with brine, dried over Na$_2$SO$_4$, filtered and concentrated. The residue was purified with flash chromatography to give the desired product (0.32 g, 82%) LC-MS calculated for C$_{33}$H$_{30}$ClFN$_7$O$_2$S (M+H)$^+$: m/z=641.2; found 641.2.

Diastereomer 2 was prepared in similar way as Diastereomer 1 using peak 2 from last step. LC-MS calculated for C$_{33}$H$_{30}$ClFN$_7$O$_2$S (M+H)$^+$: m/z=641.2; found 641.2.

Step 18. 1-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile

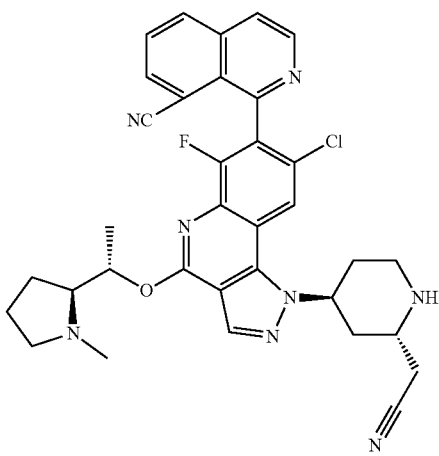 [SMILES: C[C@H](Oc1nc2c(F)c(-c3nccc4cccc(C#N)c34)c(Cl)cc2c2c1cnn2[C@H]1CCN[C@H](CC#N)C1)[C@@H]1CCCN1C]

m-CPBA (43.9 mg, 0.254 ml) was added to a solution of tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(cyanomethyl)piperidine-1-carboxylate (142 mg, 0.221 mmol) in CH$_2$Cl$_2$ (2.211 ml) at 0° C. and then the reaction was stirred at this temperature for 20 min. The reaction was quenched by adding saturated Na$_2$S$_2$O$_3$, diluted with ethyl acetate and washed with saturated NaHCO$_3$ solution, brine, filtered and concentrated and the crude was used in the next step directly.

LiHMDS (318 µl, 0.318 mmol) was added to a solution of (S)-1-((S)-1-methylpyrrolidin-2-yl)ethan-1-ol (41.0 mg, 0.318 mmol) in THF (1 mL). The resulting mixture was stirred at rt for 30 min. The first solution was added to a solution of tert-butyl (2S,4S)-4-(8-chloro-7-(8-cyanoisoquinolin-1-yl)-6-fluoro-4-(methylsulfinyl)-1H-pyrazolo[4,3-c]quinolin-1-yl)-2-(cyanomethyl)piperidine-1-carboxylate (95 mg, 0.144 mmol) in THF (2.0 ml) and then the reaction was stirred at 60° C. for 2 h. The reaction mixture was diluted with ethyl acetate and water. The organic layer was separated and dried over Na2SO4, filtered and concentrated. The residue was treated with 1:1 DCM/TFA (2 mL) for 1 h. The solvent was evaporated in vacuo. the residue was purified with prep-LCMS (XBridge C18 column, eluting with a gradient of acetonitrile/water containing 0.1% TFA, at flow rate of 60 mL/min) to give the desired product as two peaks (60 mg, 58%). LC-MS calculated for $C_{34}H_{33}ClFN_8O$ $(M+H)^+$: m/z=623.2; found 623.2.

Diastereomer 2 was prepared in similar way as Diastereomer 1 using peak 2 from last step. LC-MS calculated for $C_{34}H_{33}ClFN_8O$ $(M+H)^+$: m/z=623.2; found 623.2.

Step 19. 1-(1-((2S,4S)-1-(but-2-ynoyl)-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile To a solution of but-2-ynoic acid (0.711 mg, 8.46 μmol) and 1-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile bis (2,2,2-trifluoroacetate) (6.0 mg, 7.05 μmol) in DMF (1.0 ml) was added HATU (3.4 mg, 8.81 μmol) and DIEA (4.9 μl, 0.028 mmol). The resulting mixture was stirred at rt for 2 h. The reaction was diluted with methanol and 1 N HCl (0.1 mL) then purified using prep-LCMS (XBridge C18 column, eluting with a gradient of acetonitrile/water containing 0.1% TFA, at flow rate of 60 mL/min) to afford the desired diastereomer 1.

Diastereomer 2 was synthesized in similar way using 1-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile bis (2,2,2-trifluoroacetate) (peak2 from last step).

Example 1a. Diastereomer 1. Peak 1. LCMS calculated for $C_{38}H_{35}ClFN_8O_2$ $(M+H)^+$ m/z=689.3; found 689.3.

Example 1b. Diastereomer 2. Peak 2. LCMS calculated for $C_{38}H_{35}ClFN_8O_2$ $(M+H)^+$ m/z=689.3; found 689.3.

Example 2a and Example 2b. 1-(8-chloro-1-((2S, 4S)-2-(cyanomethyl)-1-((E)-4-methoxybut-2-enoyl) piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile

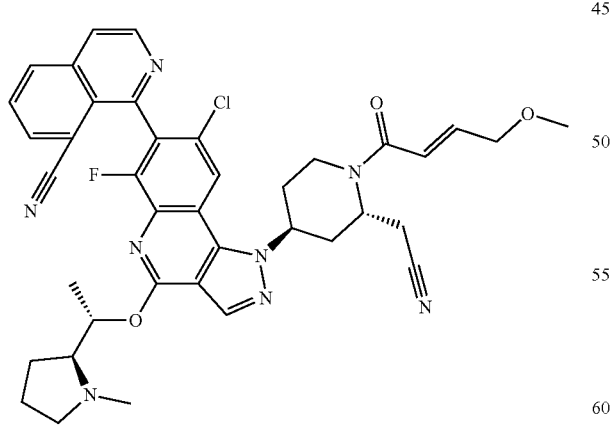

This compound was prepared according to the procedure described in Example 1a and Example 1b, step 19, replacing but-2-ynoic acid with (E)-4-methoxybut-2-enoic acid. LCMS calculated for $C_{39}H_{39}ClFN_8O_3(M+H)^+$: m/z=721.3; found: 721.3.

Example 3a and Example 3b. 1-(8-chloro-1-((2S, 4S)-2-(cyanomethyl)-1-(2-fluoroacryloyl)piperidin-4-yl)-6-fluoro-4-((S)-1-((S)-1-methylpyrrolidin-2-yl) ethoxy)-1H-pyrazolo[4,3-c]quinolin-7-yl) isoquinoline-8-carbonitrile

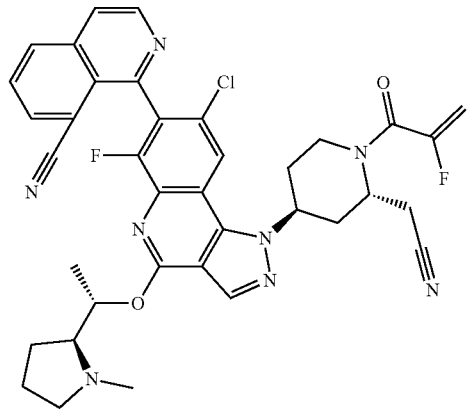 [SMILES: C=C(F)C(=O)N1CC[C@H](n2ncc3c(O[C@@H](C)[C@@H]4CCCN4C)nc4c(F)c(-c5nccc6cccc(C#N)c56)c(Cl)cc4c32)C[C@H]1CC#N]

This compound was prepared according to the procedure described in Example 1a and Example 1b, step 19, replacing but-2-ynoic acid with 2-fluoroacrylic acid. LCMS calculated for $C_{37}H_{34}ClF_2N_8O_2$ $(M+H)^+$: m/z=695.2; found: 695.2.

Example 4a and Example 4b. 2-((2S,4S)-4-(8-chloro-7-(5,6-dimethyl-1H-indazol-4-yl)-4-(3-(ethyl (methyl)amino)azetidin-1-yl)-6-fluoro-1H-pyrazolo [4,3-c]quinolin-1-yl)-1-(2-fluoroacryloyl)piperidin-2-yl)acetonitrile

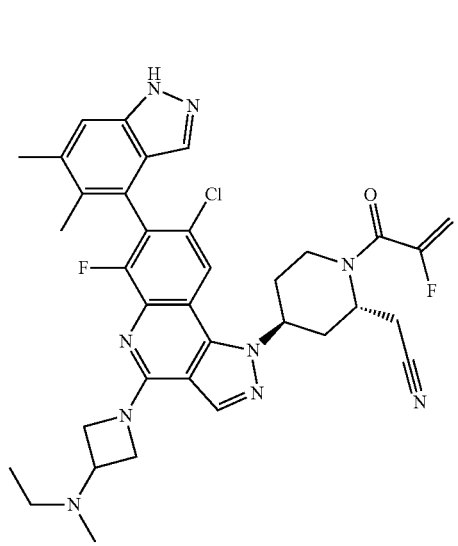 [SMILES: C=C(F)C(=O)N1CC[C@H](n2ncc3c(N4CC(N(C)CC)C4)nc4c(F)c(-c5c(C)c(C)cc6[nH]ncc56)c(Cl)cc4c32)C[C@H]1CC#N]

Step 1: methyl 2-amino-4-bromo-5-chloro-3-fluorobenzoate

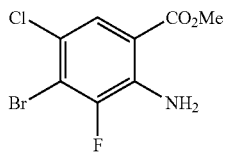

Sulfuric acid (7.76 ml, 146 mmol) was added slowly to a solution of 2-amino-4-bromo-5-chloro-3-fluorobenzoic acid (19.5 g, 72.8 mmol) in MeOH (146 ml) at r.t. The resulting mixture was heated to 80° C. overnight. The mixture was then cooled to r.t. and slowly poured into sat'd $NaHCO_3$. The mixture was stirred at r.t. for 30 min then extracted with EtOAc. The organic layer was dried over $MgSO_4$, filtered, concentrated, and used in the next step without further purification. LC-MS calculated for $C_8H_7BrClFNO_2$ $(M+H)^+$: m/z=281.9, 283.9; found 281.9, 283.9.

Step 2: ethyl 7-bromo-6-chloro-8-fluoro-4-hydroxy-2-oxo-1,2-dihydroquinoline-3-carboxylate

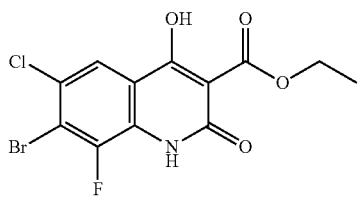 [SMILES: CCOC(=O)c1c(O)c2cc(Cl)c(Br)c(F)c2[nH]c1=O]

Ethyl 3-chloro-3-oxopropanoate (9.60 ml, 75.0 mmol) was added dropwise to a solution of methyl 2-amino-4-bromo-5-chloro-3-fluorobenzoate (19.25 g, 68.1 mmol) and TEA (14.25 ml, 102 mmol) in DCM (150 mL) at rt. After stirring for 1 h, additional ethyl 3-chloro-3-oxopropanoate (1.745 ml, 13.63 mmol) added. After stirring for another 1 h, the reaction was quenched with water then extracted with ethyl acetate. The organic layer was dried, filtered, then concentrated. The concentrated residue was redissolved in EtOH (150 ml) and sodium ethoxide in ethanol (53.4 ml, 143 mmol) was added. stirred at r.t. for 1 h. The reaction mixture was poured into water (1 L) and acidify to pH ~3, The resulting precipitate was collected via filtration to give the desired product (18.39 g, 74.0%). LC-MS calculated for $C_{12}H_9BrClFNO_4$ $(M+H)^+$: m/z=363.9, 365.9; found 363.9, 365.9.

Step 3: ethyl 7-bromo-2,4,6-trichloro-8-fluoroquinoline-3-carboxylate

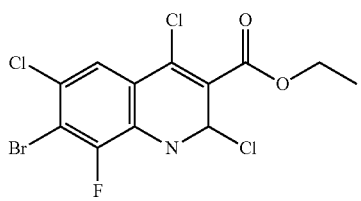 [SMILES: CCOC(=O)C1=C(Cl)c2cc(Cl)c(Br)c(F)c2NC1Cl]

Ethyl 7-bromo-6-chloro-8-fluoro-2,4-dihydroxyquinoline-3-carboxylate (2.0 g, 5.49 mmol) was dissolved in $POCl_3$ (10.2 ml, 110 mmol), and DIEA (1.92 ml, 10.97 mmol) was added. The resulting mixture was stirred at 100° C. for 2 h. After cooling to r.t., the reaction was quenched by slowly pouring into rapidly stirred ice water (~250 mL), stirred for 30 min then collected solids via filtration to yield the desired product as a brown solid (1.66 g, 75%). LC-MS calculated for $C_{12}H_7BrCl_3FNO_2$ $(M+H)^+$: m/z=399.9, 401.9, 403.9; found 399.9, 401.9, 403.9.

Step 4. tert-butyl (R)-6-cyano-5-hydroxy-3-oxohexanoate

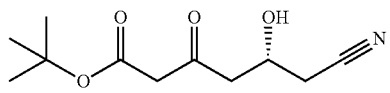

To a solution of 2.0 M LDA (100 ml, 200 mmol) in anhydrous THF (223 ml) was cooled to −78° C. for 1 h, and then tert-butyl acetate (26.9 ml, 200 mmol) was added dropwise with stirring over 20 min. After an additional 40 minutes maintained at −78° C., a solution of ethyl (R)-4-cyano-3-hydroxybutanoate (10.5 g, 66.8 mmol) was added dropwise. The mixture was allowed to stir at −40° C. for 4 h, and then an appropriate amount of HCl (2 M) was added to the mixture, keeping pH ~6. During this quench, the temperature of the mixture was maintained at −10° C. Upon completion, the temperature of the mixture was cooled to 0° C. The mixture was extracted with ethyl acetate (3×100 mL). The combined organic layer was washed with $NaHCO_3$ (100 mL) and brine (100 mL), dried over anhydrous $Na_2SO_4$, and evaporated to provide the material as yellow oil (15.0 g, 99%).

Step 5. tert-butyl (2S,4R)-2-(2-(tert-butoxy)-2-oxoethyl)-4-hydroxypiperidine-1-carboxylate

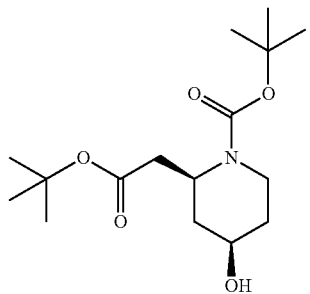 [SMILES: CC(C)(C)OC(=O)C[C@@H]1C[C@H](O)CCN1C(=O)OC(C)(C)C]

A solution of tert-butyl (R)-6-cyano-5-hydroxy-3-oxohexanoate (15.0 g, 66.0 mmol) in acetic acid (110 ml) was treated with platinum (IV) oxide hydrate (0.868 g, 3.30 mmol). The Parr bottle was evacuated and backfilled with $H_2$ three times and stirred under a $H_2$ atmosphere (45 psi, recharged 4 times) at 22° C. for 3 h. The mixture was filtered through Celite and the filter cake was washed with EtOH. The filtrate was concentrated to yield product with a ~9:1 cis:trans diastereomer ratio. The residue was dissolved in methanol (100 mL) then Boc-anhydride (15.3 ml, 66.0 mmol), sodium carbonate (13.99 g, 132 mmol) was added. The reaction mixture was stirred at room temperature overnight. The mixture was filtered and concentrated. The residue was purified with silica gel column to give the desired product (11.7 g, 56%). LCMS (product+Na⁺) calculated for $C_{16}H_{29}NNaO_5$ (M+Na)⁺: m/z=338.2; found: 338.2.

Step 6. tert-butyl (2S,4S)-4-azido-2-(2-(tert-butoxy)-2-oxoethyl)piperidine-1-carboxylate

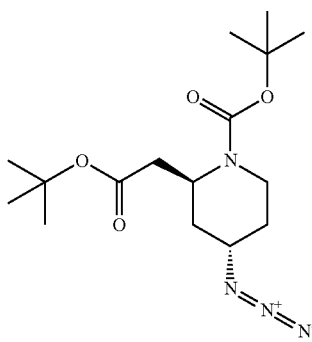

To a solution of tert-butyl (2S,4R)-2-(2-(tert-butoxy)-2-oxoethyl)-4-hydroxypiperidine-1-carboxylate (2.10 g, 6.66 mmol) in DCM (33 ml) at 0° C. was added Ms-Cl (0.67 mL, 8.66 mmol), After stirring for 1 h, The reaction was diluted with water and organic layer was separated and dried over $Na_2SO_4$, filtered and concentrated. The resulting residue was dissolved in DMF and sodium azide (1.3 g, 20 mmol) was added and the reaction mixture was heated at 70° C. for 5 h. After cooling to rt, the reaction was diluted with EtOAc and water. The organic layer was separated and dried over $Na_2SO_4$, filtered and concentrated. The residue was purified with silica gel column to give the desired product (1.90 g, 84%). LCMS calculated for (Product-Boc) $C_{11}H_{21}N_4O_2$ (M+H)⁺: m/z=241.2; found: 241.2.

Step 7. tert-butyl (2S,4S)-4-azido-2-(2-hydroxyethyl)piperidine-1-carboxylate

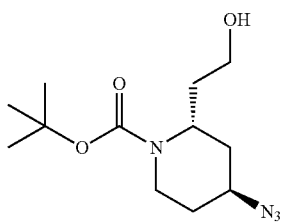 [SMILES: CC(C)(C)OC(=O)N1CC[C@H](N=[N+]=[N-])C[C@H]1CCO]

To a solution of tert-butyl (2S,4S)-4-azido-2-(2-(tert-butoxy)-2-oxoethyl)piperidine-1-carboxylate (21.4 g, 62.9 mmol) in DCM (400 ml) at −78° C. was added 1.0 M DIBAL-H in DCM (113 ml, 113 mmol). The resulting mixture was stirred at −78° C. for 2 h. The reaction was quenched with methanol (38.1 ml, 943 mmol) at −78° C. Aqueous Rochelle salt solution (prepared from 126 g (6 wt) of Rochelle salt and 300 mL of water) was added to the solution at ≤10° C. The biphasic mixture was stirred vigorously for ≥1 h at 15-25° C. and separated to give organic layer. The biphasic mixture was separated. The organic layer was washed with aqueous NaCl (×2) at 15-25° C., The organic layer was dried over $Na_2SO_4$, filtered and concentrated. and used as is. The residue was dissolved in the methanol (300 mL) and sodium borohydride (1.43 g, 37.7 mmol) was added at 0° C. The reaction mixture was stirred at 0° C. for 1 h. The reaction was quenched with water, methanol was evaporated under reduced pressure. The reaction mixture was extracted with ethyl acetate (2×), the organic layer was washed with brine, dried over $Na_2SO_4$, filtered and concentrated. The crude was purified with flash chromatography (eluting with a gradient 0-50% ethyl acetate in hexanes) to give the desired product as colorless oil (14.8 g, 87%). LCMS calculated for (Product-Boc) $C_7H_{15}N_4O$ (M+H)⁺: m/z=171.1; found: 171.1.

Step 8. tert-butyl (2S,4S)-4-azido-2-(2-((tert-butyldimethylsilyl)oxy)ethyl)piperidine-1-carboxylate

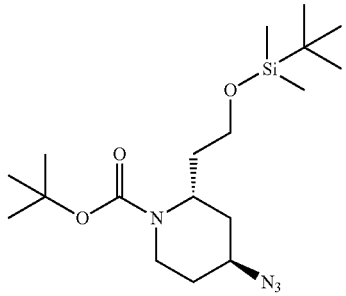 [SMILES: CC(C)(C)OC(=O)N1CC[C@H](N=[N+]=[N-])C[C@H]1CCO[Si](C)(C)C(C)(C)C]

To a solution of tert-butyl (2S,4S)-4-azido-2-(2-hydroxyethyl)piperidine-1-carboxylate (4.0 g, 14.80 mmol) in DMF (74.0 ml) was added imidazole (1.51 g, 22.2 mmol) and TBS-Cl (2.90 g, 19.24 mmol). The resulting mixture was stirred at 60° C. for 1 h 15 min. The reaction mixture was diluted with EtOAc and water. The organic layer was washed with water (2×), brine, dried over $Na_2SO_4$, filtered and concentrated. The residue was purified with flash chromatography (0-20% ethyl acetate in hexanes) to give the desired product as colorless oil. (5.30 g, 93%). LCMS calculated for (Product-Boc) $C_{13}H_{29}N_4OSi$ (M+H)⁺: m/z=285.2; found: 285.2.

Step 9. tert-butyl (2S,4S)-4-amino-2-(2-((tert-butyldimethylsilyl)oxy)ethyl)piperidine-1-carboxylate

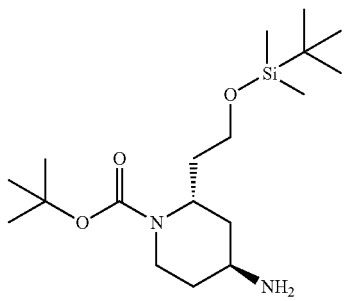 [SMILES: CC(C)(C)OC(=O)N1CC[C@H](N)C[C@H]1CCO[Si](C)(C)C(C)(C)C]

To a solution of tert-butyl (2S,4S)-4-azido-2-(2-((tert-butyldimethylsilyl)oxy)ethyl)-piperidine-1-carboxylate (5.30 g, 13.78 mmol) in methanol (70 ml) was added 10% palladium on carbon (1.47 g, 1.38 mmol). The reaction mixture was evacuated under vacuum and refilled with H₂, stirred at rt for 2 h. The reaction mixture was filtered through a pad of Celite and washed with methanol. The filtrate was concentrated to give the desired product (4.5 g, 91%). LCMS calculated for (Product-Boc) $C_{13}H_{31}N_2OSi$ (M+H)⁺: m/z=259.2; found: 259.2.

Step 10. ethyl 7-bromo-4-(((2S,4S)-1-(tert-butoxy-carbonyl)-2-(2-((tert-butyldimethylsilyl)oxy)ethyl)piperidin-4-yl)amino)-2,6-dichloro-S-fluoroquino-line-3-carboxylate

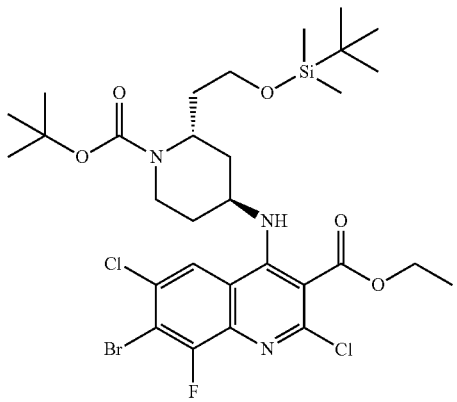 [SMILES: CCOC(=O)c1c(Cl)nc2c(F)c(Br)c(Cl)cc2c1N[C@H]1CCN(C(=O)OC(C)(C)C)[C@H](CCO[Si](C)(C)C(C)(C)C)C1]

To a solution of ethyl 7-bromo-2,4,6-trichloro-8-fluoroquinoline-3-carboxylate (8.7 g, 21.7 mmol) in DMF (80 ml) was added tert-butyl (2S,4S)-4-amino-2-(2-((tert-butyldimethylsilyl)oxy)ethyl)piperidine-1-carboxylate (9.33 g, 26.0 mmol) and DIEA (7.6 ml, 43.3 mmol). The resulting mixture was stirred at 65° C. for 5 h. After cooling to room temperature, ethyl acetate and water were added. The organic layer was washed with water (2×) and brine, dried over Na₂SO₄, filtered and concentrated. The residue was purified with flash chromatography (eluting with 0%-25% ethyl acetate in hexanes) to give the desired product as foam (14.6 g, 93%). LC-MS calculated for $C_{30}H_{44}BrCl_2FN_3O_5Si$ (M+H)⁺: m/z=722.2, 724.2; found 722.2, 724.2.

Step 11. tert-butyl (2S,4S)-4-((7-bromo-2,6-dichloro-8-fluoro-3-(hydroxymethyl)quinolin-4-yl)amino)-2-(2-((tert-butyldimethylsilyl)oxy)ethyl)piperidine-1-carboxylate

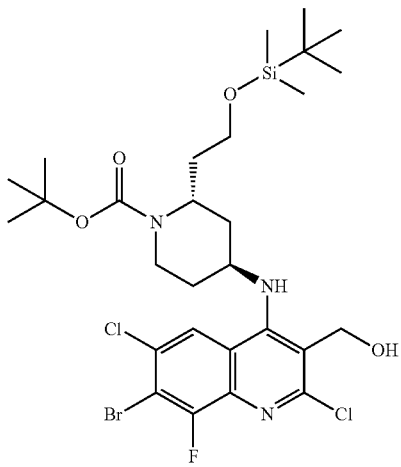 [SMILES: CC(C)(C)OC(=O)N1CC[C@H](Nc2c(CO)c(Cl)nc3c(F)c(Br)c(Cl)cc23)C[C@H]1CCO[Si](C)(C)C(C)(C)C]

To a solution of ethyl 7-bromo-4-(((2S,4S)-1-(tert-butoxycarbonyl)-2-(2-((tert-butyldimethylsilyl)oxy)ethyl)piperidin-4-yl)amino)-2,6-dichloro-8-fluoroquinoline-3-carboxylate (14.6 g, 20.18 mmol) in toluene (200 ml) at −78° C. was added 1.0 M DIBAL-H in DCM (60.5 ml, 60.5 mmol). The resulting mixture was stirred at −78° C. for 40 min and warm to 0° C. for 1 h and 20 min, quenched with methanol (6.8 ml, 167 mmol). Aqueous Rochelle salt solution (prepared from 88 g (6 wt) of Rochelle salt and 200 mL of water) was added to the solution at ≤10° C. The biphasic mixture was stirred vigorously for ≥1 h at 15-25° C. and separated to give organic layer. The biphasic mixture was separated. The organic layer was washed with brine, dried over Na₂SO₄, filtered and concentrated. The crude was used as is. LC-MS calculated for $C_{28}H_{42}BrCl_2FN_3O_4Si$ (M+H)⁺: m/z=680.1, 682.1; found 680.1, 682.1.

Step 12. tert-butyl (2S,4S)-4-((7-bromo-2,6-dichloro-8-fluoro-3-formylquinolin-4-yl)amino)-2-(2-((tert-butyldimethylsilyl)oxy)ethyl) piperidine-1-carboxylate

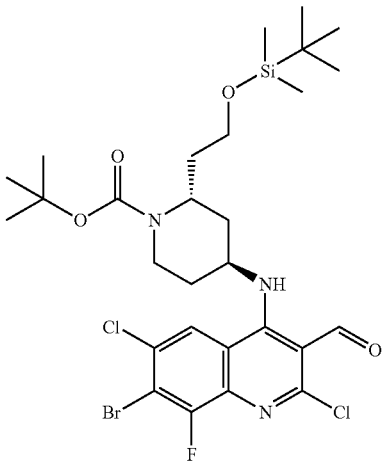 [SMILES: CC(C)(C)OC(=O)N1CC[C@H](Nc2c(C=O)c(Cl)nc3c(F)c(Br)c(Cl)cc23)C[C@H]1CCO[Si](C)(C)C(C)(C)C]

To a solution of tert-butyl (2S,4S)-4-((7-bromo-2,6-dichloro-8-fluoro-3-(hydroxymethyl)quinolin-4-yl)amino)-2-(2-((tert-butyldimethylsilyl)oxy)ethyl)piperidine-1-carboxylate (13.0 g, 19.07 mmol) in DCM (150 ml) and acetonitrile (50 ml) was added IBX (16.02 g, 57.2 mmol) and acetic acid (3.28 ml, 57.2 mmol). The resulting reaction mixture was stirred at 35° C. for 16 h. The reaction mixture was filtered and the filtrate was concentrated. The resulting residue was triturated with EtOAc, the resulting precipitate was collected via filtration, dried under vacuum to give the desired product as light yellow solid (9.4 g, 73% over 2 steps). LC-MS calculated for $C_{28}H_{40}BrCl_2FN_3O_4Si$ (M+H)⁺: m/z=678.1, 680.1; found 678.1, 680.1.

Step 13. tert-butyl (2S,4S)-4-((7-bromo-2,6-dichloro-8-fluoro-3-((E)-(hydroxyimino)methyl)quinolin-4-yl)amino)-2-(2-((tert-butyldimethylsilyl)oxy)ethyl)piperidine-1-carboxylate

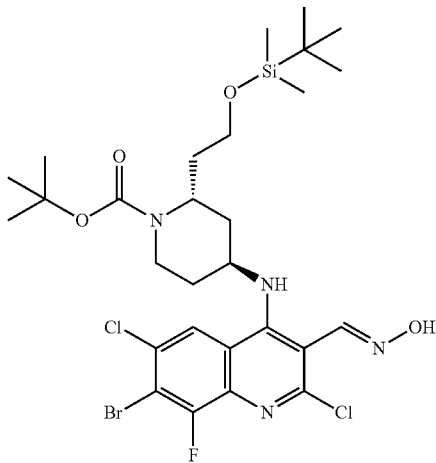

To a mixture of tert-butyl (2S,4S)-4-((7-bromo-2,6-dichloro-8-fluoro-3-formylquinolin-4-yl)amino)-2-(2-((tert-butyldimethylsilyl)oxy)ethyl)piperidine-1-carboxylate (7.67 g, 11.29 mmol), DCM (56 ml) and EtOH (56 ml) was added hydroxylamine hydrochloride (2.35 g, 33.9 mmol) and pyridine (2.8 ml, 34.4 mmol). The reaction mixture was stirred at 40° C. for 16 hours. Another portion of pyridine (2.8 ml, 34.4 mmol) and hydroxylamine hydrochloride (2.35 g, 33.9 mmol) and stirred for 4 h. The solvent was evaporated in vacuo. The residue with DCM and water. The aqueous layer was extracted with DCM. The combined organic layers were washed with aqueous CuSO$_4$, brine, dried over MgSO$_4$, filtered and concentrated in vacuo. The residue was purified with column chromatography on silica gel to give the desired product (4.5 g, 57%). LC-MS calculated for $C_{28}H_{41}BrCl_2FN_4O_4Si$ (M+H)$^+$: m/z=693.1, 695.1; found 693.1, 695.1.

Step 14. tert-butyl (2S,4S)-4-(7-bromo-4,8-dichloro-6-fluoro-1H-pyrazolo[4,3-c]quinolin-1-yl)-2-(2-((tert-butyldimethylsilyl)oxy)ethyl)piperidine-1-carboxylate

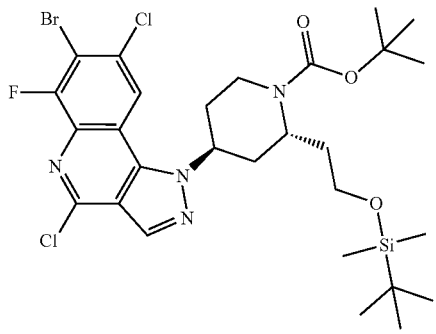 [SMILES: CC(C)(C)OC(=O)N1CC[C@H](n2ncc3c(Cl)nc4c(F)c(Br)c(Cl)cc4c32)C[C@H]1CCO[Si](C)(C)C(C)(C)C]

To a solution of (tert-butyl (2S,4S)-4-((7-bromo-2,6-dichloro-8-fluoro-3-((E)-(hydroxyimino)methyl)quinolin-4-yl)amino)-2-(2-((tert-butyldimethylsilyl)oxy)ethyl)piperidine-1-carboxylate (4.53 g, 6.52 mmol) in CH$_2$Cl$_2$ (75 mL) was added 2-aminopyridine (0.798 g, 8.48 mmol)) and Ms-Cl (0.610 ml, 7.83 mmol) at 0° C. The resulting mixture was stirred at 0° C. for 2 hours. The reaction mixture was allowed to warm to room temperature overnight, The reaction was diluted with water. The organic layer was washed with brine, dried over MgSO$_4$, filtered and concentrated. The crude product was purified by column chromatography on silica gel (eluting with a gradient of 0-40% ethyl acetate in hexanes) to give the desired product (1.80 g, 41%). LC-MS calculated for $C_{28}H_{39}BrCl_2FN_4O_3Si$ (M+H)$^+$: m/z=675.1, 677.1; found 675.1, 677.1.

Step 15. tert-butyl (2S,4S)-4-(7-bromo-8-chloro-6-fluoro-4-(methylthio)-1H-pyrazolo[4,3-c]quinolin-1-yl)-2-(2-((tert-butyldimethylsilyl)oxy)ethyl)piperidine-1-carboxylate

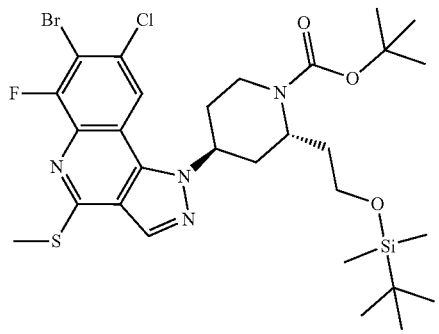 [SMILES: CSc1nc2c(F)c(Br)c(Cl)cc2c2c1cnn2[C@H]1CCN(C(=O)OC(C)(C)C)[C@H](CCO[Si](C)(C)C(C)(C)C)C1]

Sodium thiomethoxide (0.56 g, 8.00 mmol) was added to a mixture of tert-butyl (2S,4S)-4-(7-bromo-4,8-dichloro-6-fluoro-1H-pyrazolo[4,3-c]quinolin-1-yl)-2-(2-((tert-butyldimethylsilyl)-oxy)ethyl)piperidine-1-carboxylate (1.80 g, 2.67 mmol) in MeOH (26 ml)/DCM (26 ml) and then stirred at rt for 1 h. The mixture was diluted with sat'd NH$_4$Cl and extracted with EtOAc. The combined organic layers were dried over MgSO$_4$, filtered, concentrated. The crude product was purified by column chromatography on silica gel to give the desired product (1.75 g, 95%). LC-MS calculated for $C_{29}H_{42}BrClFN_4O_3SSi$ (M+H)$^+$: m/z=687.2, 689.2; found 687.2, 689.2.

Step 16. tert-butyl (2S,4S)-4-(7-bromo-8-chloro-6-fluoro-4-(methylthio)-1H-pyrazolo[4,3-c]quinolin-1-yl)-2-(2-hydroxyethyl)piperidine-1-carboxylate

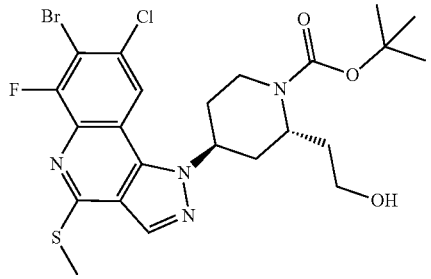 [SMILES: CSc1nc2c(F)c(Br)c(Cl)cc2c2c1cnn2[C@H]1CCN(C(=O)OC(C)(C)C)[C@H](CCO)C1]

To a solution of tert-butyl (2S,4S)-4-(7-bromo-8-chloro-6-fluoro-4-(methylthio)-1H-pyrazolo[4,3-c]quinolin-1-yl)-2-(2-((tert-butyldimethylsilyl)oxy)ethyl)piperidine-1-carboxylate (1.96 g, 2.84 mmol) in THF (28 ml) was added 1.0 M TBAF in THF (4.27 ml, 4.27 mmol). The resulting mixture was stirred at 60° C. for 1 h. After cooling to rt, the reaction mixture was diluted with water and ethyl acetate. The organic layer was separated and washed with brine, dried over Na$_2$SO$_4$, filtered and concentrated. The crude was used as is. LC-MS calculated for C$_{23}$H$_{28}$BrClFN$_4$O$_3$S (M+H)$^+$: m/z=573.1, 575.1; found 573.1, 575.1.

Step 17. tert-butyl (2S,4S)-4-(7-bromo-8-chloro-6-fluoro-4-(methylthio)-1H-pyrazolo[4,3-c]quinolin-1-yl)-2-(cyanomethyl)piperidine-1-carboxylate

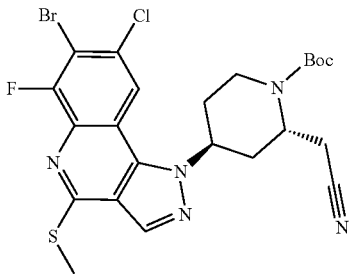 [SMILES: CSc1nc2c(F)c(Br)c(Cl)cc2c2c1cnn2[C@H]1CCN(C(=O)OC(C)(C)C)[C@H](CC#N)C1]

To a solution of tert-butyl (2S,4S)-4-(7-bromo-8-chloro-6-fluoro-4-(methylthio)-1H-pyrazolo[4,3-c]quinolin-1-yl)-2-(2-hydroxyethyl)piperidine-1-carboxylate (0.50 g, 0.871 mmol) in DCM (8 ml) was added dess-martinperiodinane (0.406 g, 0.958 mmol). The resulting mixture was stirred for 1 h, To the reaction flask was added saturated NaHCO$_3$ and stirred for 10 min. The organic layer was separated and dried over Na$_2$SO$_4$, filtered and concentrated. The crude was dissolved in THF (10 mL), ammonium hydroxide (1.96 ml, 14.11 mmol) was added to reaction flask, followed by iodine (0.243 g, 0.958 mmol). The resulting mixture was stirred at rt for 3 h, The reaction solution was diluted with ethyl acetate and sat'd NaS$_2$O$_3$ solution. The organic layer was separated and washed with brine, dried over Na$_2$SO$_4$, filtered and concentrated. The residue was purified with flash chromatography to give the desired product (0.40 g, 80%). LC-MS calculated for C$_{23}$H$_{25}$BrClFN$_5$O$_2$S (M+H)$^+$: m/z=568.1, 570.1; found 568.1, 570.1.

Step 18. tert-butyl (2S,4S)-4-(8-chloro-7-(6-chloro-5-methyl-1-(tetrahydro-2H-pyran-2-yl)-1H-indazol-4-yl)-6-fluoro-4-(methylthio)-1H-pyrazolo[4,3-c]quinolin-1-yl)-2-(cyanomethyl)piperidine-1-carboxylate

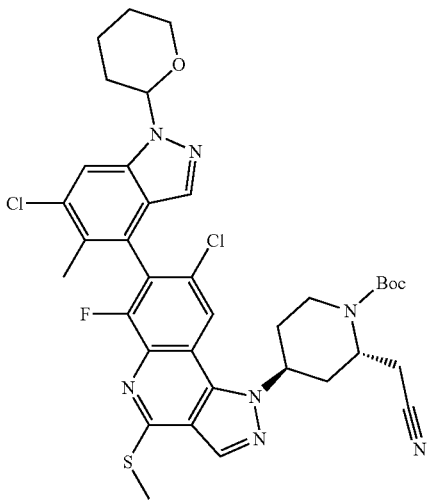 [SMILES: CSc1nc2c(F)c(-c3c(C)c(Cl)cc4c3cnn4C3CCCCO3)c(Cl)cc2c2c1cnn2[C@H]1CCN(C(=O)OC(C)(C)C)[C@H](CC#N)C1]

The vial charged with tert-butyl (2S,4S)-4-(7-bromo-8-chloro-6-fluoro-4-(methylthio)-1H-pyrazolo[4,3-c]quinolin-1-yl)-2-(cyanomethyl)piperidine-1-carboxylate (401 mg, 0.705 mmol), 6-chloro-5-methyl-1-(tetrahydro-2H-pyran-2-yl)-4-(4,4,5,5-tetramethyl-1,3,2-dioxaborolan-2-yl)-1H-indazole (319 mg, 0.846 mmol), tetrakis(triphenylphosphine)palladium(0) (122 mg, 0.106 mmol), sodium carbonate (299 mg, 2.82 mmol) and 5:1 dioxane/water (6 ml) were heated at 105° C. overnight. The mixture was diluted with brine and EtOAc, the organic layer was separated, dried over MgSO$_4$, filtered and concentrated. The crude product was purified by column chromatography to give the desired product (0.39 g, 75%). LC-MS calculated for C$_{36}$H$_{39}$Cl$_2$FN$_7$O$_3$S (M+H)$^+$: m/z=738.2; found 738.2.

Step 19. tert-butyl (2S,4S)-4-(8-chloro-7-(5,6-dimethyl-1-(tetrahydro-2H-pyran-2-yl)-1H-indazol-4-yl)-4-(3-(ethyl(methyl)amino)azetidin-1-yl)-6-fluoro-1H-pyrazolo[4,3-c]quinolin-1-yl)-2-(cyanomethyl)piperidine-1-carboxylate

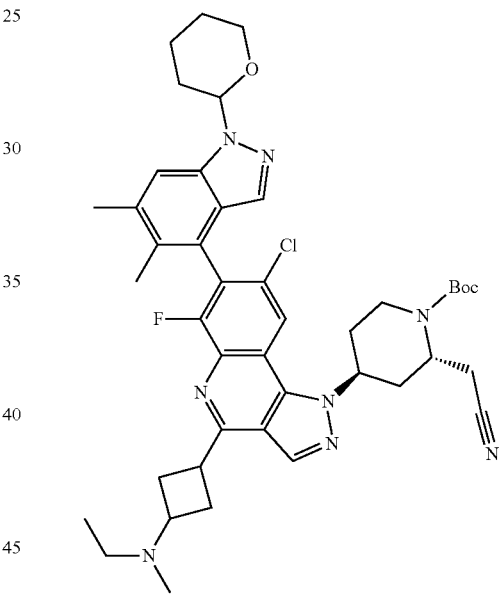

To a solution of tert-butyl (2S,4S)-4-(8-chloro-7-(6-chloro-5-methyl-1-(tetrahydro-2H-pyran-2-yl)-1H-indazol-4-yl)-6-fluoro-4-(methylthio)-1H-pyrazolo[4,3-c]quinolin-1-yl)-2-(cyanomethyl)piperidine-1-carboxylate (0.73 g, 0.988 mmol) in DCM (10 ml) at 0° C. was added m-CPBA (0.196 g, 1.136 mmol). The reaction mixture was stirred at this temperature for 20 min. The reaction was quenched by adding sat'd Na$_2$S$_2$O$_3$, diluted with ethyl acetate and washed with saturated NaHCO$_3$, brine, filtered, dried and concentrated. The crude was dissolve in acetonitrile (8 ml) and triethylamine (0.607 ml, 4.36 mmol) and N-ethyl-N-methylazetidin-3-amine dihydrochloride (0.306 g, 1.634 mmol) was added to reaction vial and the resulting mixture was stirred at 80° C. for 2 h. The crude was concentrated and the residue was purified by silica gel column (eluting with a gradient of 0-20% DCM in MeOH) to give the desired product (0.65 g, 76%). LC-MS calculated for C$_{42}$H$_{52}$ClFN$_9$O$_3$(M+H)$^+$: m/z=784.4; found 784.4.

Step 20. 2-((2S,4S)-4-(8-chloro-7-(5,6-dimethyl-1H-indazol-4-yl)-4-(3-(ethyl(methyl)amino)azetidin-1-yl)-6-fluoro-1H-pyrazolo[4,3-c]quinolin-1-yl)piperidin-2-yl)acetonitrile

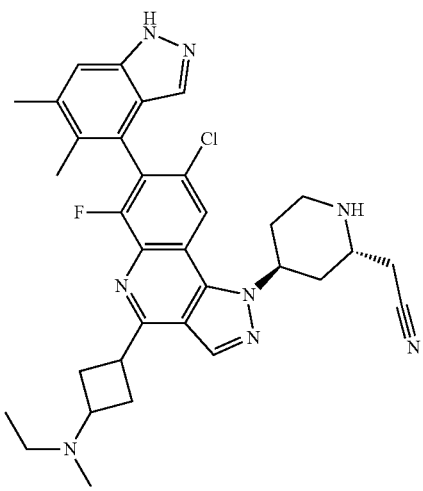 [SMILES: CCN(C)C1CC(c2nc3c(F)c(-c4c(C)c(C)cc5[nH]ncc45)c(Cl)cc3c3c2cnn3[C@H]2CCN[C@H](CC#N)C2)C1]

To a solution of tert-butyl (2S,4S)-4-(8-chloro-7-(6-chloro-5-methyl-1-(tetrahydro-2H-pyran-2-yl)-1H-indazol-4-yl)-4-(3-(dimethylamino)azetidin-1-yl)-6-fluoro-1H-pyrazolo[4,3-c]quinolin-1-yl)-2-(cyanomethyl)piperidine-1-carboxylate (0.65 g, 0.771 mmol) in DCM (5 ml) was added TFA (4.8 ml, 61.7 mmol). After stirring for 0.5 h, the solvent was removed in vacuo, the residue was purified with prep-LCMS (XBridge C18 column, eluting with a gradient of acetonitrile/water containing 0.1% TFA, at flow rate of 60 mL/min) to give the desired product as two peaks (0.40 g, 85%).

Diastereomer 1. Peak 1. LC-MS calculated for $C_{32}H_{36}ClFN_9$ (M+H)$^+$: m/z=600.3; found 600.3.
Diastereomer 2. Peak 2. LC-MS calculated for $C_{32}H_{36}ClFN_9$ (M+H)$^+$: m/z=600.3; found 600.3.

Step 21. 2-((2S,4S)-4-(8-chloro-7-(5,6-dimethyl-1H-indazol-4-yl)-4-(3-(ethyl(methyl)amino)azetidin-1-yl)-6-fluoro-1H-pyrazolo[4,3-c]quinolin-1-yl)-1-(2-fluoroacryloyl)piperidin-2-yl)acetonitrile To a solution of 2-fluoroacrylic acid (1.1 mg, 0.012 mmol) and 2-((2S,4S)-4-(8-chloro-7-(5,6-dimethyl-1H-indazol-4-yl)-4-(3-(ethyl(methyl)amino)azetidin-1-yl)-6-fluoro-1H-pyrazolo[4,3-c]quinolin-1-yl)piperidin-2-yl)acetonitrile bis (2,2,2-trifluoroacetate) (8.5 mg, 10.3 μmol) (peak 2 from last step) in DMF (1.0 ml) was added HATU (5.1 mg, 0.013 mmol) and DIEA (9.0 μl, 0.051 mmol). The resulting mixture was stirred at rt for 2 h. The reaction was diluted with methanol and 1 N HCl (0.1 mL) and purified using prep-LCMS (XBridge C18 column, eluting with a gradient of acetonitrile/water containing 0.1% TFA, at flow rate of 60 mL/min) to afford the desired diastereomer 1.

Diastereomer 2 was synthesized in similar way using 2-((2S,4S)-4-(8-chloro-7-(6-chloro-5-methyl-1H-indazol-4-yl)-4-(3-(dimethylamino)azetidin-1-yl)-6-fluoro-1H-pyrazolo[4,3-c]quinolin-1-yl)piperidin-2-yl)acetonitrile bis(2,2,2-trifluoroacetate) (peak1 from last step). Example 4a. Diastereomer 1. Peak 1. LCMS calculated for $C_{35}H_{37}ClF_2N_9O$ (M+H)$^+$ m/z=672.3; found 672.3. $^1$H NMR (500 MHz, DMSO) b 8.34 (m, 2H), 7.48 (s, 1H), 7.38 (s, 1H), 5.70 (m, 1H), 5.35 (m, 2H), 4.98-4.27 (m, 9H), 3.54 (m, 2H), 3.27 (m, 2H), 2.86 (m, 2H), 2.49 (s, 3H), 2.37-2.27 (m, 4H), 2.09 (s, 3H), 1.28 (t, J=7.2 Hz, 3H). Example 4b. Diastereomer 2. Peak 2. LCMS calculated for $C_{35}H_{37}ClF_2N_9O$ (M+H)$^+$ m/z=672.3; found 672.3.

Example 5a and Example 5b. 8-(8-chloro-1-((2S,4S)-2-(cyanomethyl)-1-(2-fluoroacryloyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile

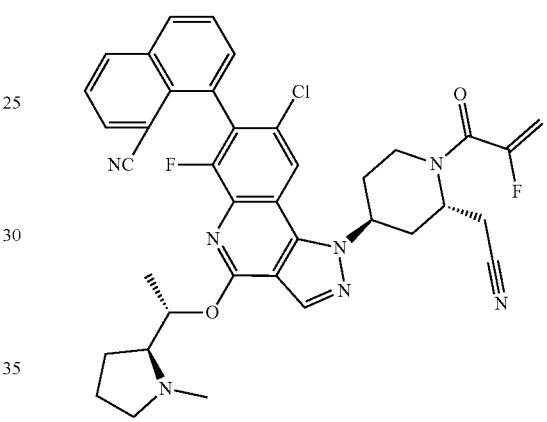

Step 1. ethyl 2-amino-4-(8-cyanonaphthalen-1-yl)-3-fluorobenzoate

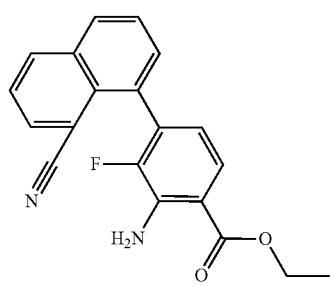 [SMILES: CCOC(=O)c1ccc(-c2cccc3cccc(C#N)c23)c(F)c1N]

The title compound was synthesized according to the procedure described for Example 1a and Example 1b in step 5, utilizing 8-bromo-1-naphthonitrile instead of 1-chloroisoquinoline-8-carbonitrile. LCMS calculated for $C_{20}H_{16}FN_2O_2$(M+H)$^+$ m/z=335.1; found 335.1.

Step 2. ethyl 2-amino-5-chloro-4-(8-cyanonaphthalen-1-yl)-3-fluorobenzoate

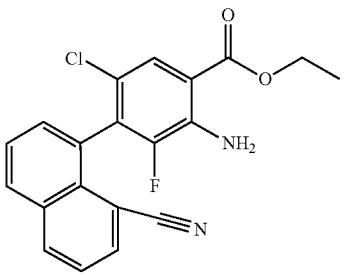 [SMILES: CCOC(=O)c1cc(Cl)c(-c2cccc3cccc(C#N)c23)c(F)c1N]

The title compound was synthesized according to the procedure described for Example 1a and Example 1b in step 6, utilizing ethyl 2-amino-4-(8-cyanonaphthalen-1-yl)-3-fluorobenzoate instead of ethyl 2-amino-4-(8-cyanoisoquinolin-1-yl)-3-fluorobenzoate. LCMS calculated for $C_{20}H_{15}ClFN_2O_2(M+H)^+$ m/z=369.1; found 369.1.

Step 3. ethyl 5-chloro-4-(8-cyanonaphthalen-1-yl)-2-(3-ethoxy-3-oxopropanamido)-3-fluorobenzoate

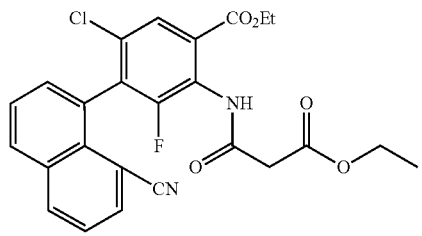 [SMILES: CCOC(=O)CC(=O)Nc1c(C(=O)OCC)cc(Cl)c(-c2cccc3cccc(C#N)c23)c1F]

This compound was prepared according to the procedure described in Example 1a and Example 1b, in Step 7 replacing ethyl 2-amino-5-chloro-4-(8-cyanoisoquinolin-1-yl)-3-fluorobenzoate with ethyl 2-amino-5-chloro-4-(8-cyanonaphthalen-1-yl)-3-fluorobenzoate. LC-MS calculated for $C_{25}H_{21}ClFN_2O_5(M+H)^+$: m/z=483.1; found 483.1.

Step 4. ethyl 6-chloro-7-(8-cyanonaphthalen-1-yl)-8-fluoro-2,4-dihydroxyquinoline-3-carboxylate

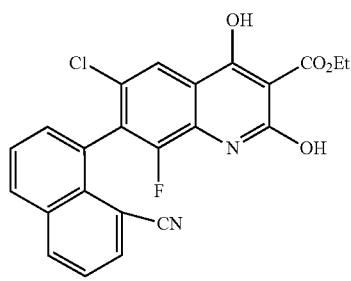

This compound was prepared according to the procedure described in Example 1a and Example 1b, in Step 8 replacing ethyl 5-chloro-4-(8-cyanoisoquinolin-1-yl)-2-(3-ethoxy-3-oxopropanamido)-3-fluorobenzoate with ethyl 5-chloro-4-(8-cyanonaphthalen-1-yl)-2-(3-ethoxy-3-oxopropanamido)-3-fluorobenzoate. LC-MS calculated for $C_{23}H_{15}ClFN_2O_4$ (M+H)$^+$: m/z=437.1; found 437.1.

Step 5. ethyl 2,4,6-trichloro-7-(8-cyanonaphthalen-1-yl)-8-fluoroquinoline-3-carboxylate

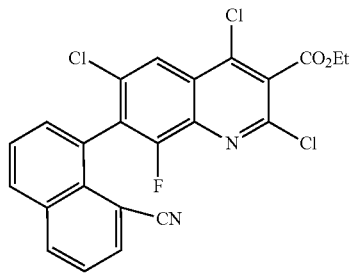 [SMILES: CCOC(=O)c1c(Cl)nc2c(F)c(-c3cccc4cccc(C#N)c34)c(Cl)cc2c1Cl]

This compound was prepared according to the procedure described in Example 1a and Example 1b, in Step 9 replacing ethyl 6-chloro-7-(8-cyanoisoquinolin-1-yl)-8-fluoro-2,4-dihydroxyquinoline-3-carboxylate with ethyl 6-chloro-7-(8-cyanonaphthalen-1-yl)-8-fluoro-2,4-dihydroxyquinoline-3-carboxylate. LC-MS calculated for $C_{23}H_{13}C_{13}FN_2O_2(M+H)^+$: m/z=473.0, 475.0; found 473.1, 475.1.

Step 6. ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanonaphthalen-1-yl)-8-fluoroquinoline-3-carboxylate

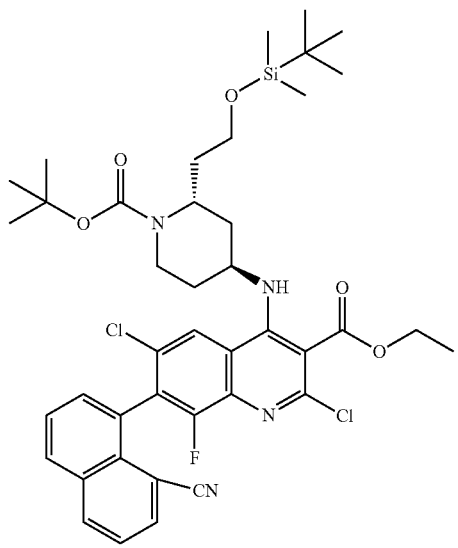 [SMILES: CCOC(=O)c1c(Cl)nc2c(F)c(-c3cccc4cccc(C#N)c34)c(Cl)cc2c1N[C@H]1CCN(C(=O)OC(C)(C)C)[C@H](CCO[Si](C)(C)C(C)(C)C)C1]

This compound was prepared according to the procedure described in Example 1a and Example 1b, in Step 10 replacing ethyl 2,4,6-trichloro-7-(8-cyanoisoquinolin-1-yl)-8-fluoroquinoline-3-carboxylate with ethyl 2,4,6-trichloro-7-(8-cyanonaphthalen-1-yl)-8-fluoroquinoline-3-carboxylate. LC-MS calculated for $C_{41}H_{50}Cl_2FN_4O_5Si$ (M+H)$^+$: m/z=795.3, 797.3; found 795.5, 797.5.

Step 7. tert-butyl (2S,4S)-2-(2-((tert-butyldimethyl-silyl)oxy)ethyl)-4-((2,6-dichloro-7-(8-cyanonaphtha-len-1-yl)-8-fluoro-3-(hydroxymethyl)quinolin-4-yl)amino)piperidine-1-carboxylate

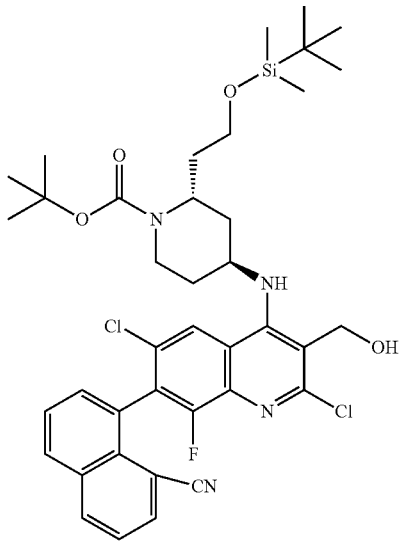 [SMILES: CC(C)(C)OC(=O)N1CC[C@H](Nc2c(CO)c(Cl)nc3c(F)c(-c4cccc5cccc(C#N)c45)c(Cl)cc23)C[C@H]1CCO[Si](C)(C)C(C)(C)C]

This compound was prepared according to the procedure described in Example 1a and Example 1b, in Step 11 replacing ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanoisoquinolin-1-yl)-8-fluoroquinoline-3-carboxylate with ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanonaphthalen-1-yl)-8-fluoroquinoline-3-carboxylate. LC-MS calculated for $C_{39}H_{48}Cl_2FN_4O_4Si$ $(M+H)^+$: m/z=753.3, 755.3; found 753.4, 755.5.

Step 8. tert-butyl (2S,4S)-2-(2-((tert-butyldimethyl-silyl)oxy)ethyl)-4-((2,6-dichloro-7-(8-cyanonaphtha-len-1-yl)-8-fluoro-3-formylquinolin-4-yl)amino)piperidine-1-carboxylate

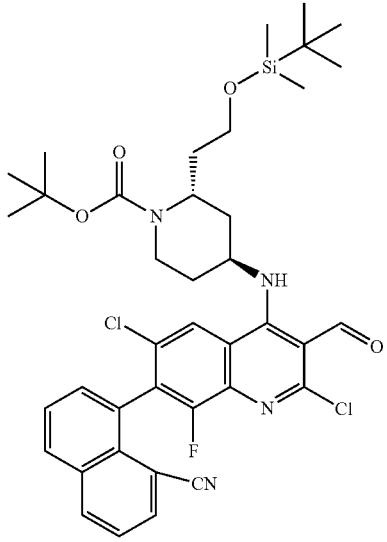 [SMILES: CC(C)(C)OC(=O)N1CC[C@H](Nc2c(C=O)c(Cl)nc3c(F)c(-c4cccc5cccc(C#N)c45)c(Cl)cc23)C[C@H]1CCO[Si](C)(C)C(C)(C)C]

This compound was prepared according to the procedure described in Example 1a and Example 1b, in Step 12 replacing tert-butyl (2S,4S)-2-(2-((tert-butyldimethylsilyl)oxy)ethyl)-4-((2,6-dichloro-7-(8-cyanoisoquinolin-1-yl)-8-fluoro-3-(hydroxymethyl)quinolin-4-yl)amino)piperidine-1-carboxylate with tert-butyl (2S,4S)-2-(2-((tert-butyldimethylsilyl)oxy)ethyl)-4-((2,6-dichloro-7-(8-cyanonaphthalen-1-yl)-8-fluoro-3-(hydroxymethyl)quinolin-4-yl)amino)piperidine-1-carboxylate. LC-MS calculated for $C_{39}H_6Cl_2FN_4O_4Si$ $(M+H)^+$: m/z=751.3, 753.3; found 751.4, 753.4.

Step 9. tert-butyl (2S,4S)-2-(2-((tert-butyldimethyl-silyl)oxy)ethyl)-4-((2,6-dichloro-7-(8-cyanonaphtha-len-1-yl)-8-fluoro-3-((E)-(hydroxyimino)methyl)quinolin-4-yl)amino)piperidine-1-carboxylate

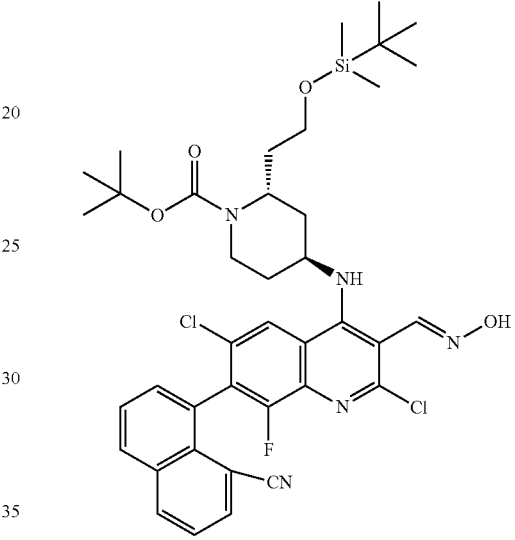

This compound was prepared according to the procedure described in Example 1a and Example 1b, in Step 13 replacing tert-butyl (2S,4S)-2-(2-((tert-butyldimethylsilyl)oxy)ethyl)-4-((2,6-dichloro-7-(8-cyanoisoquinolin-1-yl)-8-fluoro-3-formylquinolin-4-yl)amino)piperidine-1-carboxylate with tert-butyl (2S,4S)-2-(2-((tert-butyldimethylsilyl)oxy)ethyl)-4-((2,6-dichloro-7-(8-cyanonaphthalen-1-yl)-8-fluoro-3-formylquinolin-4-yl)amino)piperidine-1-carboxylate. LC-MS calculated for $C_{39}H_{47}Cl_2FN_5O_4Si$ $(M+H)^+$: m/z=766.3, 768.3; found 766.4, 768.4.

Step 10. tert-butyl (2S,4S)-2-(2-((tert-butyldimeth-ylsilyl)oxy)ethyl)-4-(4,8-dichloro-7-(8-cyanonaph-thalen-1-yl)-6-fluoro-1H-pyrazolo[4,3-c]quinolin-1-yl)piperidine-1-carboxylate

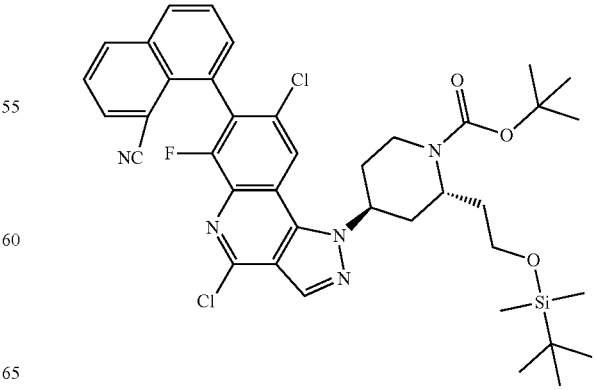

This compound was prepared according to the procedure described in Example 1a and Example 1b, in Step 14 replacing (tert-butyl (2S,4S)-2-(2-((tert-butyldimethylsilyl)oxy)ethyl)-4-((2,6-dichloro-7-(8-cyanoisoquinolin-1-yl)-8-fluoro-3-((E)-(hydroxyimino)methyl)quinolin-4-yl)amino)piperidine-1-carboxylate with tert-butyl (2S,4S)-2-(2-((tert-butyldimethylsilyl)oxy)ethyl)-4-((2,6-dichloro-7-(8-cyanonaphthalen-1-yl)-8-fluoro-3-((E)-(hydroxyimino)methyl)quinolin-4-yl)amino)piperidine-1-carboxylate. LC-MS calculated for $C_{39}H_{45}Cl_2FN_5O_3Si$ (M+H)$^+$: m/z=748.3, 750.3; found 748.4, 750.4.

Step 11. tert-butyl (2S,4S)-2-(2-((tert-butyldimethylsilyl)oxy)ethyl)-4-(8-chloro-7-(8-cyanonaphthalen-1-yl)-6-fluoro-4-(methylthio)-1H-pyrazolo[4,3-c]quinolin-1-yl)piperidine-1-carboxylate

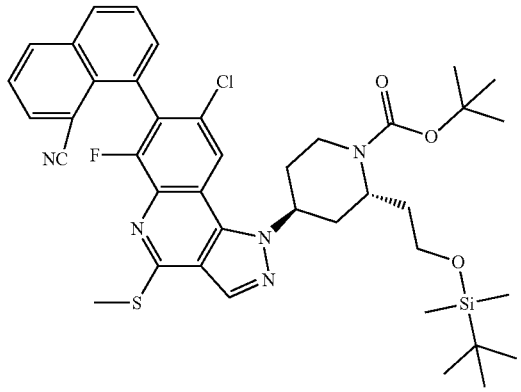 [SMILES: CSc1nc2c(F)c(-c3cccc4cccc(C#N)c34)c(Cl)cc2c2c1cnn2[C@H]1CCN(C(=O)OC(C)(C)C)[C@H](CCO[Si](C)(C)C(C)(C)C)C1]

This compound was prepared according to the procedure described in in Example 1a and Example 1b, in Step 15 replacing tert-butyl (2S,4S)-2-(2-((tert-butyldimethylsilyl)oxy)ethyl)-4-(4,8-dichloro-7-(8-cyanoisoquinolin-1-yl)-6-fluoro-1H-pyrazolo[4,3-c]quinolin-1-yl)piperidine-1-carboxylate with tert-butyl (2S,4S)-2-(2-((tert-butyldimethylsilyl)oxy)ethyl)-4-(4,8-dichloro-7-(8-cyanonaphthalen-1-yl)-6-fluoro-1H-pyrazolo[4,3-c]quinolin-1-yl)piperidine-1-carboxylate. LC-MS calculated for $C_{40}H_{48}ClFN_5O_3SSi$ (M+H)$^+$: m/z=760.3; found 760.3.

Step 12. tert-butyl (2S,4S)-4-(8-chloro-7-(8-cyanonaphthalen-1-yl)-6-fluoro-4-(methylthio)-1H-pyrazolo[4,3-c]quinolin-1-yl)-2-(2-hydroxyethyl)piperidine-1-carboxylate

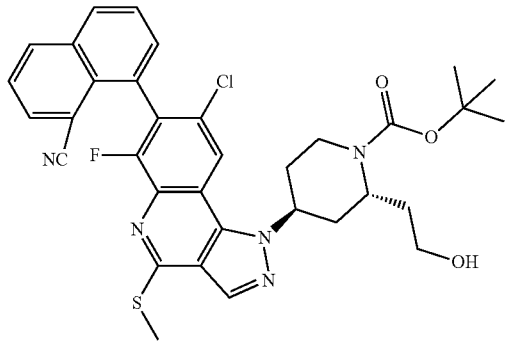 [SMILES: CSc1nc2c(F)c(-c3cccc4cccc(C#N)c34)c(Cl)cc2c2c1cnn2[C@H]1CCN(C(=O)OC(C)(C)C)[C@H](CCO)C1]

This compound was prepared according to the procedure described in Example 1a and Example 1b, in Step 16 replacing tert-butyl (2S,4S)-2-(2-((tert-butyldimethylsilyl)oxy)ethyl)-4-(8-chloro-7-(8-cyanoisoquinolin-1-yl)-6-fluoro-4-(methylthio)-1H-pyrazolo[4,3-c]quinolin-1-yl)piperidine-1-carboxylate with tert-butyl (2S,4S)-2-(2-((tert-butyldimethylsilyl)oxy)ethyl)-4-(8-chloro-7-(8-cyanonaphthalen-1-yl)-6-fluoro-4-(methylthio)-1H-pyrazolo[4,3-c]quinolin-1-yl)piperidine-1-carboxylate. LC-MS calculated for $C_{34}H_{34}ClFN_5O_3S$ (M+H)$^+$: m/z=646.2; found 646.2.

Step 13. tert-butyl (2S,4S)-4-(8-chloro-7-(8-cyanonaphthalen-1-yl)-6-fluoro-4-(methylthio)-1H-pyrazolo[4,3-c]quinolin-1-yl)-2-(cyanomethyl)piperidine-1-carboxylate

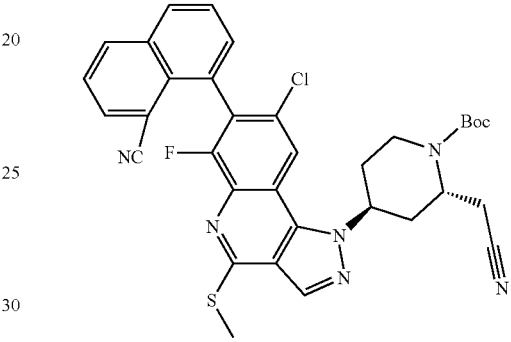

This compound was prepared according to the procedure described in Example 1a and Example 1b, in Step 17 replacing tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(2-hydroxyethyl)piperidine-1-carboxylate with tert-butyl (2S,4S)-4-(8-chloro-7-(8-cyanonaphthalen-1-yl)-6-fluoro-4-(methylthio)-1H-pyrazolo[4,3-c]quinolin-1-yl)-2-(2-hydroxyethyl)piperidine-1-carboxylate. LC-MS calculated for $C_{34}H_{31}ClFN_6O_2S$ (M+H)$^+$: m/z=641.2; found 641.2.

Step 14. 8-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile

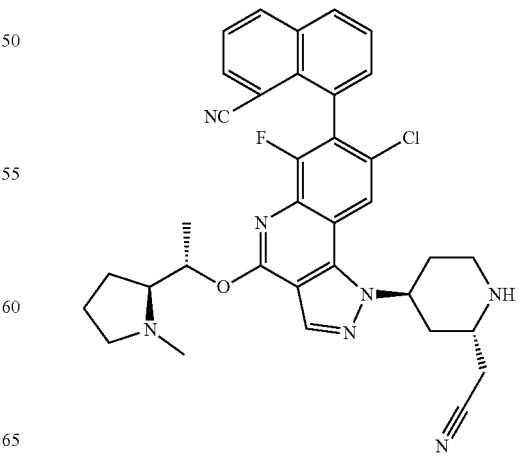

This compound was prepared according to the procedure described in Example 1a and Example 1b, in Step 18 replacing of tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(cyanomethyl)piperidine-1-carboxylate with tert-butyl (2S,4S)-4-(8-chloro-7-(8-cyanonaphthalen-1-yl)-6-fluoro-4-(methylthio)-1H-pyrazolo[4,3-c]quinolin-1-yl)-2-(cyanomethyl)piperidine-1-carboxylate. LC-MS calculated for C$_{35}$H$_{34}$ClFN$_7$O (M+H)$^+$: m/z=622.2; found 622.2.

Step 15. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)-1-naphthonitrile To a solution of 2-fluoroacrylic acid (0.9 mg, 9.88 μmol) and 8-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile bis(2,2,2-trifluoroacetate) (7.0 mg, 8.23 μmol) in DMF (1.0 ml) was added HATU (3.9 mg, 10.3 μmol) and DIEA (1.4 μl, 8.23 μmol). The resulting mixture was stirred at rt for 2 h. The reaction was diluted with methanol and 1 N HCl (0.1 mL) then purified using prep-LCMS (XBridge C18 column, eluting with a gradient of acetonitrile/water containing 0.1% TFA, at flow rate of 60 mL/min) to afford the desired diastereomer 1.

Diastereomer 2 was synthesized in similar way using 8-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile bis(2,2,2-trifluoroacetate) (peak2 from last step).

Example 5a. Diastereomer 1. Peak 1. LCMS calculated for C$_{37}$H$_{36}$ClFN$_7$O$_2$(M+H)$^+$ m/z=664.3 found 664.3.

Example 5b. Diastereomer 2. Peak 2. LCMS calculated for C$_{37}$H$_{36}$ClFN$_7$O$_2$(M+H)$^+$ m/z=664.3 found 664.3. $^1$H NMR (600 MHz, DMSO) b 9.86 (m, 1H), 8.52 (m, 3H), 8.34 (m, 1H), 8.17 (m, 1H), 7.88 (m, 1H), 7.78 (m, 1H), 7.73 (m, 1H), 5.83 (m, 1H), 5.50 (m, 1H), 5.39 (m, 1H), 5.27 (s, 1H), 3.84 (m, 1H), 3.56 (m, 1H), 3.30 (m, 2H), 3.18 (m, 1H), 3.09 (m, 3H), 2.30 (m, 1H), 2.11 (m, 1H), 1.92 (m, 2H), 1.53 (d, J=6.0 Hz, 3H).

Example 6a and Example 6b. 8-(8-chloro-1-((2S,4S)-2-(cyanomethyl)-1-((E)-4-methoxybut-2-enoyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile

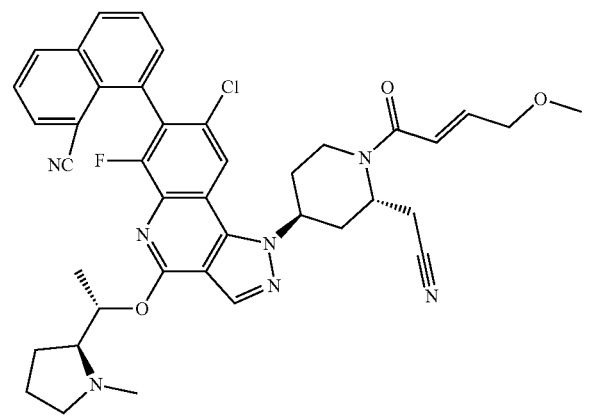 [SMILES: COC/C=C/C(=O)N1CC[C@H](n2ncc3c(O[C@@H](C)[C@@H]4CCCN4C)nc4c(F)c(-c5cccc6cccc(C#N)c56)c(Cl)cc4c32)C[C@H]1CC#N]

This compound was prepared according to the procedure described in Example 5a and Example 5b, step 15, replacing 2-fluoroacrylic acid with (E)-4-methoxybut-2-enoic acid. LCMS calculated for C$_{40}$H$_{40}$ClFN$_7$O$_3$(M+H)$^+$: m/z=720.3; found: 720.3.

Example 7 8-(1-((2S,4S)-1-(but-2-ynoyl)-2-(cyanomethyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile

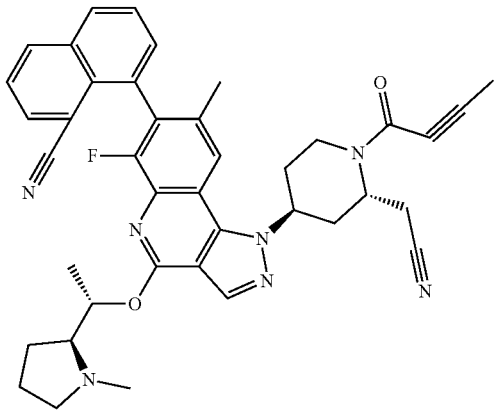 [SMILES: CC#CC(=O)N1CC[C@H](n2ncc3c(O[C@@H](C)[C@@H]4CCCN4C)nc4c(F)c(-c5cccc6cccc(C#N)c56)c(C)cc4c32)C[C@H]1CC#N]

Step 1: ethyl 7-bromo-2,4-dichloro-8-fluoro-6-iodoquinoline-3-carboxylate

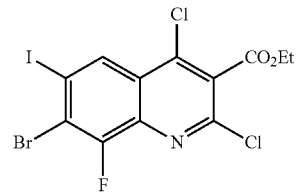 [SMILES: CCOC(=O)c1c(Cl)nc2c(F)c(Br)c(I)cc2c1Cl]

The title compound was synthesized according to the procedure described for Example 4a and Example 4b from step 1 to 3, utilizing 2-amino-4-bromo-3-fluoro-5-iodobenzoic acid instead of 2-amino-4-bromo-5-chloro-3-fluorobenzoic acid in Step 1. LCMS calculated for C$_{12}$H$_7$BrCl$_2$FINO$_2$ (M+H)$^+$ m/z=491.80, 493.80; found 491.80, 493.80.

Step 2. ethyl 7-bromo-4-(((2S,4S)-1-(tert-butoxycarbonyl)-2-(2-((tert-butyldimethylsilyl)oxy)ethyl)piperidin-4-yl)amino)-2-chloro-8-fluoro-6-iodoquinoline-3-carboxylate

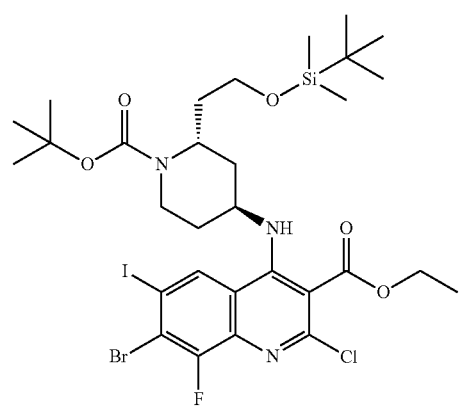 [SMILES: CCOC(=O)c1c(Cl)nc2c(F)c(Br)c(I)cc2c1N[C@H]1CCN(C(=O)OC(C)(C)C)[C@H](CCO[Si](C)(C)C(C)(C)C)C1]

This compound was prepared according to the procedure described in Example 4a and Example 4b, in Step 10 replacing ethyl 7-bromo-2,4,6-trichloro-8-fluoroquinoline-3-carboxylate with ethyl 7-bromo-2,4-dichloro-8-fluoro-6-iodoquinoline-3-carboxylate. LC-MS calculated for $C_{30}H_{44}BrClFIN_3O_5Si$ (M+H)$^+$: m/z=814.1, 816.1; found 814.1, 816.2.

Step 3. tert-butyl (2S,4S)-4-((7-bromo-2-chloro-8-fluoro-3-(hydroxymethyl)-6-iodoquinolin-4-yl)amino)-2-(2-((tert-butyldimethylsilyl)oxy)ethyl)piperidine-1-carboxylate

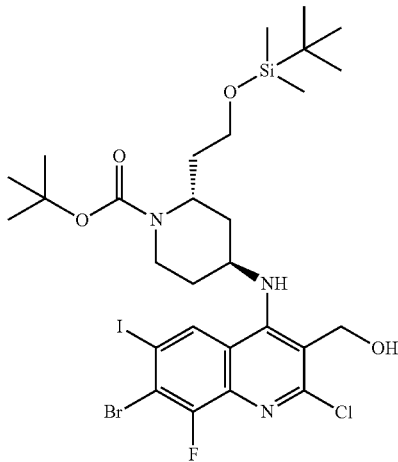 [SMILES: CC(C)(C)OC(=O)N1CC[C@H](Nc2c(CO)c(Cl)nc3c(F)c(Br)c(I)cc23)C[C@H]1CCO[Si](C)(C)C(C)(C)C]

This compound was prepared according to the procedure described in Example 4a and Example 4b, in Step 11 replacing ethyl 7-bromo-4-(((2S,4S)-1-(tert-butoxycarbonyl)-2-(2-((tert-butyldimethylsilyl)oxy)ethyl)piperidin-4-yl)amino)-2,6-dichloro-8-fluoroquinoline-3-carboxylate with ethyl 7-bromo-4-(((2S,4S)-1-(tert-butoxycarbonyl)-2-(2-((tert-butyldimethylsilyl)oxy)ethyl)piperidin-4-yl)amino)-2-chloro-8-fluoro-6-iodoquinoline-3-carboxylate. LC-MS calculated for $C_{28}H_{42}BrClFIN_3O_4Si$ (M+H)$^+$: m/z=772.1, 774.1; found 772.1, 774.1.

Step 4. tert-butyl (2S,4S)-4-((7-bromo-2-chloro-8-fluoro-3-formyl-6-iodoquinolin-4-yl)amino)-2-(2-((tert-butyldimethylsilyl)oxy)ethyl)piperidine-1-carboxylate

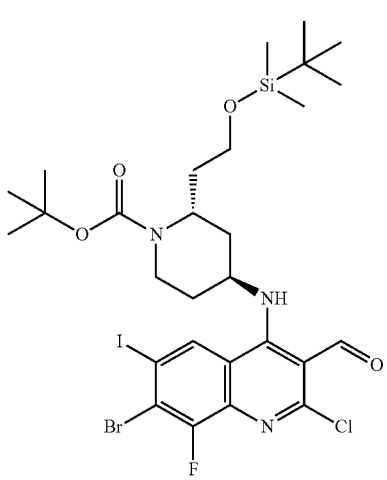 [SMILES: CC(C)(C)OC(=O)N1CC[C@H](Nc2c(C=O)c(Cl)nc3c(F)c(Br)c(I)cc23)C[C@H]1CCO[Si](C)(C)C(C)(C)C]

This compound was prepare according to the procedure described in Example 4a and Example 4b, in Step 12 replacing tert-butyl (2S,4S)-4-((7-bromo-2,6-dichloro-8-fluoro-3-(hydroxymethyl)quinolin-4-yl)amino)-2-(2-((tert-butyldimethylsilyl)oxy)ethyl)piperidine-1-carboxylate with tert-butyl (2S,4S)-4-((7-bromo-2-chloro-8-fluoro-3-(hydroxymethyl)-6-iodoquinolin-4-yl)amino)-2-(2-((tert-butyldimethylsilyl)oxy)ethyl)piperidine-1-carboxylate. LC-MS calculated for $C_{28}H_{40}BrClFIN_3O_4Si$ (M+H)$^+$: m/z=770.1, 772.1; found 770.1, 772.1.

Step 5. tert-butyl (2S,4S)-4-((7-bromo-2-chloro-8-fluoro-3-((E)-(hydroxyimino)methyl)-6-iodoquinolin-4-yl)amino)-2-(2-((tert-butyldimethylsilyl)oxy)ethyl)piperidine-1-carboxylate

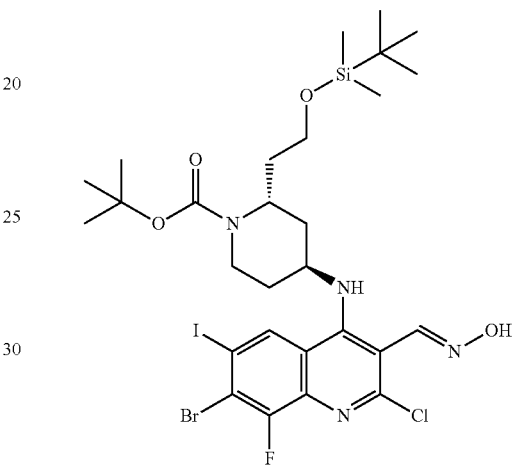

This compound was prepared according to the procedure described in Example 4a and Example 4b, in Step 13 replacing tert-butyl (2S,4S)-4-((7-bromo-2,6-dichloro-8-fluoro-3-formylquinolin-4-yl)amino)-2-(2-((tert-butyldimethylsilyl)oxy)ethyl) piperidine-1-carboxylate with tert-butyl (2S,4S)-4-((7-bromo-2-chloro-8-fluoro-3-formyl-6-iodoquinolin-4-yl)amino)-2-(2-((tert-butyldimethylsilyl)oxy)ethyl)piperidine-1-carboxylate. LC-MS calculated for $C_{28}H_{41}BrClFIN_4O_4Si$ (M+H)$^+$: m/z=785.1, 787.1; found 785.2, 787.2.

Step 6. tert-butyl (2S,4S)-4-(7-bromo-4-chloro-6-fluoro-8-iodo-1H-pyrazolo[4,3-c]quinolin-1-yl)-2-(2-((tert-butyldimethylsilyl)oxy)ethyl)piperidine-1-carboxylate

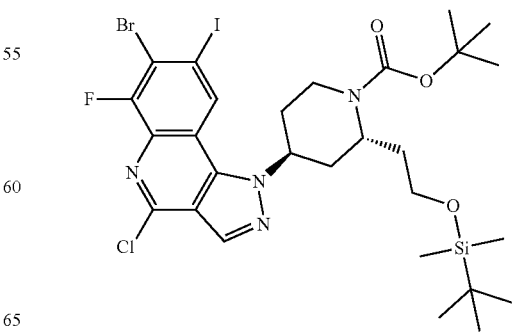

This compound was prepared according to the procedure described in Example 4a and Example 4b, in Step 14 replacing (tert-butyl (2S,4S)-4-((7-bromo-2,6-dichloro-8-fluoro-3-((E)-(hydroxyimino)methyl)quinolin-4-yl)amino)-2-(2-((tert-butyldimethylsilyl)oxy)ethyl)piperidine-1-carboxylate with tert-butyl (2S,4S)-4-((7-bromo-2-chloro-8-fluoro-3-((E)-(hydroxyimino)methyl)-6-iodoquinolin-4-yl)amino)-2-(2-((tert-butyldimethylsilyl)oxy)ethyl)piperidine-1-carboxylate. LC-MS calculated for $C_{28}H_{39}BrClFIN_4O_3Si$ (M+H)$^+$: m/z=767.1, 769.1; found 767.1, 769.1.

Step 7. tert-butyl (2S,4S)-4-(7-bromo-6-fluoro-8-iodo-4-(methylthio)-1H-pyrazolo[4,3-c]quinolin-1-yl)-2-(2-((tert-butyldimethylsilyl)oxy)ethyl)piperidine-1-carboxylate

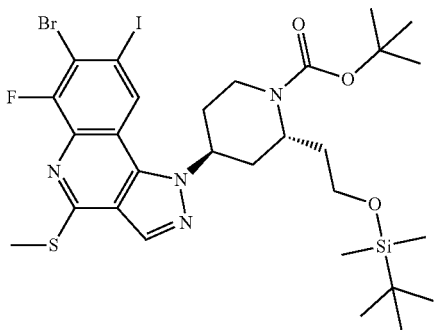 [SMILES: CSc1nc2c(F)c(Br)c(I)cc2c2c1cnn2[C@H]1CCN(C(=O)OC(C)(C)C)[C@H](CCO[Si](C)(C)C(C)(C)C)C1]

This compound was prepared according to the procedure described in Example 4a and Example 4b, in Step 15 replacing of tert-butyl (2S,4S)-4-(7-bromo-4,8-dichloro-6-fluoro-1H-pyrazolo[4,3-c]quinolin-1-yl)-2-(2-((tert-butyldimethylsilyl)oxy)ethyl)piperidine-1-carboxylate with tert-butyl (2S,4S)-4-(7-bromo-4-chloro-6-fluoro-8-iodo-1H-pyrazolo[4,3-c]quinolin-1-yl)-2-(2-((tert-butyldimethylsilyl)oxy)ethyl)piperidine-1-carboxylate. LC-MS calculated for $C_{29}H_{42}BrFIN_4O_3SSi$ (M+H)$^+$: m/z=779.1, 781.1; found 779.1, 781.1.

Step 8. tert-butyl (2S,4S)-4-(7-bromo-6-fluoro-8-iodo-4-(methylthio)-1H-pyrazolo[4,3-c]quinolin-1-yl)-2-(2-hydroxyethyl)piperidine-1-carboxylate

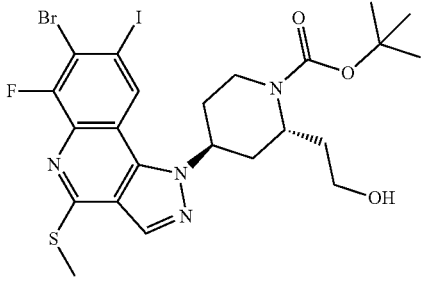 [SMILES: CSc1nc2c(F)c(Br)c(I)cc2c2c1cnn2[C@H]1CCN(C(=O)OC(C)(C)C)[C@H](CCO)C1]

This compound was prepared according to the procedure described in Example 4a and Example 4b, in Step 16 replacing of tert-butyl (2S,4S)-4-(7-bromo-8-chloro-6-fluoro-4-(methylthio)-1H-pyrazolo[4,3-c]quinolin-1-yl)-2-(2-((tert-butyldimethylsilyl)oxy)ethyl)piperidine-1-carboxylate with tert-butyl (2S,4S)-4-(7-bromo-6-fluoro-8-iodo-4-(methylthio)-1H-pyrazolo[4,3-c]quinolin-1-yl)-2-(2-((tert-butyldimethylsilyl)oxy)ethyl)piperidine-1-carboxylate. LC-MS calculated for $C_{23}H_{28}BrFIN_4O_3S$ (M+H)$^+$: m/z=665.0, 667.0; found 665.1, 667.1.

Step 9. tert-butyl (2S,4S)-4-(7-bromo-6-fluoro-8-iodo-4-(methylthio)-1H-pyrazolo[4,3-c]quinolin-1-yl)-2-(cyanomethyl)piperidine-1-carboxylate

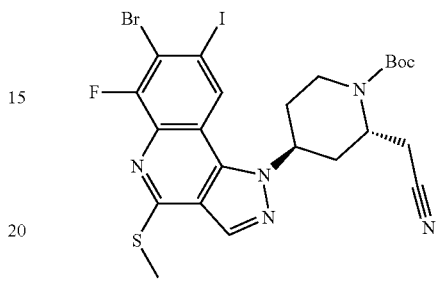

This compound was prepared according to the procedure described in Example 4a and Example 4b, in Step 17 replacing of of tert-butyl (2S,4S)-4-(7-bromo-8-chloro-6-fluoro-4-(methylthio)-1H-pyrazolo[4,3-c]quinolin-1-yl)-2-(2-hydroxyethyl)piperidine-1-carboxylate with tert-butyl (2S,4S)-4-(7-bromo-6-fluoro-8-iodo-4-(methylthio)-1H-pyrazolo[4,3-c]quinolin-1-yl)-2-(2-hydroxyethyl)piperidine-1-carboxylate. LC-MS calculated for $C_{23}H_{25}BrFIN_5O_2S$ (M+H)$^+$: m/z=660.0, 662.0; found 660.0, 662.0.

Step 10. tert-butyl (2S,4S)-4-(7-bromo-6-fluoro-8-methyl-4-(methylthio)-1H-pyrazolo[4,3-c]quinolin-1-yl)-2-(cyanomethyl) piperidine-1-carboxylate

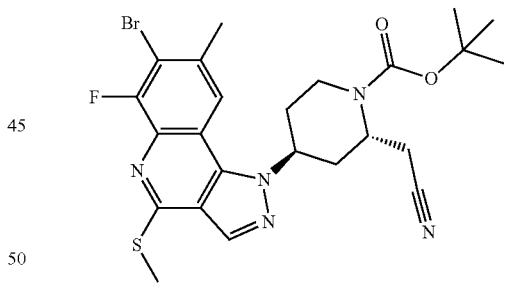

To a solution of tert-butyl (2S,4S)-4-(7-bromo-6-fluoro-8-iodo-4-(methylthio)-1H-pyrazolo[4,3-c]quinolin-1-yl)-2-(cyanomethyl)piperidine-1-carboxylate (2.75 g, 4.16 mmol) in 1,4-dioxane (36 ml) was added water (6.0 ml), methylboronic acid (1.496 g, 24.99 mmol), $K_2CO_3$ (1.151 g, 8.33 mmol) and Pd(PPh$_3$)$_2$Cl$_2$ (0.292 g, 0.416 mmol) at rt. The reaction mixture was stirred at 90° C. for 10 h under N$_2$ atmosphere. After the reaction was complete, the reaction mixture was quenched with water and extracted with EtOAc. The organic phase was dried over anhydrous Na$_2$SO$_4$ and concentrated and then purified by column chromatography on silica gel (Eluents:Hexanes:Ethyl acetate=5:1) to get compound (1.9 g, 83%) as a white solid. LC-MS calculated for $C_{24}H_{28}BrFN_5O_2S$ (M+H)$^+$: m/z=548.1, 550.1; found 548.2, 550.2.

Step 11. tert-butyl (2S,4S)-4-(7-bromo-6-fluoro-8-methyl-4-((S)-1-((S)-1-methylpyrrolidin-2-yl)ethoxy)-1H-pyrazolo[4,3-c]quinolin-1-yl)-2-(cyanomethyl)piperidine-1-carboxylate

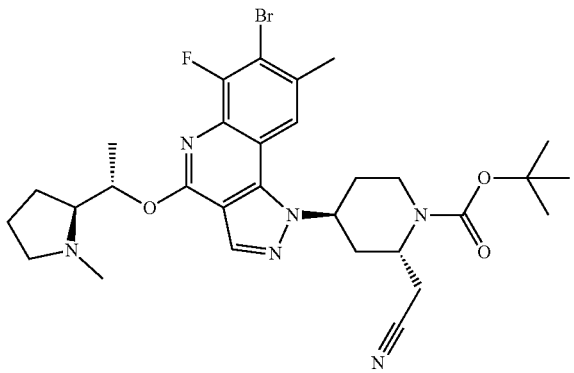 [SMILES: Cc1cc2c(nc(O[C@@H](C)[C@@H]3CCCN3C)c3cnn([C@H]4CCN(C(=O)OC(C)(C)C)[C@H](CC#N)C4)c32)c(F)c1Br]

m-CPBA (57.9 mg, 0.335 mmol) was added to a solution of tert-butyl (2S,4S)-4-(7-bromo-6-fluoro-8-methyl-4-(methylthio)-1H-pyrazolo[4,3-c]quinolin-1-yl)-2-(cyanomethyl)piperidine-1-carboxylate (160 mg, 0.29 mmol) in $CH_2Cl_2$ (2.9 ml) at 0° C. and then the reaction was stirred at this temperature for 20 min. The reaction was quenched by adding sat'd $Na_2S_2O_3$, diluted with ethyl acetate and washed with sat'd $NaHCO_3$, brine, filtered, dried and concentrated. 1.0 M LiHMDS in THF (753 μl, 0.753 mmol) was added to a solution of (S)-1-((S)-1-methylpyrrolidin-2-yl)ethan-1-ol (97 mg, 0.753 mmol) in THF (1 mL). The resulting mixture was stirred at rt for 30 min. A solution of tert-butyl (2S,4S)-4-(7-bromo-6-fluoro-8-methyl-4-(methylsulfinyl)-1H-pyrazolo[4,3-c]quinolin-1-yl)-2-(cyanomethyl)piperidine-1-carboxylate (170 mg, 0.301 mmol) in THF (2.0 ml) was added to reaction vial and then the reaction was stirred at room temperature for 2 h. The reaction mixture was diluted with ethyl acetate and water. The organic layer was dried over $Na_2SO_4$, filtered and concentrated. The residue was purified with silica gel column (eluting with a gradient of 0-20% methanol in DCM) to give the desired product as yellow foam (150 mg, 79%). LC-MS calculated for $C_{30}H_{39}BrFN_6O_3(M+H)^+$: m/z=629.2, 631.2; found 629.3, 631.3.

Step 12. tert-butyl (2S,4S)-2-(cyanomethyl)-4-(7-(8-cyanonaphthalen-1-yl)-6-fluoro-8-methyl-4-((S)-1-((S)-1-methylpyrrolidin-2-yl)ethoxy)-1H-pyrazolo[4,3-c]quinolin-1-yl)piperidine-1-carboxylate

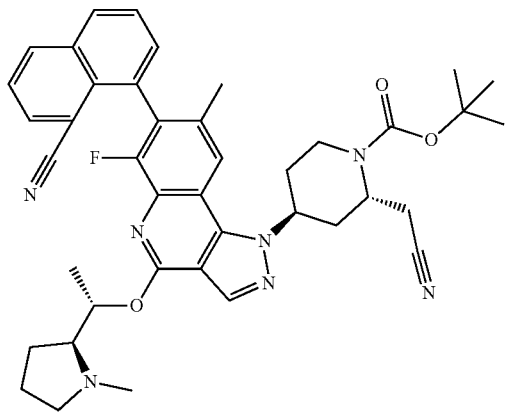 [SMILES: Cc1cc2c(nc(O[C@@H](C)[C@@H]3CCCN3C)c3cnn([C@H]4CCN(C(=O)OC(C)(C)C)[C@H](CC#N)C4)c32)c(F)c1-c1cccc2cccc(C#N)c12]

A mixture of tert-butyl (2S,4S)-4-(7-bromo-6-fluoro-8-methyl-4-((S)-1-((S)-1-methylpyrrolidin-2-yl)ethoxy)-1H-pyrazolo[4,3-c]quinolin-1-yl)-2-(cyanomethyl)piperidine-1-carboxylate (150 mg, 0.238 mmol), 8-(4,4,5,5-tetramethyl-1,3,2-dioxaborolan-2-yl)-1-naphthonitrile (86 mg, 0.31 mmol), SPhos Pd G4 (19 mg, 0.024 mmol) and tripotassium phosphate hydrate (121 mg, 0.524 mmol) in 1,4-dioxane (2.0 mL)/water (0.400 mL) was stirred at 80° C. under $N_2$ atmosphere for 2 h. The solution was diluted with ethyl acetate and water. The organic layer was concentrated and the residue was purified with prep-LCMS (XBridge C18 column, eluting with a gradient of acetonitrile/water containing 0.1% TFA, at flow rate of 60 mL/min) to give the desired product as two peaks (105 mg, 63%).

Diastereomer 1. Peak 1. LC-MS calculated for $C_{41}H_{45}FN_7O_3(M+H)^+$: m/z=702.3; found 702.3.

Diastereomer 2. Peak 2. LC-MS calculated for $C_{41}H_{45}FN_7O_3(M+H)^+$: m/z=702.3; found 702.3.

Step 13. 8-(1-((2S,4S)-2-(cyanomethyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile

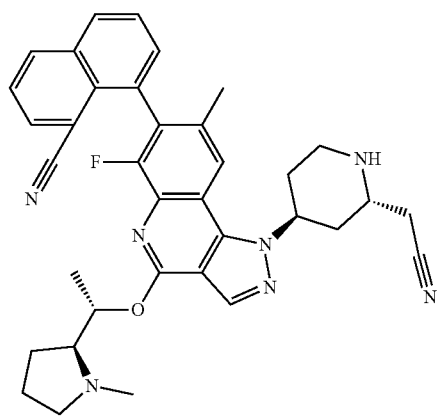 [SMILES: Cc1cc2c(nc(O[C@@H](C)[C@@H]3CCCN3C)c3cnn([C@H]4CCN[C@H](CC#N)C4)c32)c(F)c1-c1cccc2cccc(C#N)c12]

Two Diastereomers from last step were treated with 1:1 DCM/TFA (2 mL) for 40 min, The volatiles were removed in vacuo and residue was used in the next step as is.

Diastereomer 1. Peak 1. LC-MS calculated for $C_{36}H_{37}FN_7O$ $(M+H)^+$: m/z=602.3; found 602.3.

Diastereomer 2. Peak 2. LC-MS calculated for $C_{36}H_{37}FN_7O$ $(M+H)^+$: m/z=602.3; found 602.3.

Step 14. 8-(1-((2S,4S)-1-(but-2-ynoyl)-2-(cyanomethyl)piperidin-4-yl)-6-fluoro-8-methyl-4-((S)-1-((S)-1-methylpyrrolidin-2-yl)ethoxy)-1H-pyrazolo[4,3-c]quinolin-7-yl)-1-naphthonitrile To a solution of but-2-ynoic acid (0.730 mg, 8.68 μmol) and 8-(1-((2S,4S)-2-(cyanomethyl)piperidin-4-yl)-6-fluoro-8-methyl-4-(((S)-1-methylpyrrolidin-2-yl)methoxy)-1H-pyrazolo[4,3-c]quinolin-7-yl)-1-naphthonitrile bis(2,2,2-trifluoroacetate) (6.0 mg, 7.36 μmol) (Diastereomer 2 peak 2 from last step) in DMF (1.0 ml) was added HATU (3.5 mg, 9.19 μmol) and DIEA (6.4 μl, 0.037 mmol). The resulting mixture was stirred at rt for 1 h. The reaction was diluted with methanol and 1 N HCl (0.1 mL) and purified using prep-LCMS (XBridge C18 column, eluting with a gradient of acetonitrile/water containing 0.1% TFA, at flow rate of 60 mL/min) to afford the desired product (2.5 mg, 52%). LCMS calculated for $C_{40}H_{39}FN_7O_2(M+H)^+$ m/z=668.3; found 668.3.

Example A. GDP-GTP Exchange Assay

The inhibitor potency of the exemplified compounds was determined in a fluorescence based guanine nucleotide exchange assay, which measures the exchange of bodipy-GDP (fluorescently labeled GDP) for GppNHp (Non-hydrolyzable GTP analog) to generate the active state of KRAS in the presence of SOS1 (guanine nucleotide exchange factor). Inhibitors were serially diluted in DMSO and a volume of 0.1 µL was transferred to the wells of a black low volume 384-well plate. 5 µL/well volume of bodipy-loaded KRAS G12C diluted to 5 nM in assay buffer (25 mM Hepes pH 7.5, 50 mM NaCl, 10 mM MgCl2 and 0.01% Brij-35) was added to the plate and pre-incubated with inhibitor for 2 hours at ambient temperature. Appropriate controls (enzyme with no inhibitor or with a G12C inhibitor (AMG-510)) were included on the plate. The exchange was initiated by the addition of a 5 µL/well volume containing 1 mM GppNHp and 300 nM SOS1 in assay buffer. The 10 µL/well reaction concentration of the bodipy-loaded KRAS G12C, GppNHp, and SOS1 were 2.5 nM, 500 uM, and 150 nM, respectively. The reaction plates were incubated at ambient temperature for 2 hours, a time estimated for complete GDP-GTP exchange in the absence of inhibitor. For the KRAS G12D and G12V mutants, similar guanine nucleotide exchange assays were used with 2.5 nM as final concentration for the bodipy loaded KRAS proteins and with 4 hours and 3 hours incubation after adding GppNHp-SOS1 mixture for G12D and G12V respectively. A cyclic peptide described to selectively bind G12D mutant (Sakamoto et al., BBRC 484.3 (2017), 605-611) or internal compounds with confirmed binding were used as positive controls in the assay plates. Fluorescence intensities were measured on a PheraStar plate reader instrument (BMG Labtech) with excitation at 485 nm and emission at 520 nm.

Either GraphPad prism or Genedata Screener SmartFit was used to analyze the data. The $IC_{50}$ values were derived by fitting the data to a four parameter logistic equation producing a sigmoidal dose-response curve with a variable Hill coefficient.

The KRAS_G12C exchange assay $IC_{50}$ data, KRAS_G12C pERK assay $IC_{50}$ data, KRAS_G12C WB pERK assay $IC_{50}$ data are provided in Table 1 below. The symbol "†" indicates $IC_{50}$ ≤100 nM, "††" indicates $IC_{50}$ >100 nM but ≤1 µM; and "†††" indicates $IC_{50}$ is >1 µM but ≤5 µM, "††††" indicts $IC_{50}$ is >5 µM but ≤10 µM. "NA" indicates that data is not available.

TABLE 1

| Ex. No. | G12C_exchange | G12C_pERK | G12C_WB_pERK |
|---|---|---|---|
| 1a | † | † | † |
| 1b | † | NA | NA |
| 2a | † | † | † |
| 2b | † | † | NA |
| 3a | † | † | † |
| 3b | †† | NA | NA |
| 4a | † | † | † |
| 4b | ††† | NA | NA |
| 5a | †† | NA | NA |
| 5b | † | † | † |
| 6a | † | NA | NA |
| 6b | † | † | † |
| 7 | † | † | † |

Example B: Luminescent Viability Assay

MIA PaCa-2 (KRAS G12C; ATCC® CRL-1420), NCI-H358 (KRAS G12C; ATCC® CRL-5807), A427 (KRAS G12D; ATCC® HTB53), HPAFII (KRAS G12D; ATCC® CRL-1997), YAPC (KRAS G12V; DSMZ ACC382), SW480 (KRAS G12V; ATCC® CRL-228) and NCI-H838 (KRAS WT; ATCC® CRL-5844) cells are cultured in RPMI 1640 media supplemented with 10% FBS (Gibco/Life Technologies). Eight hundred cells per well in RPMI 1640 media supplemented with 2% FBS are seeded into white, clear bottomed 384-well Costar tissue culture plates containing 50 nL dots of test compounds (final concentration is a 1:500 dilution, with a final concentration in 0.2% DMSO). Plates are incubated for 3 days at 370 C, 5% CO2. At the end of the assay, 25 ul/well of CellTiter-Glo reagent (Promega) is added. Luminescence is read after 15 minutes with a PHER-Astar (BMG). Data are analyzed in Genedata Screener using SmartFit for $IC_{50}$ values.

Example C: Cellular pERK HTRF Assay

MIA PaCa-2 (KRAS G12C; ATCC® CRL-1420), NCI-H358 (KRAS G12C; ATCC® CRL-5807), A427 (KRAS G12D; ATCC® HTB53), HPAFII (KRAS G12D; ATCC® CRL-1997), YAPC (KRAS G12V; DSMZ ACC382), SW480 (KRAS G12V; ATCC® CRL-228) and NCI-H838 (KRAS WT; ATCC® CRL-5844) cells are purchased from ATCC and maintained in RPMI 1640 media supplemented with 10% FBS (Gibco/Life Technologies). The cells are plated at 5000 cells per well (8 uL) into Greiner 384-well low volume, flat-bottom, and tissue culture treated white plates and incubated overnight at 370 C, 5% $CO_2$. The next morning, test compound stock solutions are diluted in media at 3× the final concentration and 4 uL are added to the cells, with a final concentration of 0.1% of DMSO. The cells are incubated with the test compounds for 4 hours (G12C and G12V) or 2 hrs (G12D) at 37° C., 5% $CO_2$. Four uL of 4×lysis buffer with blocking reagent (Cisbio) are added to each well and plates are rotated gently (300 rpm) for 30 minutes at room temperature. Four uL per well of Cisbio anti Phospho-ERK 1/2 d2 is mixed with anti Phospho-ERK 1/2 Cryptate (1:1), and added to each well, incubated overnight in the dark at room temperature. Plates are read on the Pherastar plate reader at 665 nm and 620 nm wavelengths. Data are analyzed in Genedata Screener using SmartFit for $IC_{50}$ values.

Example D: Whole Blood pERK1/2 HTRF Assay

MIA PaCa-2 cells (KRAS G12C; ATCC® CRL-1420), HPAF-II (KRAS G12D; ATCC® CRL-1997) and YAPC (KRAS G12V; DSMZ ACC382) are maintained in RPMI 1640 with 10% FBS (Gibco/Life Technologies). For MIA PaCa-2 assay, cells are seeded into 96 well tissue culture plates (Corning #3596) at 25000 cells per well in 100 uL media and cultured for 2 days at 37° C., 5% $CO_2$ before the assay. For HPAF-II and YAPC assay, cells are seeded in 96 well tissue culture plates at 50000 cells per well in 100 uL media and cultured for 1 day before the assay. Whole Blood are added to the 1 uL dots of compounds (prepared in DMSO) in 96 well plates and mixed gently by pipetting up and down so that the concentration of the compound in blood is 1× of desired concentration, in 0.5% DMSO. The media is aspirated from the cells and 50 uL per well of whole blood with test compound is added and incubated for 4 hours for MIA PaCa and YAPC assay; or 2 hours for HPAF-II assay, respectively at 37° C., 5% $CO_2$. After dumping the blood, the plates are gently washed twice by adding PBS to the side of the wells and dumping the PBS from the plate onto a paper towel, tapping the plate to drain well. Fifty ul/well of 1×lysis buffer #1 (Cisbio) with blocking reagent (Cisbio) and Benzonase nuclease (Sigma Cat #E1014-5KU, 1: 10000 final concentration) is then added and incubated at room temperature for 30 minutes with shaking (250 rpm). Following lysis, 16 uL of lysate is transferred into 384-well Greiner small volume white plate using an Assist Plus (Integra Biosciences, NH). Four uL of 1:1 mixture of anti Phospho-ERK 1/2 d2 and anti Phospho-ERK 1/2 Cryptate (Cisbio) is added to the wells using the Assist Plus and incubated at room temperature overnight in the dark. Plates are read on the Pherastar plate reader at 665 nm and 620 nm wavelengths. Data are analyzed in Genedata Screener using SmartFit for $IC_{50}$ values.

Example E: Ras Activation Elisa

The 96-Well Ras Activation ELISA Kit (Cell Biolabs Inc; #STA441) uses the Raf1 RBD (Rho binding domain) bound to a 96-well plate to selectively pull down the active form of Ras from cell lysates. The captured GTP-Ras is then detected by a pan-Ras antibody and HRP-conjugated secondary antibody.

MIA PaCa-2 (KRAS G12C; ATCC® CRL-1420), NCI-H358 (KRAS G12C; ATCC® CRL-5807), A427 (KRAS G12D; ATCC® HTB53), HPAFII (KRAS G12D; ATCC® CRL-1997), YAPC (KRAS G12V; DSMZ ACC382), SW480 (KRAS G12V; ATCC® CRL-228) and NCI-H838 (KRAS WT; ATCC® CRL-5844) cells are maintained in RPMI 1640 with 10% FBS (Gibco/Life Technologies). The cells are seeded into 96 well tissue culture plates (Corning #3596) at 25000 cells per well in 100 uL media and cultured for 2 days at 37° C., 5% $CO_2$ so that they are approximately 80% confluent at the start of the assay. The cells are treated with compounds for either 4 hours or overnight at 37° C., 5% $CO_2$. At the time of harvesting, the cells are washed with PBS, drained well and then lysed with 50 uL of the 1×Lysis buffer (provided by the kit) plus added Halt Protease and Phosphatase inhibitors (1:100) for 1 hour on ice.

The Raf-1 RBD is diluted 1:500 in Assay Diluent (provided in kit) and 100 μL of the diluted Raf-1 RBD is added to each well of the Raf-1 RBD Capture Plate. The plate is covered with a plate sealing film and incubated at room temperature for 1 hour on an orbital shaker. The plate is washed 3 times with 250 μL 1×Wash Buffer per well with thorough aspiration between each wash. 50 μL of Ras lysate sample (10-100 pg) is added per well in duplicate. A "no cell lysate" control is added in a couple of wells for background determination. 50 μL of Assay Diluent is added to all wells immediately to each well and the plate is incubated at room temperature for 1 hour on an orbital shaker. The plate is washed 5 times with 250 μL 1×Wash Buffer per well with thorough aspiration between each wash. 100 μL of the diluted Anti-pan-Ras Antibody is added to each well and the plate is incubated at room temperature for 1 hour on an orbital shaker. The plate is washed 5 times as previously. 100 μL of the diluted Secondary Antibody, HRP Conjugate is added to each well and the plate is incubated at room temperature for 1 hour on an orbital shaker. The plate is washed 5 times as previously and drained well. 100 μL of Chemiluminescent Reagent (provided in the kit) is added to each well, including the blank wells. The plate is incubated at room temperature for 5 minutes on an orbital shaker before the luminescence of each microwell is read on a plate luminometer. The % inhibition is calculated relative to the DMSO control wells after a background level of the "no lysate control" is subtracted from all the values. $IC_{50}$ determination is performed by fitting the curve of inhibitor percent inhibition versus the log of the inhibitor concentration using the GraphPad Prism 7 software.

Example F: Inhibition of RAS-RAF and PI3K-AKT Pathways

The cellular potency of compounds is determined by measuring phosphorylation of KRAS downstream effectors extracellular-signal-regulated kinase (ERK), ribosomal S6 kinase (RSK), AKT (also known as protein kinase B, PKB) and downstream substrate S6 ribosomal protein.

To measure phosphorylated extracellular-signal-regulated kinase (ERK), ribosomal S6 kinase (RSK), AKT and S6 ribosomal protein, cells (details regarding the cell lines and types of data produced are further detailed in Table 2) are seeded overnight in Corning 96-well tissue culture treated plates in RPMI medium with 10% FBS at $4 \times 10^4$ cells/well. The following day, cells are incubated in the presence or absence of a concentration range of test compounds for 4 hours at 37° C., 5% $CO_2$. Cells are washed with PBS and lysed with 1×lysis buffer (Cisbio) with protease and phosphatase inhibitors (Thermo Fisher, 78446). Ten or twenty pg of total protein lysates are subjected to SDS-PAGE and immunoblot analysis using following antibodies: phospho-ERK1/2-Thr202/Tyr204 (#9101L), total-ERK1/2 (#9102L), phosphor-AKT-Ser473 (#4060L), phospho-p90RSK-Ser380 (#11989S) and phospho-S6 ribosomal protein-Ser235/Ser236 (#2211S) are from Cell Signaling Technologies (Danvers, MA).

TABLE 2

| Cell Line | Histology | KRAS alteration | Readout |
|---|---|---|---|
| H358 | Lung | G12C | pERK, pAKT, p-S6, p-p90RSK |
| MIA PaCa-2 | Pancreas | G12C | pERK, pAKT, p-S6, p-p90RSK |
| HPAF II | Pancreas | G12D | pERK, pAKT, p-S6, p-p90RSK |
| A427 | Lung | G12D | pERK, pAKT, p-S6, p-p90RSK |
| AGS | Stomach | G12D | pERK, pAKT, p-S6, p-p90RSK |
| PaTu 8988s | Pancreas | G12V | pERK, pAKT, p-S6, p-p90RSK |
| H441 | Lung | G12V | pERK, pAKT, p-S6, p-p90RSK |
| YAPC | Pancreas | G12V | pERK, pAKT, p-S6, p-p90RSK |
| SW480 | Colorectal | G12V | pERK, pAKT, p-S6, p-p90RSK |

Example G: In Vivo Efficacy Studies

Mia-Paca-2 (KRAS G12C), H358 (KRAS G12C), HPAF-II (KRAS G12D), AGS (KRAS G12D), SW480 (KRAS G12V) or YAPC(KRAS G12V) human cancer cells are obtained from the American Type Culture Collection and maintained in RPMI media supplemented with 10% FBS. For efficacy studies experiments, 5×106 cells are inoculated subcutaneously into the right hind flank of 6- to 8-week-old BALB/c nude mice (Charles River Laboratories, Wilmington, MA, USA). When tumor volumes are approximately 150-250 mm3, mice are randomized by tumor volume and compounds are orally administered. Tumor volume is calculated using the formula (L×W2)/2, where L and W refer to the length and width dimensions, respectively. Tumor growth inhibition is calculated using the formula (1−(VT/VC))×100, where VT is the tumor volume of the treatment group on the last day of treatment, and VC is the tumor volume of the control group on the last day of treatment. Two-way analysis of variance with Dunnett's multiple comparisons test is used to determine statistical differences between treatment groups (GraphPad Prism). Mice are housed at 10-12 animals per cage, and are provided enrichment and exposed to 12-hour light/dark cycles. Mice whose tumor volumes exceeded limits (10% of body weight) are humanely euthanized by $CO_2$ inhalation. Animals are maintained in a barrier facility fully accredited by the Association for Assessment and Accreditation of Laboratory Animal Care, International. All of the procedures are conducted in accordance with the US Public Service Policy on Human Care and Use of Laboratory Animals and with Incyte Animal Care and Use Committee Guidelines.

Example H: Caco2 Assay

Caco-2 cells were grown at 37° C. in an atmosphere of 5% $CO_2$ in DMEM growth medium supplemented with 10% (v/v) fetal bovine serum, 1% (v/v) nonessential amino acids, penicillin (100 U/mL), and streptomycin (100 pg/mL). Confluent cell monolayers were subcultured every 7 days or 4 days for Caco-2 by treatment with 0.05% trypsin containing 1 µM EDTA. Caco-2 cells were seeded in 96-well Transwell plates. The seeding density for Caco-2 cells was 14,000 cells/well. DMEM growth medium was replaced every other day after seeding. Cell monolayers were used for transport assays between 22 and 25 days for Caco-2 cells.

Cell culture medium was removed and replaced with HBSS. To measure the TEER, the HBSS was added into the donor compartment (apical side) and receiver compartment (basolateral side). The TEER was measured by using a REMS Autosampler to ensure the integrity of the cell monolayers. Caco-2 cell monolayers with TEER values 300 $\Omega \cdot cm^2$ were used for transport experiments. To determine the $P_{app}$ in the absorptive direction (A-B), solution of test compound (50 µM) in HBSS was added to the donor compartment (apical side), while HBSS solution with 4% BSA was added to the receiver compartment (basolateral side). The apical volume was 0.075 mL, and the basolateral volume was 0.25 mL. The incubation period was 120 minutes at 37° C. in an atmosphere of 5% $CO_2$. At the end of the incubation period, samples from the donor and receiver sides were removed and an equal volume of acetonitrile was added for protein precipitation. The supernatants were collected after centrifugation (3000 rpm, Allegra X-14R Centrifuge from Beckman Coulter, Indianapolis, IN) for LCMS analysis. The permeability value was determined according to the equation:

$$P_{app}(cm/s) = (F*VD)/(SA*MD),$$

where the flux rate (F, mass/time) is calculated from the slope of cumulative amounts of compound of interest on the receiver side, SA is the surface area of the cell membrane, VD is the donor volume, and MD is the initial amount of the solution in the donor chamber.

The Caco-2 permeability assay data are provided in Table 3 below. The symbol "†" indicates Caco2≤0.5; and "††" indicates Caco-2 is >0.5 but ≤1; and "†††" indicates Caco-2 is >1. "NA" indicates that Caco-2 data is not available.

TABLE 3

| Ex. No. | Caco-2 |
|---------|--------|
| 1a | ††† |
| 2a | ††† |
| 3a | ††† |
| 4a | †† |
| 5b | †† |
| 6b | †† |
| 7 | NA |

Example I: Human Whole Blood Stability

The whole blood stability of the exemplified compounds was determined by LC-MS/MS. The 96-Well Flexi-Tier™ Block (Analytical Sales & Services, Inc, Flanders, NJ) was used for the incubation plate containing 1.0 mL glass vials with 0.5 mL of blood per vial (pooled gender, human whole blood sourced from BIOIVT, Hicksville, NY or similar). Blood was pre-warmed in water bath to 37° C. for 30 minutes. 96-deep well analysis plate was prepared with the addition of 100 µL ultrapure water/well. 50 µL chilled ultrapure water/well was added to 96-deep well sample collection plate and covered with a sealing mat. 1 µL of 0.5 mM compound working solution (DMSO:water) was added to the blood in incubation plate to reach final concentrations of 1 µM, mixed by pipetting thoroughly and 50 µL was transferred 50 into the T=0 wells of the sample collection plate. Blood was allowed to sit in the water for 2 minutes and then 400 µL stop solution/well was added (acetonitrile containing an internal standard). The incubation plate was placed in the Incu-Shaker $CO_2$ Mini incubator (Benchmark Scientific, Sayreville, NJ) at 37° C. with shaking at 150 rpm. At 1, 2 and 4-hr, the blood samples were mixed thoroughly by pipetting and 50 µL is transferred into the corresponding wells of the sample collection plate. Blood was allowed to sit in the water for 2 minutes and then 400 µL of stop solution/well was added. The collection plate was sealed and vortexed at 1700 rpm for 3 minutes (VX-2500 Multi-Tube Vortexer, VWR International, Radnor, PA), and samples were then centrifuged in the collection plate at 3500 rpm for 10 minutes (Allegra X-14R Centrifuge Beckman Coulter, Indianapolis, IN). 100 µL of supernatant/well was transferred from the sample collection plate into the corresponding wells of the analysis plate. The final plate was vortexed at 1700 rpm for 1 minute and analyze samples by LC-MS/MS. The peak area ratio of the 1, 2, and 4 hr samples relative to T=0 was used to determine the percent remaining. The natural log of the percent remaining versus time was used determine a slope to calculate the compounds half-life in blood ($t_{1/2}$=0.693/slope).

The human whole blood stability data is provided in Table 4 below. The symbol "†" indicates WBS ≤70%; "††" indicates WBS >70% but ≤90%; and "†††" indicates WBS >90%. "NA" indicates that WBS data is not available.

TABLE 4

| Ex. No. | Human whole blood stability at 4 hr |
|---------|-------------------------------------|
| 1a      | †††                                 |
| 2a      | †††                                 |
| 3a      | †††                                 |
| 4a      | ††                                  |
| 5b      | NA                                  |
| 6b      | †††                                 |
| 7       | ††                                  |

Example J: In Vitro Intrinsic Clearance Protocol

For in vitro metabolic stability experiments, test compounds are incubated with human liver microsomes at 37° C. The incubation mixture contains test compounds (1 µM), NADPH (2 mM), and human liver microsomes (0.5 mg protein/mL) in 100 mM phosphate buffer (pH 7.4). The mixture is pre-incubated for 2 min at 37° C. before the addition of NADPH. Reactions are commenced upon the addition of NADPH and quenched with ice-cold methanol at 0, 10, 20, and 30 min. Terminated incubation mixtures are analyzed using LC-MS/MS system. The analytical system consisted of a Shimadzu LC-30AD binary pump system and SIL-30AC autosampler (Shimadzu Scientific Instruments, Columbia, MD) coupled with a Sciex Triple Quad 6500+ mass spectrometer from Applied Biosystems (Foster City, CA). Chromatographic separation of test compounds and internal standard is achieved using a Hypersil Gold C18 column (50×2.1 mm, 5 µM, 175 Å) from ThermoFisher Scientific (Waltham, MA). Mobile phase A consists of 0.1% formic acid in water, and mobile phase B consists of 0.1% formic acid in acetonitrile. The total LC-MS/MS runtime can be 2.75 minutes with a flow rate of 0.75 mL/min. Peak area integrations and peak area ratio calculations are performed using Analyst software (version 1.6.3) from Applied Biosystems.

The in vitro intrinsic clearance, $CL_{int,\ in\ vitro}$, is calculated from the $t_{1/2}$ of test compound disappearance as $CL_{int,\ in\ vitro} = (0.693/t_{1/2}) \times (1/C_{protein})$, where $C_{protein}$ is the protein concentration during the incubation, and $t_{1/2}$ is determined by the slope (k) of the log-linear regression analysis of the concentration versus time profiles; thus, $t_{1/2} = \ln 2/k$. The $CL_{int,\ in\ vitro}$ values are scaled to the in vivo values for human by using physiologically based scaling factors, hepatic microsomal protein concentrations (45 mg protein/g liver), and liver weights (21 g/kg body weight). The equation $CL_{int} = CL_{int,\ in\ vitro} \times (\text{mg protein/g liver weight}) \times (\text{g liver weight/kg body weight})$ is used. The in vivo hepatic clearance ($CL_H$) is then calculated by using $CL_{int}$ and hepatic blood flow, Q (20 mL·min$^{-1}$·kg$^{-1}$ in humans) in the well-stirred liver model disregarding all binding from $CL_H = (Q \times CL_{int})/(Q + CL_{int})$. The hepatic extraction ratio was calculated as $CL_H$ divided by Q.

Example K: In Vivo Pharmacokinetics Protocol

For in vivo pharmacokinetic experiments, test compounds are administered to male Sprague Dawley rats or male and female Cynomolgus monkeys intravenously or via oral gavage. For intravenous (IV) dosing, test compounds are dosed at 0.5 to 1 mg/kg using a formulation of 10% dimethylacetamide (DMAC) in acidified saline via IV bolus for rat and 5 min or 10 min IV infusion for monkey. For oral (PO) dosing, test compounds are dosed at 1.0 to 3.0 mg/kg using 5% DMAC in 0.5% methylcellulose in citrate buffer (pH 2.5). Blood samples are collected at predose and various time points up to 24 hours postdose. All blood samples are collected using EDTA as the anticoagulant and centrifuged to obtain plasma samples. The plasma concentrations of test compounds are determined by LC-MS methods. The measured plasma concentrations are used to calculate PK parameters by standard noncompartmental methods using Phoenix® WinNonlin software program (version 8.0, Pharsight Corporation).

In rats and monkeys, cassette dosing of test compounds are conducted to obtain preliminary PK parameters.

In vivo pharmacokinetic experiments with male beagle dogs may be performed under the conditions described above.

Example L: Time Dependent Inhibition (TDI) of CYP Protocol

This assay is designed to characterize an increase in CYP inhibition as a test compounds is metabolized over time. Potential mechanisms for this include the formation of a tight-binding, quasi-irreversible inhibitory metabolite complex or the inactivation of P450 enzymes by covalent adduct formation of metabolites. While this experiment employs a 10-fold dilution to diminish metabolite concentrations and therefore effects of reversible inhibition, it is possible (but not common) that a metabolite that is an extremely potent CYP inhibitor could result in a positive result.

The results are from a cocktail of CYP specific probe substrates at 4 times their Km concentrations for CYP2C9, 2C19, 2D6 and 3A4 (midazolam) using human liver microsomes (HLM). The HLMs can be pre-incubated with test compounds at a concentration 10 µM for 30 min in the presence (+N) or absence (−N) of a NADPH regenerating system, diluted 10-fold, and incubated for 8 min in the presence of the substrate cocktail with the addition of a fresh aliquot of NADPH regenerating system. A calibration curve of metabolite standards can be used to quantitatively measure the enzyme activity using LC-MS/MS. In addition, incubations with known time dependent inhibitors, tienilic acid (CYP2C9), ticlopidine (CYP2C19), paroxetine (CYP2D6), and troleandomycin (CYP3A4), used as positive controls are pre-incubated 30 min with or without a NADPH regenerating system.

The analytical system consists of a Shimadzu LC-30AD binary pump system and SIL-30AC autosampler (Shimadzu Scientific Instruments, Columbia, MD) coupled with a Sciex Triple Quad 6500+ mass spectrometer from Applied Biosystems (Foster City, CA). Chromatographic separation of test compounds and internal standard can be achieved using an ACQUITY UPLC BEH 130A, 2.1×50 mm, 1.7 µm HPLC column (Waters Corp, Milford, MA). Mobile phase A consists of 0.1% formic acid in water, and mobile phase B consists of 0.1% formic acid in acetonitrile. The total LC-MS/MS runtime will be 2.50 minutes with a flow rate of 0.9 mL/min. Peak area integrations and peak area ratio calculations are performed using Analyst software (version 1.6.3) from Applied Biosystems.

The percentage of control CYP2C9, CYP2C19, CYP2D6, and CYP3A4 activity remaining following preincubation of the compounds with NADPH is corrected for the corresponding control vehicle activity and then calculated based on 0 minutes as 100%. A linear regression plot of the natural log of % activity remaining versus time for each isozyme is used to calculate the slope. The −slope is equal to the rate of enzyme loss, or the $K_{obs}$.

What is claimed is:

1. A compound having Formula (I)

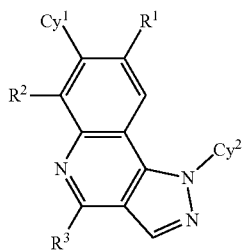

I or a pharmaceutically acceptable salt thereof, wherein:
$R^1$ is selected from Cl, $CH_3$, $CH_2F$, $CHF_2$, and $CF_3$;
$Cy^1$ is

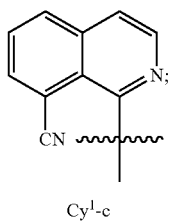 [SMILES: *c1nccc2cccc(C#N)c12]

$Cy^1$-c $R^2$ is selected from F and Cl;
$R^3$ is selected from

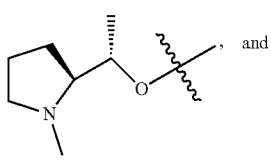, and $R^3$-a

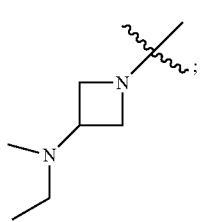;

$R^3$-b and,
$Cy^2$ is selected from

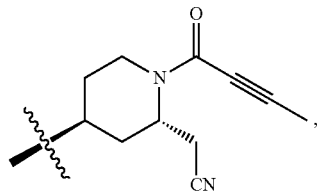, $Cy^2$-a

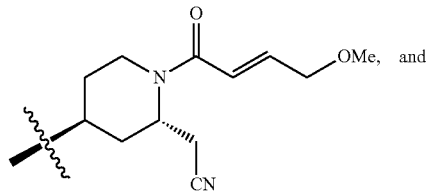, and $Cy^2$-b

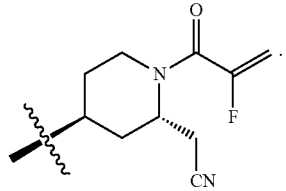.

$Cy^2$-c

2. The compound of claim 1, or a pharmaceutically acceptable salt thereof, wherein
$R^1$ is selected from Cl, $CH_2F$, $CHF_2$, and $CF_3$;
$Cy^1$ is

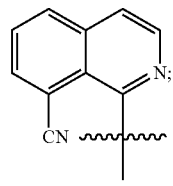

$Cy^1$-c $R^2$ is selected from F and Cl;
$R^3$ is selected from

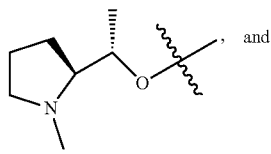, and $R^3$-a

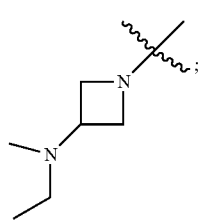;

$R^3$-b and
Cy² is selected from

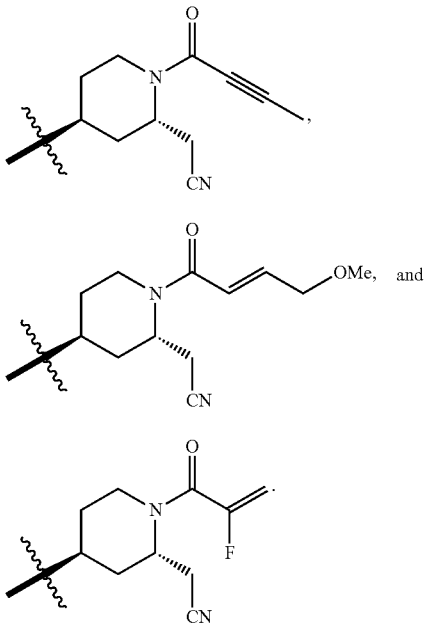

3. The compound of claim 1, or a pharmaceutically acceptable salt thereof, wherein R¹ is selected from CH₃, CH₂F, CHF₂, and CF₃.

4. The compound of claim 1, or a pharmaceutically acceptable salt thereof, wherein R¹ is selected from Cl, CH₃, and CF₃.

5. The compound of claim 1, or a pharmaceutically acceptable salt thereof, wherein R¹ is selected from CH₃ and CF₃.

6. The compound of claim 1, or a pharmaceutically acceptable salt thereof, wherein R² is F.

7. The compound of claim 1, or a pharmaceutically acceptable salt thereof, wherein R² is Cl.

8. The compound of claim 1, or a pharmaceutically acceptable salt thereof, wherein R³ is R³-a.

9. The compound of claim 1, or a pharmaceutically acceptable salt thereof, wherein R³ is R³-b.

10. The compound of claim 1, or a pharmaceutically acceptable salt thereof, wherein Cy² is Cy²-b.

11. The compound of claim 1, or a pharmaceutically acceptable salt thereof, wherein Cy² is Cy²-a.

12. The compound of claim 1, or a pharmaceutically acceptable salt thereof, wherein Cy² is Cy²-c.

13. The compound of claim 1, wherein the compound is selected from
1-(1-((2S,4S)-1-(but-2-ynoyl)-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile;
1-(8-chloro-1-((2S,4S)-2-(cyanomethyl)-1-((E)-4-methoxybut-2-enoyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile; and
1-(8-chloro-1-((2S,4S)-2-(cyanomethyl)-1-(2-fluoroacryloyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile
or a pharmaceutically acceptable salt thereof.

14. A pharmaceutical composition comprising a compound of claim 1, or a pharmaceutically acceptable salt thereof, and at least one pharmaceutically acceptable carrier or excipient.

15. A method of inhibiting KRAS activity, said method comprising contacting a compound of claim 1 with KRAS.

16. A method of treating a disease or disorder associated with abnormal expression or activity of KRAS interaction, said method comprising administering to a patient in need thereof a therapeutically effective amount of a compound of claim 1, or a pharmaceutically acceptable salt thereof.

17. A method of treating a disease or disorder associated with abnormal expression or activity of a KRAS protein harboring a G12C mutation, said method comprising administering to a patient in need thereof a therapeutically effective amount of a compound of claim 1, or a pharmaceutically acceptable salt thereof.

18. A method for treating a cancer in a patient, said method comprising administering to the patient a therapeutically effective amount of the compound of claim 1, or a pharmaceutically acceptable salt thereof.

19. The method of claim 18, wherein the cancer is selected from carcinomas, hematological cancers, sarcomas, and glioblastoma.

20. The method of claim 19, wherein the cancer is a hematological cancer selected from myeloproliferative neoplasms, myelodysplastic syndrome, chronic and juvenile myelomonocytic leukemia, acute myeloid leukemia, acute lymphocytic leukemia, and multiple myeloma.

21. The method of claim 19, wherein the cancer is a carcinoma selected from pancreatic, colorectal, lung, bladder, gastric, esophageal, breast, head and neck, cervical, skin, and thyroid carcinoma.

22. The method of claim 16, wherein the disease or disorder is an immunological or inflammatory disorder.

23. The method of claim 22, wherein the immunological or inflammatory disorder is Ras-associated lymphoproliferative disorder or juvenile myelomonocytic leukemia caused by somatic mutations of KRAS.

24. The compound of claim 1, wherein the compound is 1-(1-((2S,4S)-1-(but-2-ynoyl)-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile, or a pharmaceutically acceptable salt thereof.

25. The compound of claim 1, wherein the compound is 1-(8-chloro-1-((2S,4S)-2-(cyanomethyl)-1-((E)-4-methoxybut-2-enoyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile, or a pharmaceutically acceptable salt thereof.

26. The compound of claim 1, wherein the compound is 1-(8-chloro-1-((2S,4S)-2-(cyanomethyl)-1-(2-fluoroacryloyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile, or a pharmaceutically acceptable salt thereof.

* * * * *